US009773986B2

(12) United States Patent
Thompson et al.

(10) Patent No.: US 9,773,986 B2
(45) Date of Patent: *Sep. 26, 2017

(54) COPPER(I)-CARBENE COMPLEXES AND ORGANIC ELECTROLUMINESCENT DEVICES

(71) Applicant: The University of Southern California, Los Angeles, CA (US)

(72) Inventors: Mark Thompson, Anaheim, CA (US); Peter Djurovich, Long Beach, CA (US); Valentina Krylova, Los Angeles, CA (US)

(73) Assignee: THE UNIVERSITY OF SOUTHERN CALIFORNIA, Los Angeles, CA (US)

( * ) Notice: Subject to any disclaimer, the term of this patent is extended or adjusted under 35 U.S.C. 154(b) by 860 days.

This patent is subject to a terminal disclaimer.

(21) Appl. No.: 14/060,006

(22) Filed: Oct. 22, 2013

(65) Prior Publication Data
US 2014/0125221 A1    May 8, 2014

Related U.S. Application Data

(63) Continuation of application No. 12/948,396, filed on Nov. 17, 2010, now Pat. No. 8,580,394.

(60) Provisional application No. 61/402,989, filed on Sep. 9, 2010, provisional application No. 61/398,808, filed on Jul. 1, 2010, provisional application No. 61/301,362, filed on Feb. 4, 2010, provisional application No. 61/262,804, filed on Nov. 19, 2009.

(51) Int. Cl.
*H01L 51/54* (2006.01)
*H01L 51/00* (2006.01)
*C07F 1/08* (2006.01)
*C09K 11/06* (2006.01)
*H01L 51/50* (2006.01)

(52) U.S. Cl.
CPC ............ *H01L 51/0091* (2013.01); *C07F 1/08* (2013.01); *C09K 11/06* (2013.01); *C09K 2211/188* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,627,164 A | 5/1997 | Gorun et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 8,580,394 B2 * | 11/2013 | Thompson et al. | ...... C07F 1/08 252/301.16 |
| 2002/0034656 A1 | 3/2002 | Thompson et al. | |

(Continued)

FOREIGN PATENT DOCUMENTS

EP    0650955    5/1995
EP    1725079    11/2006

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3 (2007).
Baldo et al., Highly Efficient Phosphorescent Emission from Organic Electroluminescent Devices, Nature, vol. 395, 151-154, (1998).

(Continued)

Primary Examiner — Marie R. Yamnitzky
(74) Attorney, Agent, or Firm — Duane Morris LLP

(57) ABSTRACT

Devices comprising an organic light emitting device are provided. The devices can include an anode; a cathode; and an organic layer, disposed between the anode and the cathode. The organic layer comprising at least one host material comprising a phosphorescent complex comprising novel phosphorescent trigonal copper carbene complexes. The complex comprise a carbene ligand coordinated to a three coordinate copper atom. The complex may be used in organic light emitting devices. In particular, the complexes may be especially useful in OLEDs used for lighting applications.

17 Claims, 31 Drawing Sheets

(56) References Cited

U.S. PATENT DOCUMENTS

| | | |
|---|---|---|
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2004/0192664 A1 | 9/2004 | Kunz et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0258742 A1 | 11/2005 | Tsai et al. |
| 2005/0260441 A1 | 11/2005 | Thompson et al. |
| 2005/0260446 A1 | 11/2005 | Mackenzie et al. |
| 2005/0260449 A1 | 11/2005 | Walters et al. |
| 2006/0008670 A1 | 1/2006 | Lin et al. |
| 2006/0024522 A1 | 2/2006 | Thompson |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0258043 A1* | 11/2006 | Bold et al. ......... C07F 15/0033 438/99 |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0004385 A1 | 1/2009 | Blackwell et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0140640 A1 | 6/2009 | Thompson et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2007297347 | 11/2007 |
| JP | 2008074939 | 4/2008 |
| JP | 2008303152 | 12/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005/007659 | 1/2005 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010031485 | 3/2010 |

OTHER PUBLICATIONS

Baldo et al., Very high-efficiency green organic light-emitting devices based on electrophosphorescence Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1, 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

(56) References Cited

OTHER PUBLICATIONS

Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4'4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet: Luminescent Dinuclear-Gold(I) Complex-Based Light-Emitting Diodes with Low Turn-On voltage," Appl. Phys. Lett., 74(10)1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Ernitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N N^C^N C N^C^N N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic. Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Zhao et al., "DFT studies on the mechanism of the diboration of aldehydes catalyzed by copper(I) boryl complexes" JACS Articles, J. Am. Chem. Soc. 2008, 130, pp. 5586-5594.
Yun et al., "A new alternative to Stryker's reagent in hydrosilytation: synthesis, structure, and reactivity of a well-defined carbene-copper(II) acetate complex" Chem. Commun. 2005, 5181-5183.
York et al. "Heterobimetallic activation of dioxygen: Characterization and reactivity of novel Cu(I)-Ge(II) complexes" Inorganic Chemistry, vol. 45, No. 10, 2006, 4191-4198.
Mankad et al., "Synthesis, structure, and CO2 reactivity of a two-coordinate (Carbene)copper(I) methyl complex" Organometallics 2004, 23, pp. 1191-1193.
Arnold et al., "Asymmetric lithium(I) and copper(II) alkoxy-N-heterocyclic carbene complexes: crystallographic characterization and Lewis acid catalysis" Chem. Commun. 2004, 1612-1613.
Welle et al., "A three-component tandem reductive aldol reaction catalyzed by N-heterocyclic carbene-copper complexes" Organic letters, 2006, vol. 8, No. 26, 6059-6062.
Hu et al. "Copper Complexes of Nitrogen-Anchored Tripodal N-Heterocyclic Carbene Ligands", J. Am. Chem. Soc. 2003, 125, 12237-12245.
U.S. Appl. No. 61/262,804, filed Nov. 19, 2009.
U.S. Appl. No. 61/301,362, filed Feb. 4, 2010.
U.S. Appl. No. 61/398,808, filed Jul. 1, 2010.
U.S. Appl. No. 61/402,989, filed Sep. 9, 2010.
Armaroli, N et al., "Highly luminescent Cu-I complexes for light-emitting electrochemical cells" Advanced Materials 2006, 18, (10), 1313-1316.
Zhang et al., "Highly efficient green phosphorescent organic light-emitting diodes based on Cu-I complexes" Advanced Materials 2004, 16, (5), 432-436.
Sivasankar, C. et al., "Synthesis, spectroscopic characterization and electronic structure of some new Cu(I) carbene complexes", J. Chem. Sci., vol. 118, No. 3, May 2006, pp. 237-242.
Notice of Reasons for Rejection issued on Jul. 14, 2014 for corresponding JP Patent Application No. 2012-540041.
Extended European Search Report issued on Feb. 26, 2014 for corresponding EP Patent Application No. 10832153.0.
International Search Report issued on Jan. 27, 2011 for corresponding PCT Application No. PCT/US10/57169.

\* cited by examiner

A.

B.

A.

B.

US 9,773,986 B2

COPPER(I)-CARBENE COMPLEXES AND ORGANIC ELECTROLUMINESCENT DEVICES

This application is a continuation of U.S. application Ser. No. 12/948,396, filed Nov. 17, 2010, now U.S. Pat. No. 8,580,394, which claims priority to U.S. Provisional Application Ser. No. 61/262,804, filed Nov. 19, 2009, U.S. Provisional Application Ser. No. 61/301,362, filed Feb. 4, 2010, U.S. Provisional Application Ser. No. 61/398,808, filed Jul. 1, 2010, and U.S. Provisional Application Ser. No. 61/402,989, filed Sep. 9, 2010, the disclosures of which are herein expressly incorporated by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to phosphorescent copper complexes, and their use in organic light emitting devices (OLEDs). More particularly, the invention relates to phosphorescent complexes comprising a carbene ligand coordinated to a three coordinate copper atom, and devices containing such complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

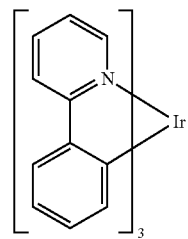

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Novel phosphorescent complexes are provided, the complexes comprising a carbene ligand coordinated to a three coordinate copper atom.

In one aspect, the carbene ligand has the formula:

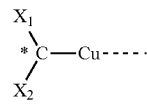

Formula I

*C is a divalent carbon atom coordinated to a monovalent copper atom Cu. $X_1$ and $X_2$ are substituents independently selected from alkyl, amine, phosphine, heteroalkyl, aryl and heteroaryl. $X_1$ and $X_2$ may be further substituted, and $X_1$ and $X_2$ are optionally linked to form a cycle. In one aspect, the carbene ligand is monodentate. Preferably, each of $X_1$ and $X_2$ independently forms a bond with *C. A first bond is formed between *C and an atom $X'_1$ in substituent $X_1$, and a second bond is formed between *C and an atom $X'_2$ in substituent $X_2$. $X'_1$ and $X'_2$ are independently selected from the group consisting of C, N, O, S and P.

In another aspect, the carbene ligand is monodentate.

In one aspect, $X_1$ and $X_2$ are not joined to form a cycle. In another aspect, $X_1$ and $X_2$ are joined to form a cycle.

In one aspect, the copper complex is neutral. In another aspect, the copper complex is charged.

In one aspect, the complex has the formula:

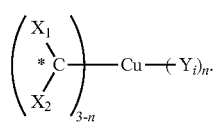

Formula II

Yi is independently selected from the group consisting of alkyl, alkoxy, amino, alkenyl, alkynyl, arylalkyl, heteroalkyl, aryl and heteroaryl. Yi is a monodentate ligand or a bidentate ligand. n is 1 or 2. Preferably, n is 2.

In another aspect, the complex has the formula:

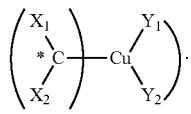

Formula III $Y_1$ and $Y_2$ are substituents that are independently selected from the group consisting of alkyl, heteroalkyl, aryl and heteroaryl. $Y_1$ and $Y_2$ may be further substituted. $Y_1$ and $Y_2$ are joined. Each of $Y_1$ and $Y_2$ form a bond with Cu. A first bond is formed between Cu and an atom $Y'_1$ in substituent $Y_1$ and a second bond is formed between Cu and an atom $Y'_2$ in substituent $Y_2$. $Y'_1$ is selected from the group consisting of N, P, *C, O, and S. $Y'_2$ is selected from the group consisting of N, P, *C, tetravalent carbon, O, and S. Preferably, $Y'_1$ is N. Preferably, the ring comprising Cu, $Y'_1$ and $Y'_2$ is a 5-membered or 6-membered ring.

In another aspect, $Y_1$ is selected from the group consisting of pyridyl, pyrazole, alkyl amine, imidazole, benzimidazole, triazole, tetrazole, pyridazine, pyrimidine, pyrazine, triazine, tetrazine, oxazole, thiazole, benzoxazole and benzothiazole.

In yet another aspect, $Y_1$-$Y_2$ is selected from the group consisting of:

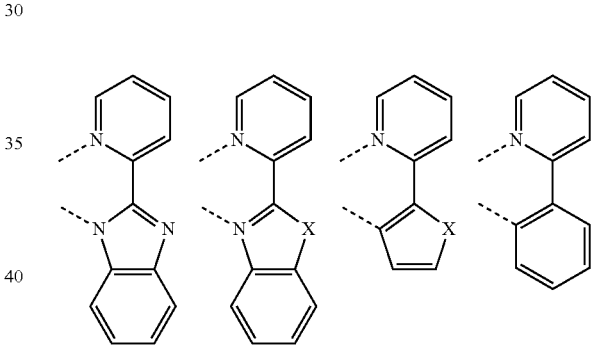

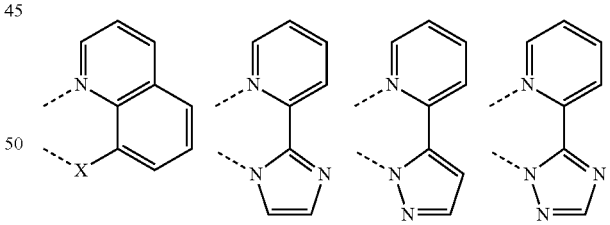

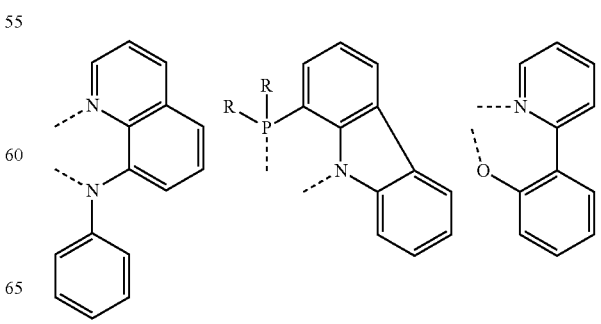

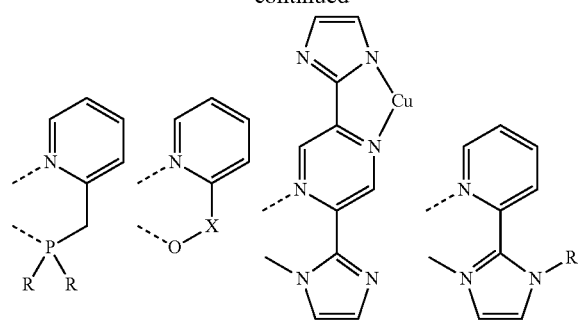

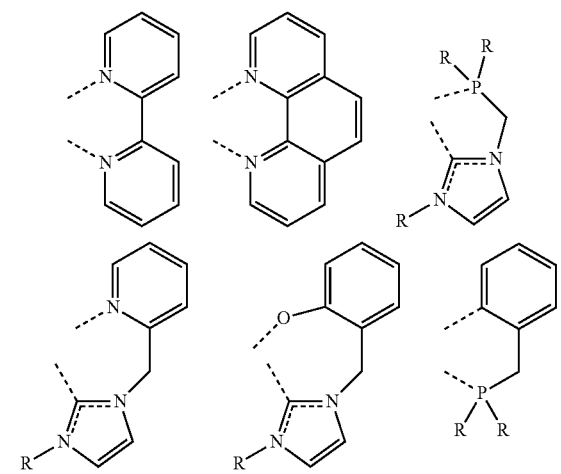

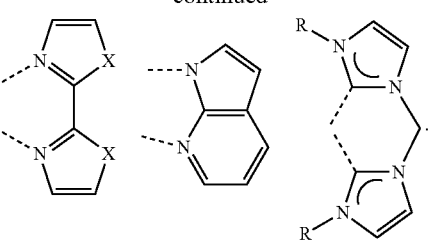

X is selected from the group consisting of NR, O, S, Se, CR$_2$, and CO. Each R is independently selected from the group consisting of hydrogen, alkyl, alkoxy, amino, alkenyl, alkynyl, arylalkyl, heteroalkyl, aryl and heteroaryl. Each ring is further substituted by a substituent selected from the group consisting of hydrogen, alkyl, alkoxy, amino, alkenyl, alkynyl, arylalkyl, heteroalkyl, aryl and heteroaryl.

In another aspect, each R includes a substituent independently selected from the group consisting of carbazole, dibenzofuran, dibenzothiophene, azacarbazole, azadibenzofuran, and azadibenzothiophene.

In yet another aspect, Y$_1$-Y$_2$ is selected from the group consisting of:

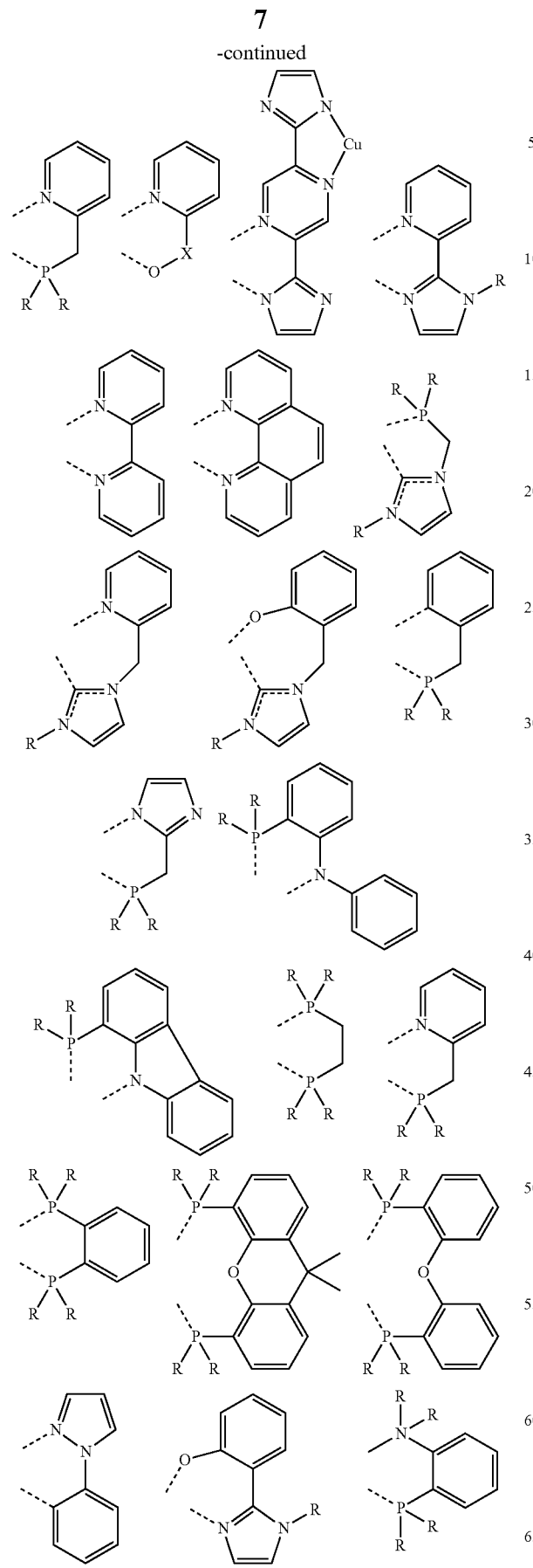
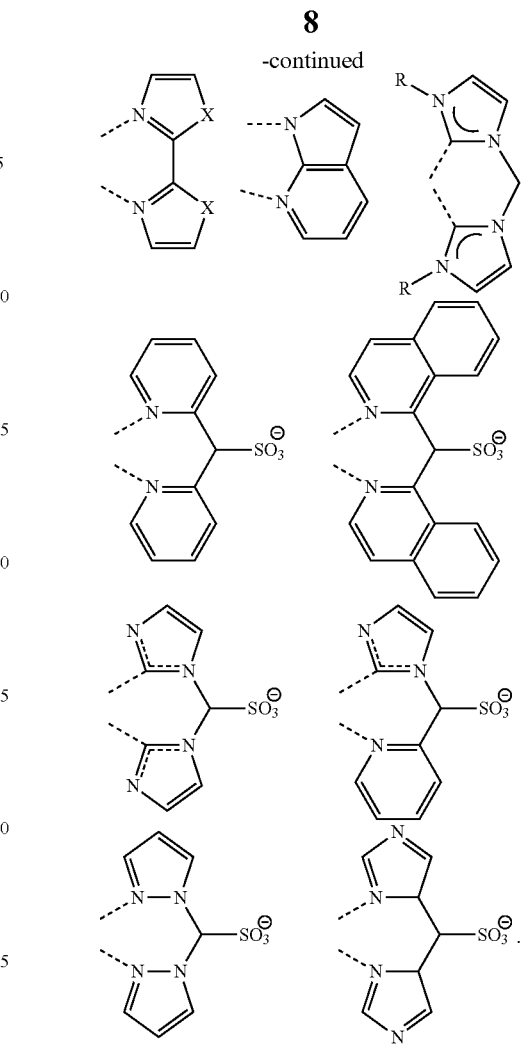

X is selected from the group consisting of NR, O, S, Se, CR$_2$, and CO. Each R is independently selected from the group consisting of hydrogen, alkyl, alkoxy, amino, alkenyl, alkynyl, arylalkyl, heteroalkyl, aryl and heteroaryl. Each ring is further substituted by a substituent selected from the group consisting of hydrogen, alkyl, alkoxy, amino, alkenyl, alkynyl, arylalkyl, heteroalkyl, aryl and heteroaryl.

In one aspect, each R includes a substituent independently selected from the group consisting of carbazole, dibenzofuran, dibenzothiophene, azacarbazole, azadibenzofuran, and azadibenzothiophene.

In another aspect, $Y_i$ is an unconjugated, monoanionic ligand containing $BY_4^-$, $SO_3Y^-$, $CY_4^-$, $SiO_4^-$, $OY_2^-$, or $SY_2^-$. Each Y is independently selected from the group consisting of hydrogen, alkyl, aryl, alkoxy, amino, alkenyl, alkynyl, arylalkyl, heteroalkyl and heteroaryl.

In one aspect, $Y_i$ is $BY_4^-$. In another aspect, the ligand Yi comprises two monodentate ligands, at least one of which is $BY_4^-$. Preferably, the ligand $Y_i$ has the formula:

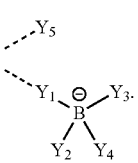

More preferably, the ligand $Y_i$ that comprises two monodentate ligands, at least one of which is $BY_4^-$, is selected from the group consisting of:

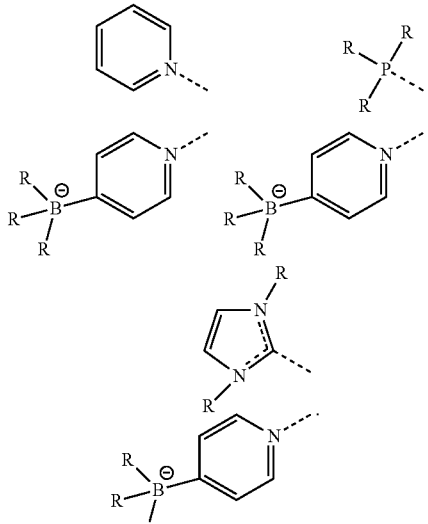

$Y_1$ and $Y_2$ are independently selected from the group consisting of pyridyl, pyrimidyl, pyrazinyl, pyridazinyl, triazinyl, tetrazinyl, triazolyl, tetrazolyl, pyrazolyl, imidazolyl, benzimidazolyl, oxazolyl, thiazolyl, benzoxazolyl, benzothiazolyl and phosphine. $Y_1$ and $Y_2$ may be extended by fusion, e.g., benzanulation. Additionally, $Y_1$ and $Y_2$ may be further substituted with alkyl, aryl, donor or acceptor groups. $Y_3$ and $Y_4$ are independently selected from the group consisting of hydrogen, alkyl, aryl, alkoxy, amino, alkenyl, alkynyl, arylalkyl, heteralkyl and heteroaryl. In one aspect, $Y_3$ and $Y_4$ are joined to form a cycle, may be extended by fusion, e.g., benzanulation.

In another aspect, $Y_i$ is a bidentate ligand having the formula $BY_4^-$. Preferably, the ligand $Y_i$ is selected from the group consisting of:

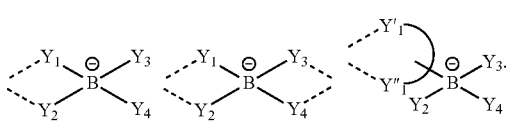

In this aspect, $Y_1$ is a bidentate chelating ligand having the formula:

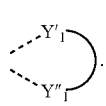

$Y'_1$-$Y''_1$ represents a neutral, i.e., uncharged, chealting ligand. $Y'_1$-$Y''_1$ are capable of coordinating to a metal center.

Specific examples of the $Y'_1$-$Y''_1$ ligand include, but are not limited to, ligands having the structure:

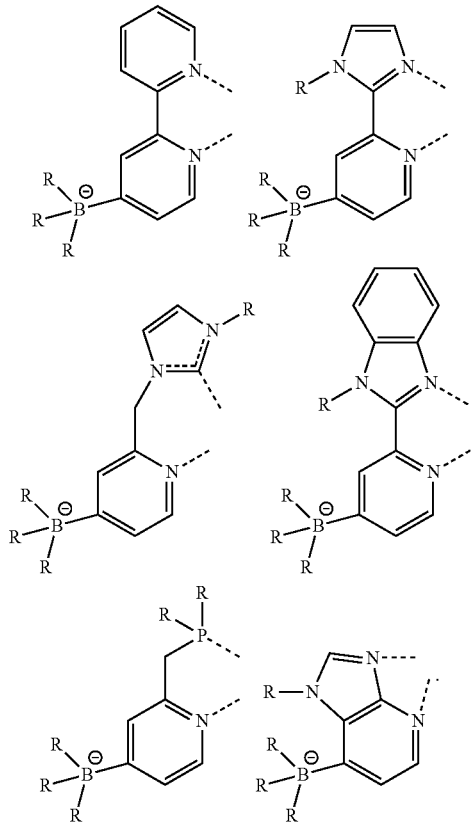

Each R is independently selected from the group consisting of hydrogen, alkyl, alkoxy, amino, alkenyl, alkynyl, arylalkyl, heteroalkyl, aryl and heteroaryl.

$Y_1$ and $Y_2$ are independently selected from the group consisting of pyridyl, pyrimidyl, pyrazinyl, pyridazinyl, triazinyl, tetrazinyl, triazolyl, tetrazolyl, pyrazolyl, imidazolyl, benzimidazolyl, oxazolyl, thiazolyl, benzoxazolyl, benzothiazolyl and phosphine. $Y_1$ and $Y_2$ may be extended by fusion, e.g., benzanulation. Additionally, $Y_1$ and $Y_2$ may be further substituted with alkyl, aryl, donor or acceptor groups.

$Y_3$ and $Y_4$ are independently selected from the group consisting of hydrogen, alkyl, aryl, alkoxy, amino, alkenyl, alkynyl, arylalkyl, heteralkyl and heteroaryl. In one aspect, $Y_3$ and $Y_4$ are joined to form a cycle, which may be extended by fusion, e.g., benzanulation.

In one aspect, $Y_1$ and $Y_2$ are the same. Specific examples of ligands where $Y_1$ and $Y_2$ are the same include, but are not limited to, ligands selected from the group consisting of:

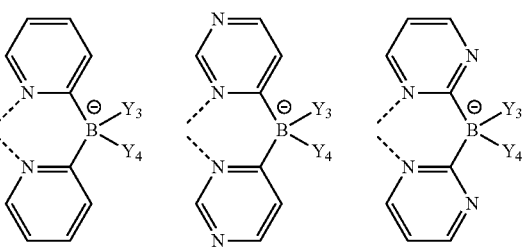

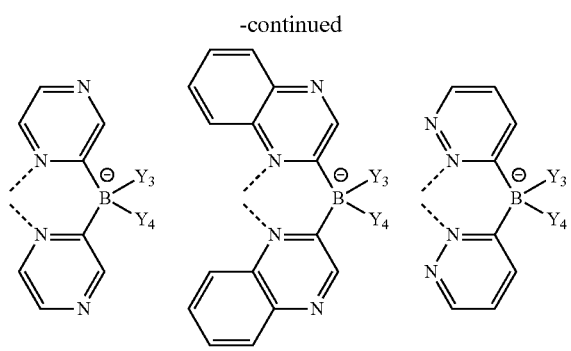
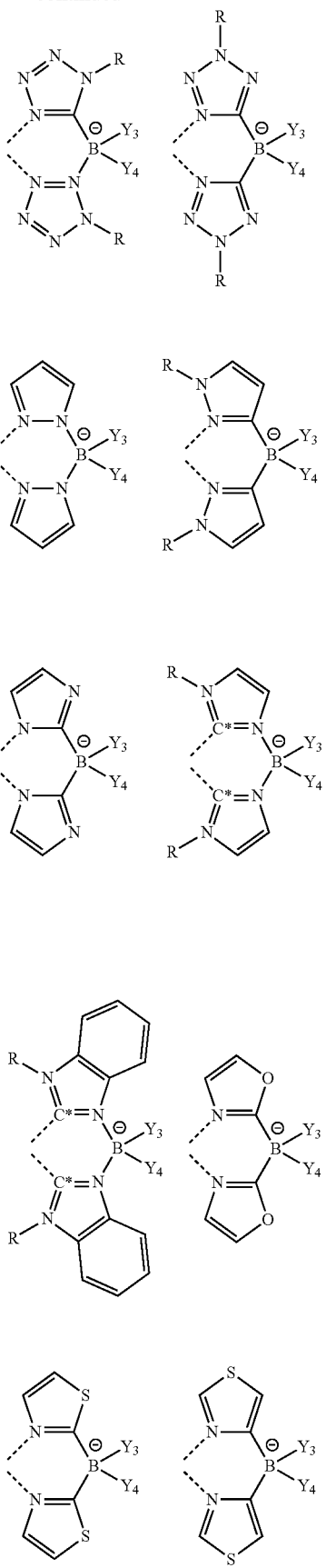

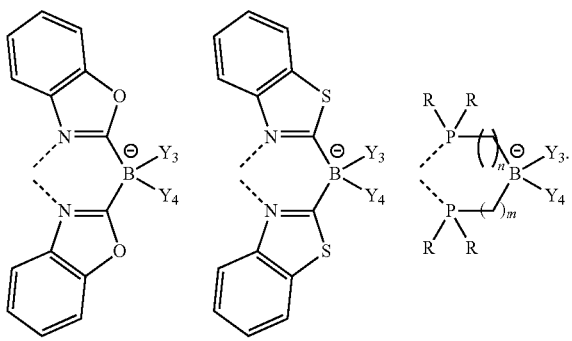

Each R is independently selected from the group consisting of hydrogen, alkyl, alkoxy, amino, alkenyl, alkynyl, arylalkyl, heteroalkyl, aryl and heteroaryl. C* is a divalent carbon atom. n is 0, 1, or 2. m is 0, 1, or 2.

In one aspect, $Y_1$ and $Y_2$ are different. Specific examples of ligands where $Y_1$ and $Y_2$ are different include, but are not limited to, ligands selected from the group consisting of:

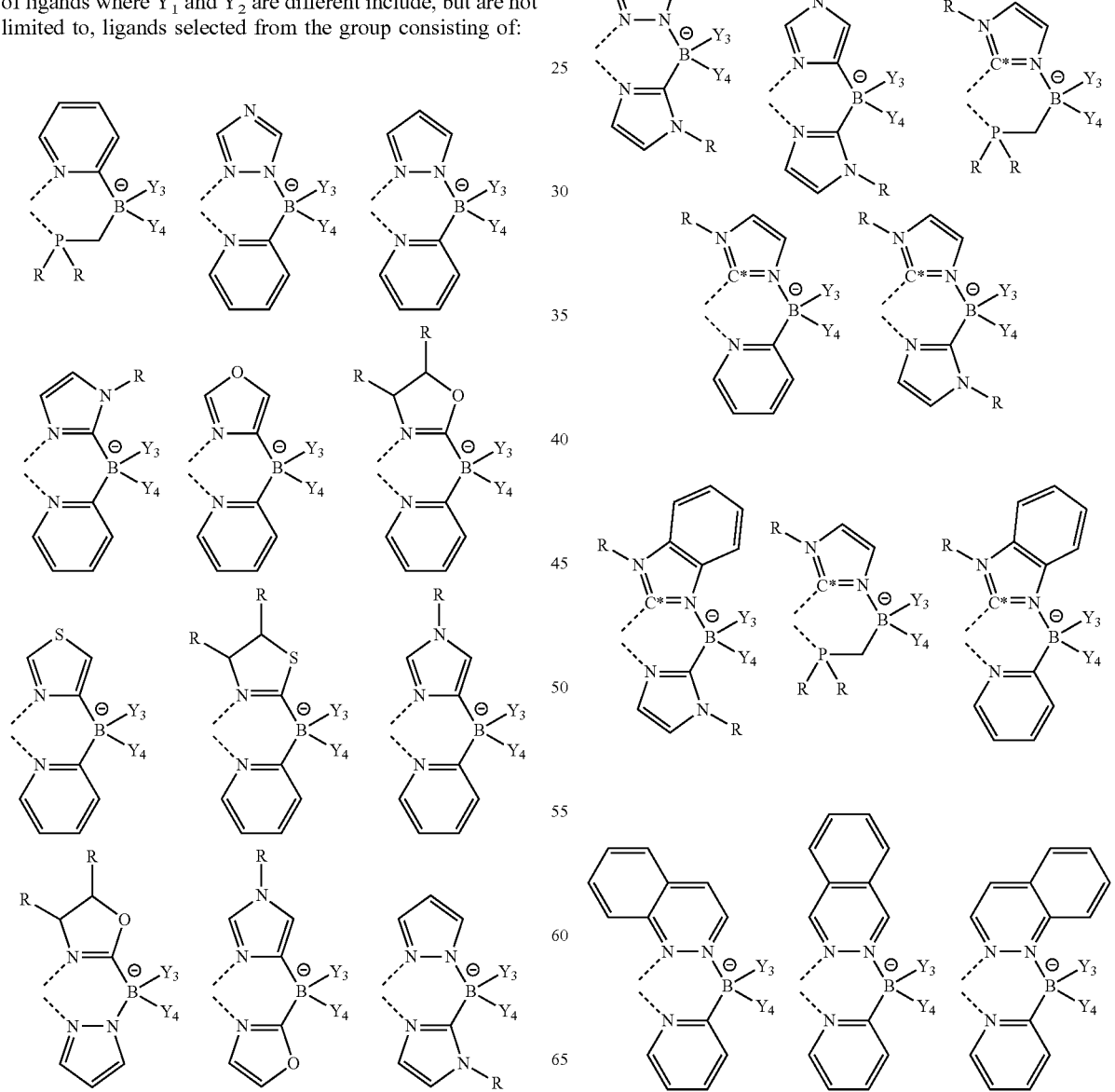

-continued

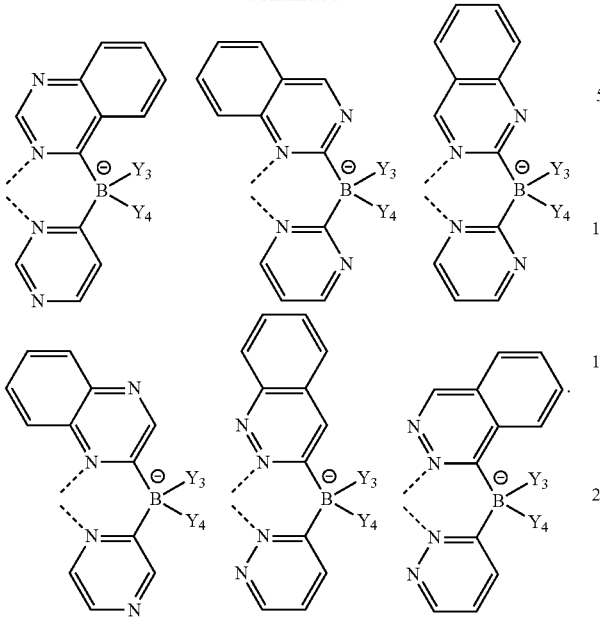

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

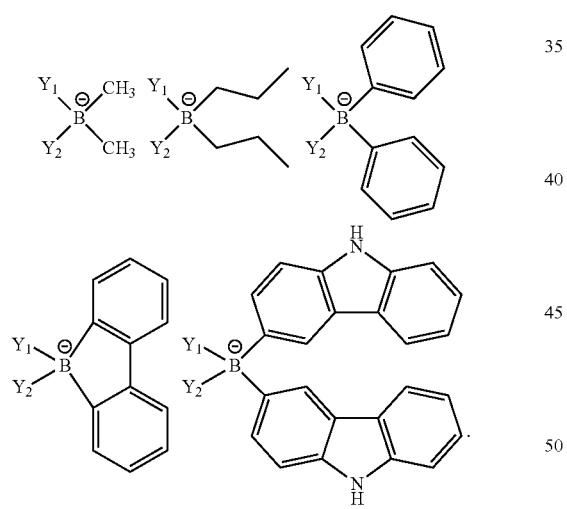

In one aspect, $Y_i$ is $SO_3Y^-$. Specific examples of ligands $Y_i$ having the formula $SO_3Y^-$ include, but are not limited to, ligands having the structure:

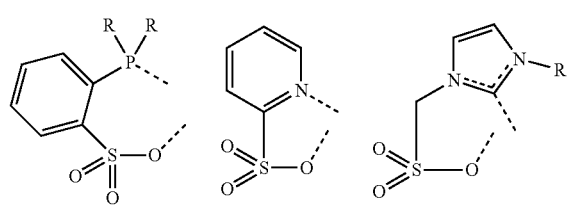

-continued

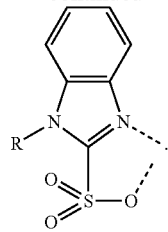

Each R is independently selected from the group consisting of hydrogen, alkyl, alkoxy, amino, alkenyl, alkynyl, arylalkyl, heteroalkyl, aryl and heteroaryl.

In one aspect, $Y_i$ is $CY_4^-$. Preferably, $CY_4^-$ has the formula:

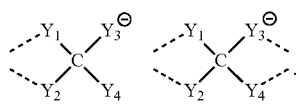

Specific examples of ligands $Y_i$ having the formula $CY_4^-$ include, but are not limited to, ligands having the structure:

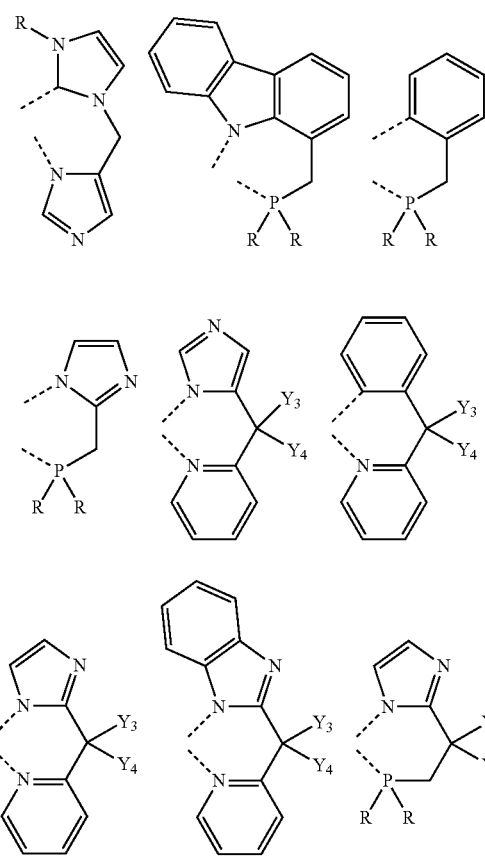

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

In another aspect, $Y_i$ is $SiY_4^-$. Specific examples of ligands $Y_i$ having the formula $SiY_4^-$ include, but are not limited to, ligands having the structure:

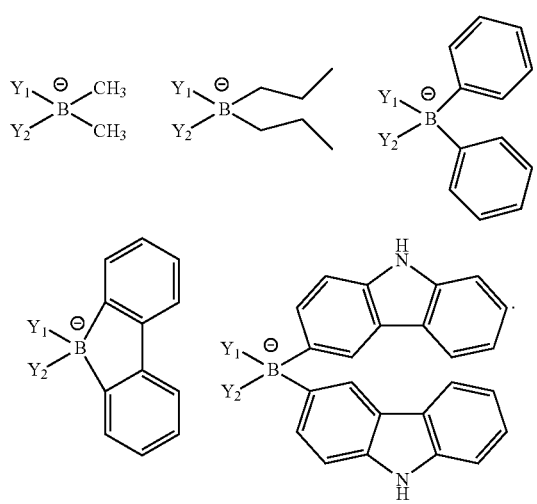

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

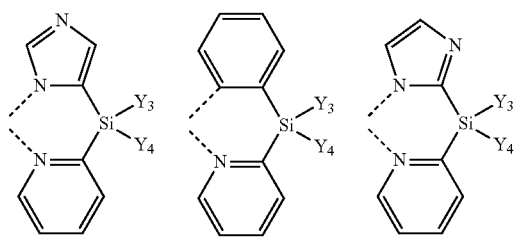

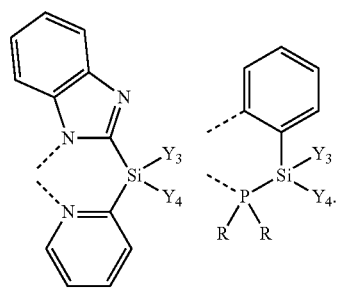

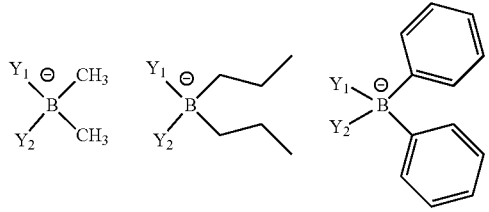

In another aspect, $Y_i$ is $OY_2^-$. Preferably, $OY_2^-$ has the formula:

Specific examples of ligands $Y_i$ having the formula $OY_2^-$ include, but are not limited to, ligands having the structure:

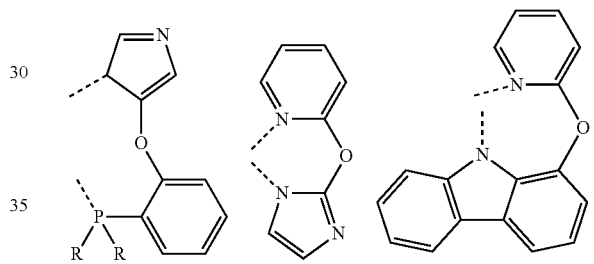

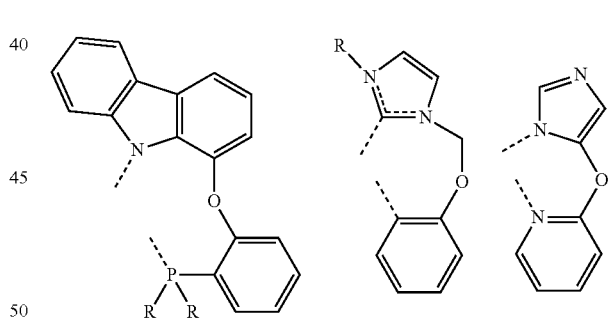

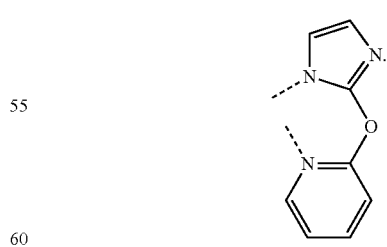

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

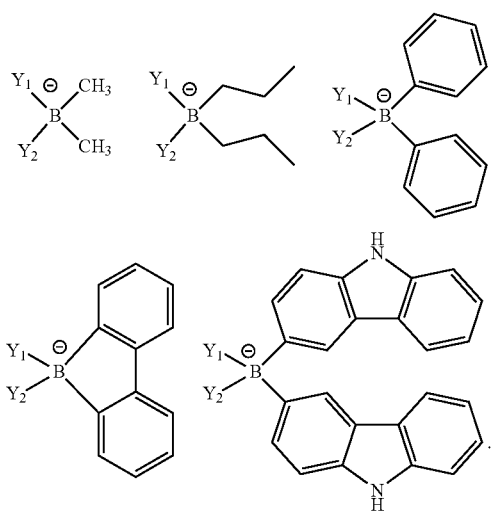

In yet another aspect, $Y_i$ is $SY_2^-$. Preferably, $SY_2^-$ has the formula:

Specific examples of ligands $Y_i$ having the formula $SY_2^-$ include, but are not limited to, ligands having the structure:

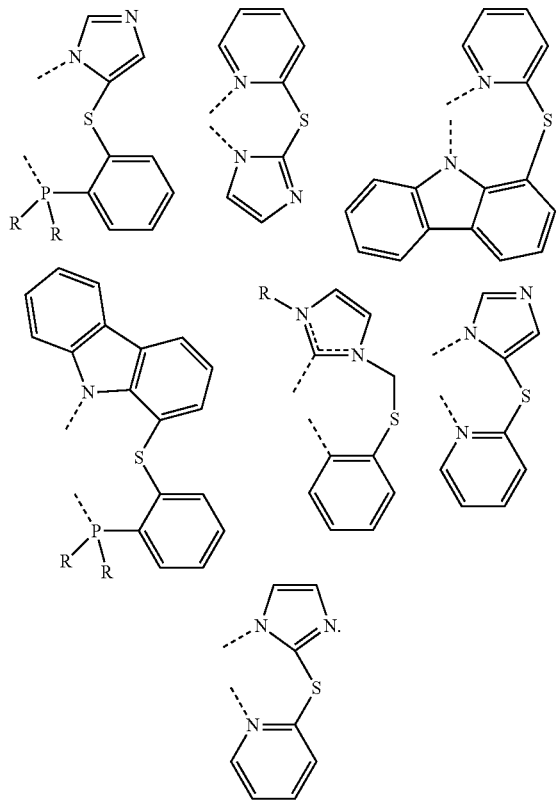

Each R is independently selected from the group consisting of hydrogen, alkyl, alkoxy, amino, alkenyl, alkynyl, arylalkyl, heteroalkyl, aryl and heteroaryl.

In one aspect, the complex comprises two copper (I) centers. Non-limiting examples of complexes comprising two copper (I) centers include complexes selected from the group consisting of:

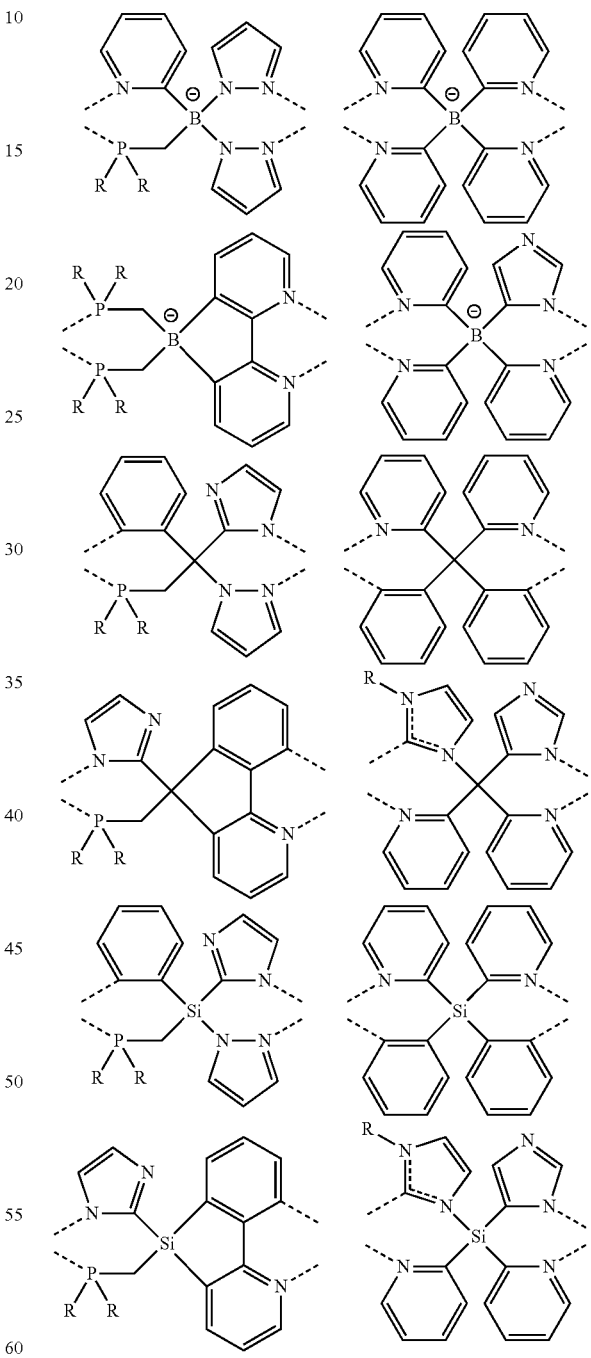

Each R is independently selected from the group consisting of hydrogen, alkyl, alkoxy, amino, alkenyl, alkynyl, arylalkyl, heteroalkyl, aryl and heteroaryl.

In a further aspect, the carbene ligand is selected from the group consisting of:

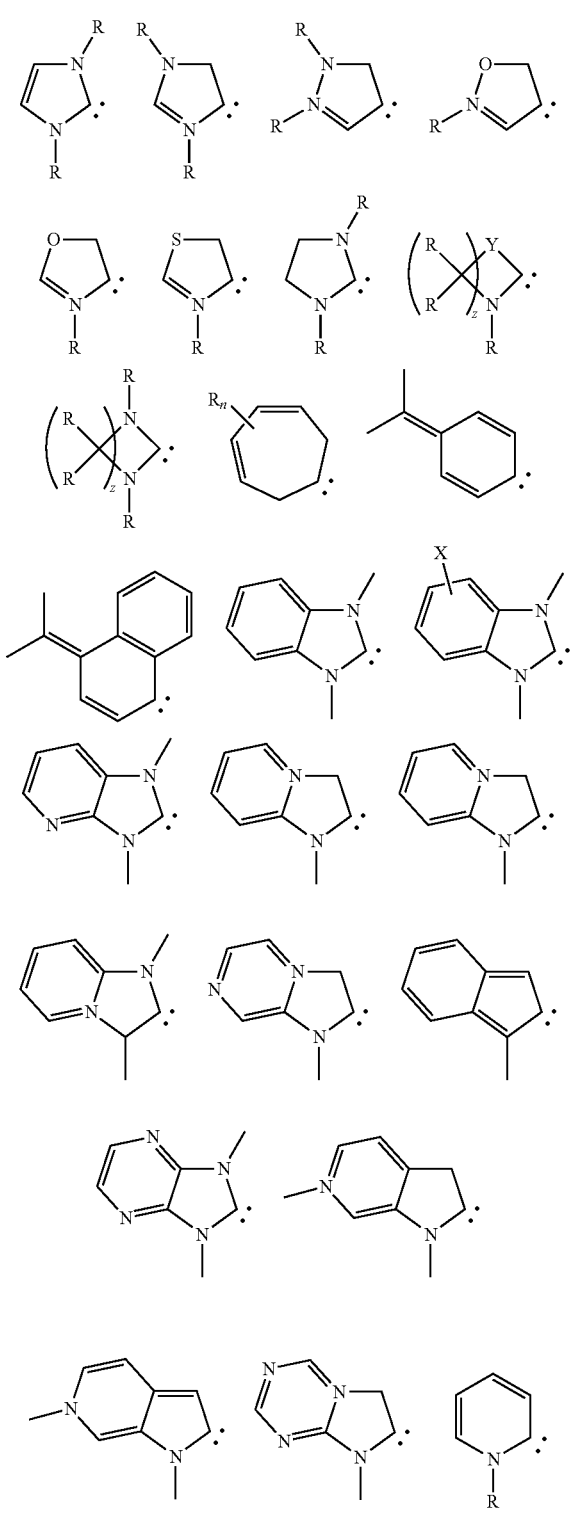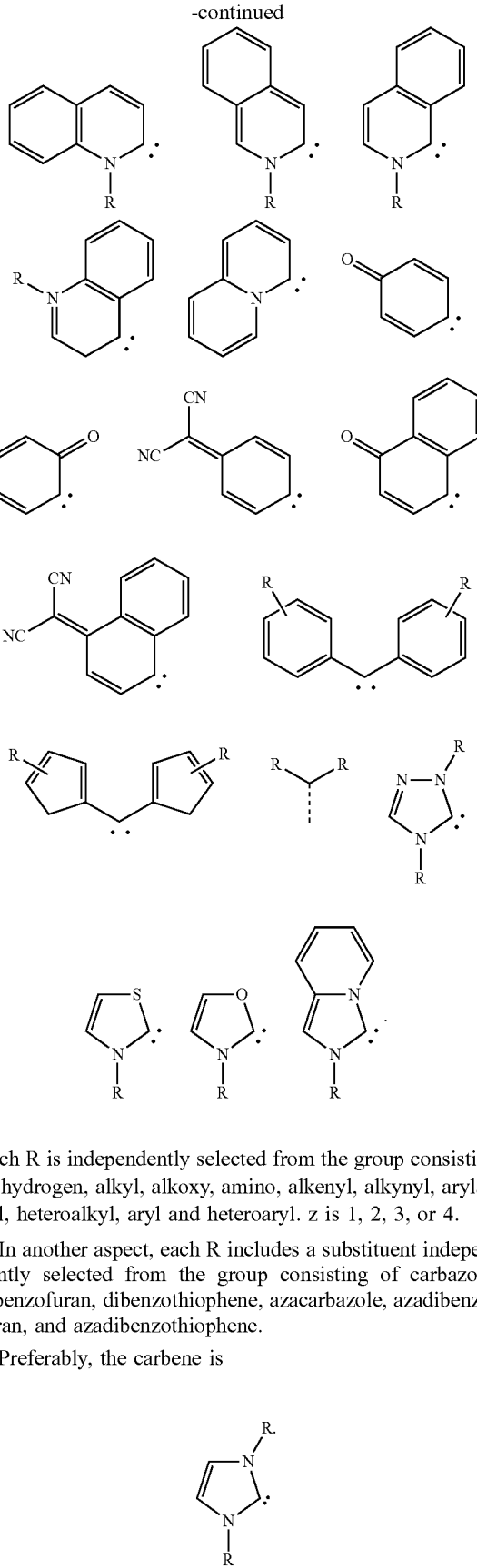

Each R is independently selected from the group consisting of hydrogen, alkyl, alkoxy, amino, alkenyl, alkynyl, arylalkyl, heteroalkyl, aryl and heteroaryl. z is 1, 2, 3, or 4.

In another aspect, each R includes a substituent independently selected from the group consisting of carbazole, dibenzofuran, dibenzothiophene, azacarbazole, azadibenzofuran, and azadibenzothiophene.

Preferably, the carbene is

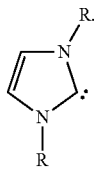

More preferably, the carbene is

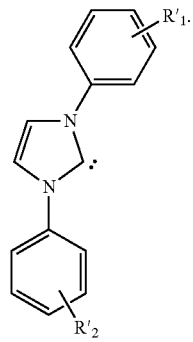

R'₁ and R'₂ may represent mono, di, tri, or tetra substitutions. R'₁ and R'₂ are independently selected from the group consisting of hydrogen, alkyl, alkoxy, amino, alkenyl, alkynyl, arylalkyl, heteroalkyl, aryl and heteroaryl. In one aspect, at least one of R'₁ and R'₂ is an alkyl having three or more carbon atoms.

Preferably, the complex is selected from the group consisting of:

Complex 1

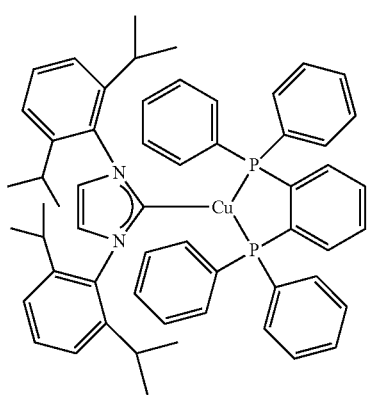

Complex 2

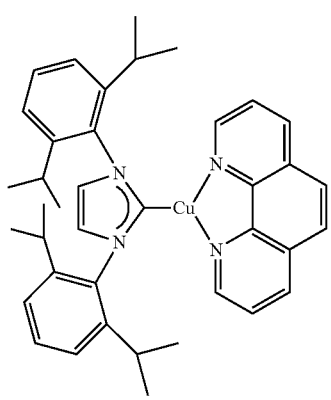

Complex 3

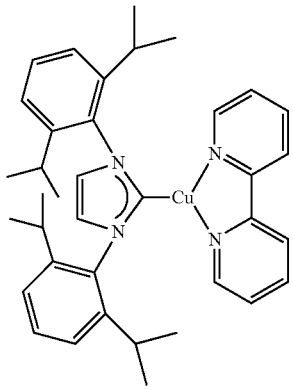

Complex 4

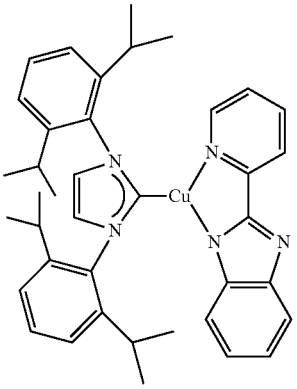

Complex 5

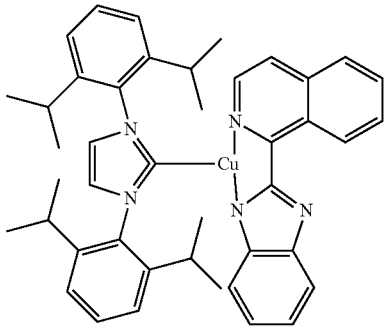

Complex 6

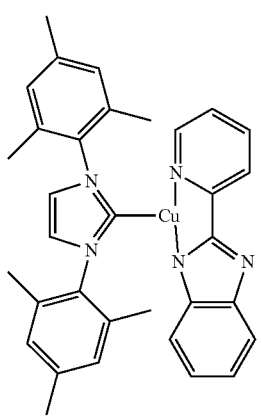

-continued

Complex 7

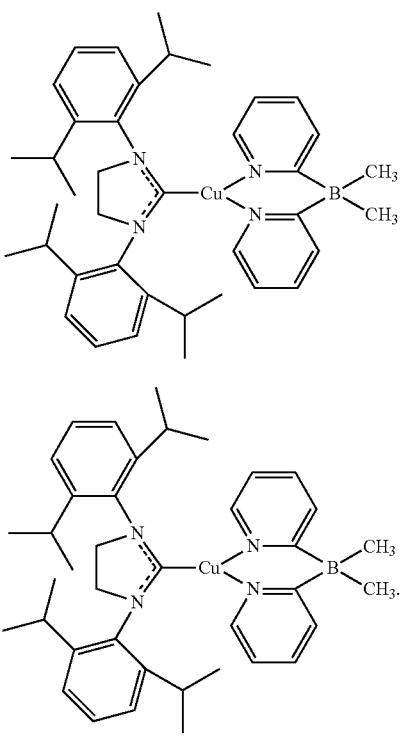

Complex 8

Preferably, the complex is selected from the group consisting of:

Complex 1

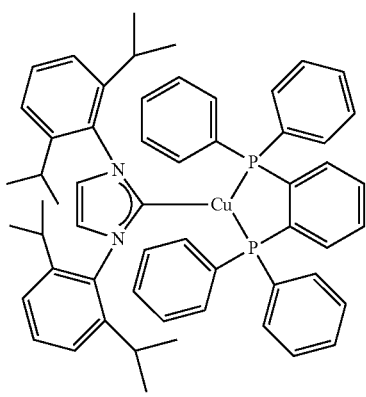

Complex 2

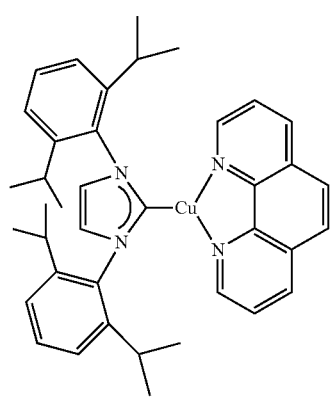

-continued

Complex 3

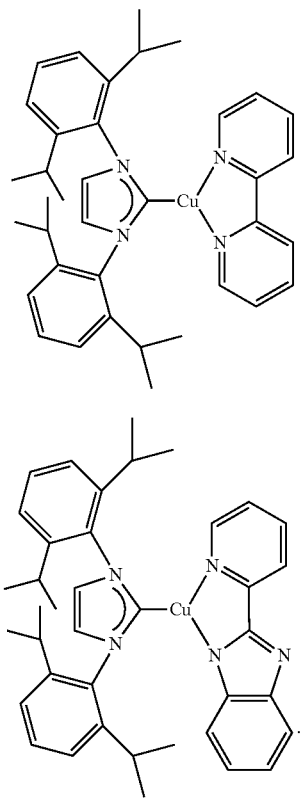

Complex 4

More preferably, the complex is:

Complex 4

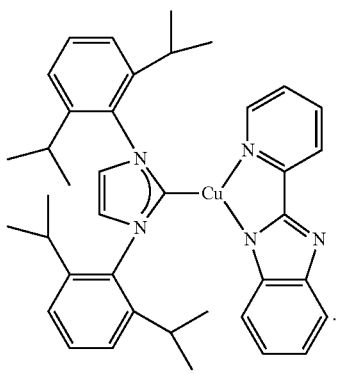

In another aspect, the complex has the formula:

Formula IV

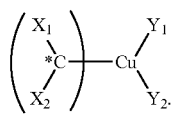

$Y_1$ and $Y_2$ are substituents that are independently selected from the group consisting of alkyl, heteroalkyl, aryl and heteroaryl. $Y_1$ and $Y_2$ may be further substituted. $Y_1$ and $Y_2$ are not joined. Each of $Y_1$ and $Y_2$ form a bond with Cu.

In one aspect, the complex is selected from the group consisting of:

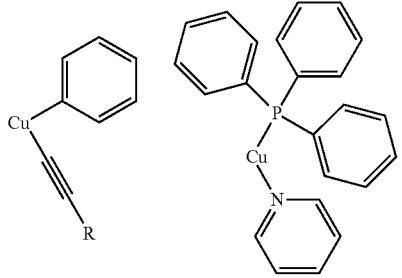

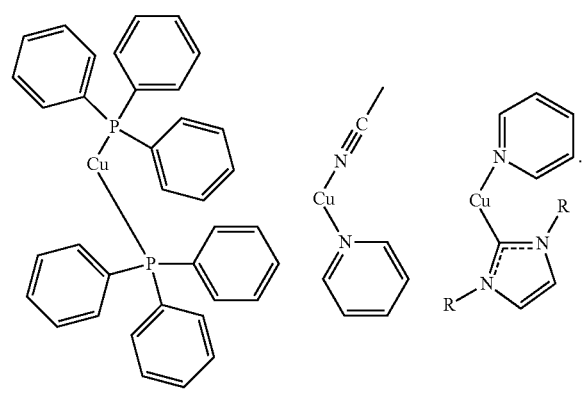

Each R is independently selected from the group consisting of hydrogen, alkyl, alkoxy, amino, alkenyl, alkynyl, arylalkyl, heteroalkyl, aryl and heteroaryl.

In another aspect, the carbene ligand is bidentate. Preferably, the complex is selected from the group consisting of:

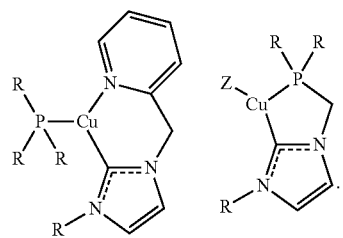

Each R is independently selected from the group consisting of hydrogen, alkyl, alkoxy, amino, alkenyl, alkynyl, arylalkyl, heteroalkyl, aryl and heteroaryl. Z is a monodentate ligand.

In one aspect, the complex is included in a polymer. In another aspect, the complex is included in the repeat unit of the polymer. In yet another aspect, the complex is pendant on the polymer. Preferably, the polymer is selected from the group consisting of:

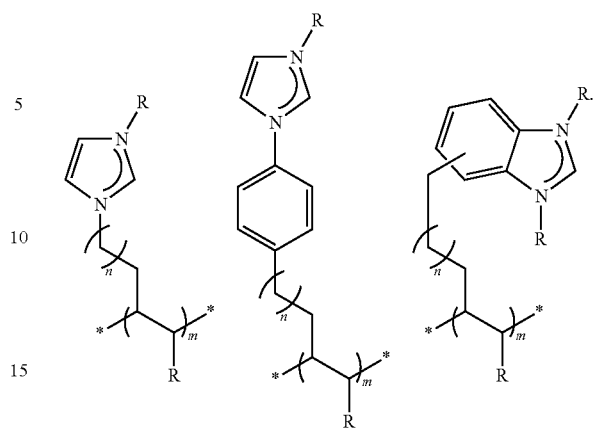

Each R is independently selected from the group consisting of hydrogen, alkyl, alkoxy, amino, alkenyl, alkynyl, arylalkyl, heteroalkyl, aryl and heteroaryl. m is greater than 2. n is 0-20.

In another aspect, the complex is included in a dendritic complex. Preferably, the dendritic complex is

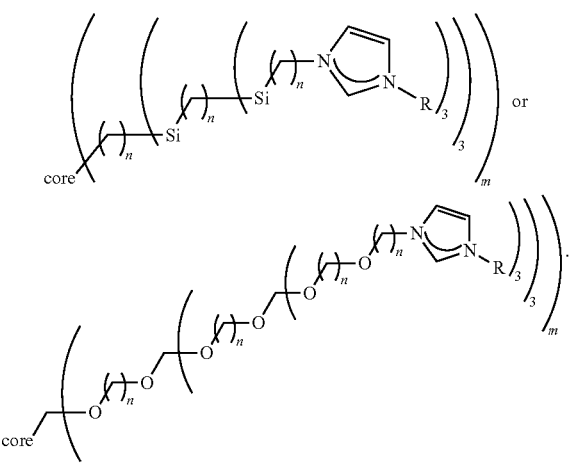

The core is a molecule or a polyvalent element selected from the group consisting of C, Si, Ge, Sn, Pb, N, P, and As. Each R is independently selected from the group consisting of hydrogen, alkyl, alkoxy, amino, alkenyl, alkynyl, arylalkyl, heteroalkyl, aryl and heteroaryl. m is greater than 1. n is 0-20.

In yet another aspect, the complex is included in a small molecule.

Devices comprising the phosphorescent complexes are also provided. A first device comprising an organic light emitting device further comprising an anode, a cathode; and an organic layer, disposed between the anode and the cathode. The organic layer further comprising a phosphorescent complex itself comprising a three coordinate copper atom and a carbene ligand. Preferably, the first device is a consumer product. The device may comprise a complex having Formula I, Formula II, Formula III, or Formula IV, as described above. Selections for the substituents, ligands, and complexes described as preferred for the complexes having Formula I, Formula II, Formula III, or Formula IV are also preferred for use in a device that comprises a complex including a complex having Formula I, Formula II, Formula III, or Formula IV. These selections include those described for $X_1$, $X_2$, $X'_1$, $X'_2$, $Y_1$, $Y_2$, $Y'_1$, $Y'_2$, Yi, R, X, and Z.

Selections for the substituents, ligands, and complexes described as preferred for the complexes having Formula I, Formula II, Formula III, or Formula IV are also preferred for use in a device that comprises a complex including a complex having Formula I, Formula II, Formula III, or Formula IV. These selections include those described for $X_1$, $X_2$, $X'_1$, $X'_2$, $Y_1$, $Y_2$, $Y_3$, $Y_4$, $Y_5$, $Y'_1$, $Y'''_1$, $Y'_2$, $Y_i$, R, X, and Z.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
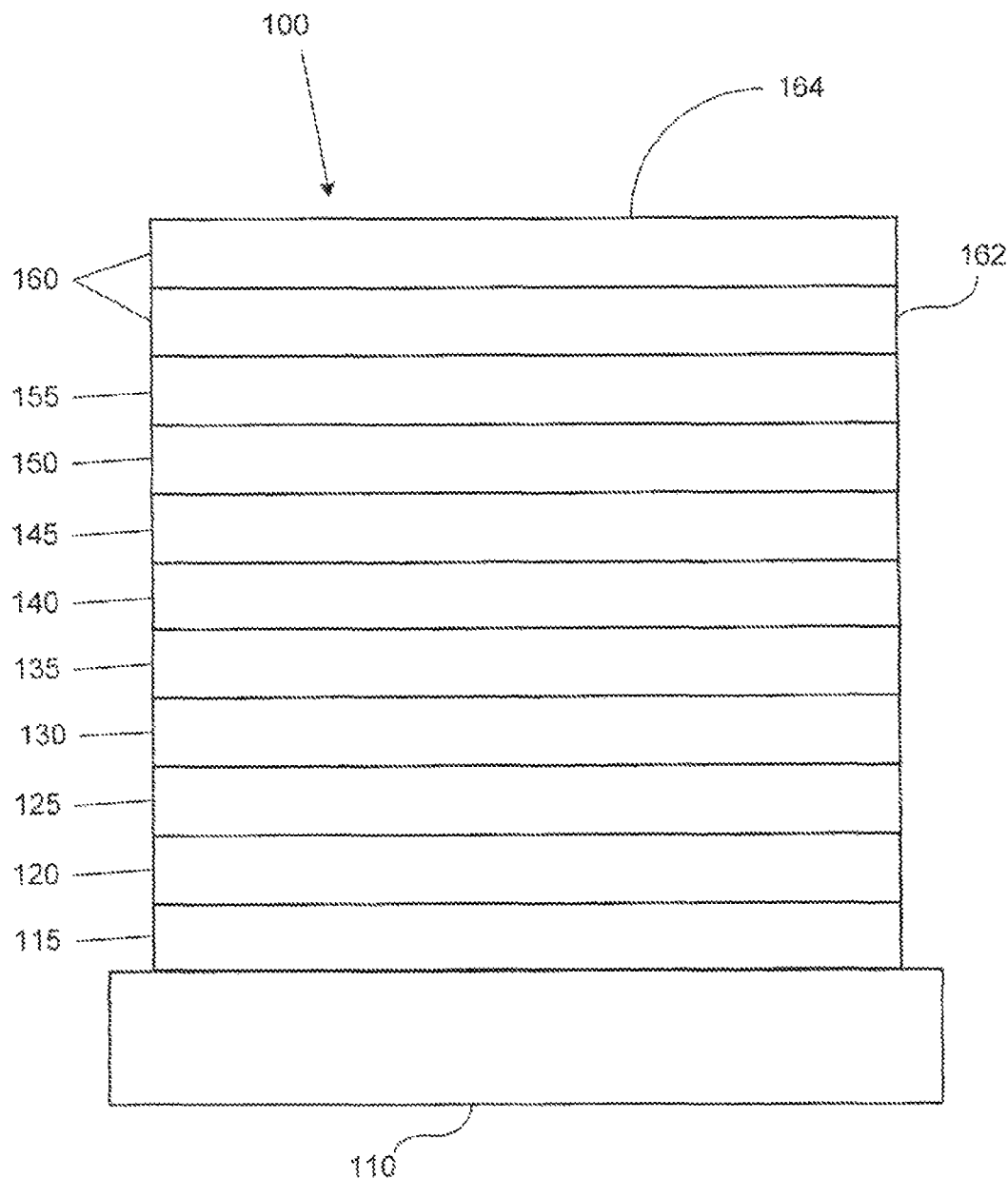
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a complex cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including complex cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
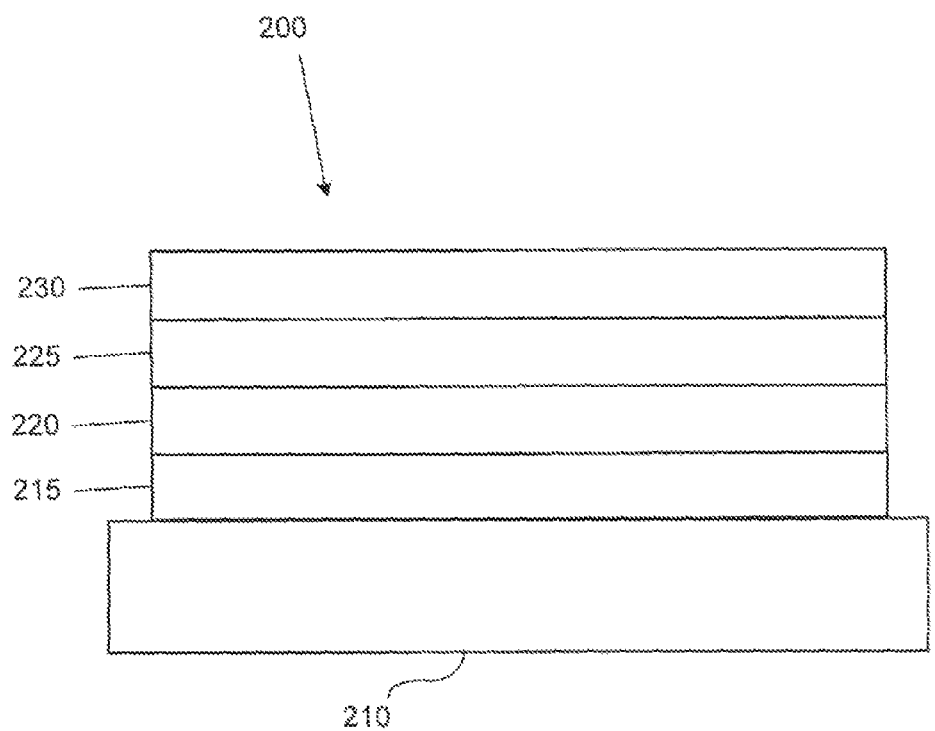
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
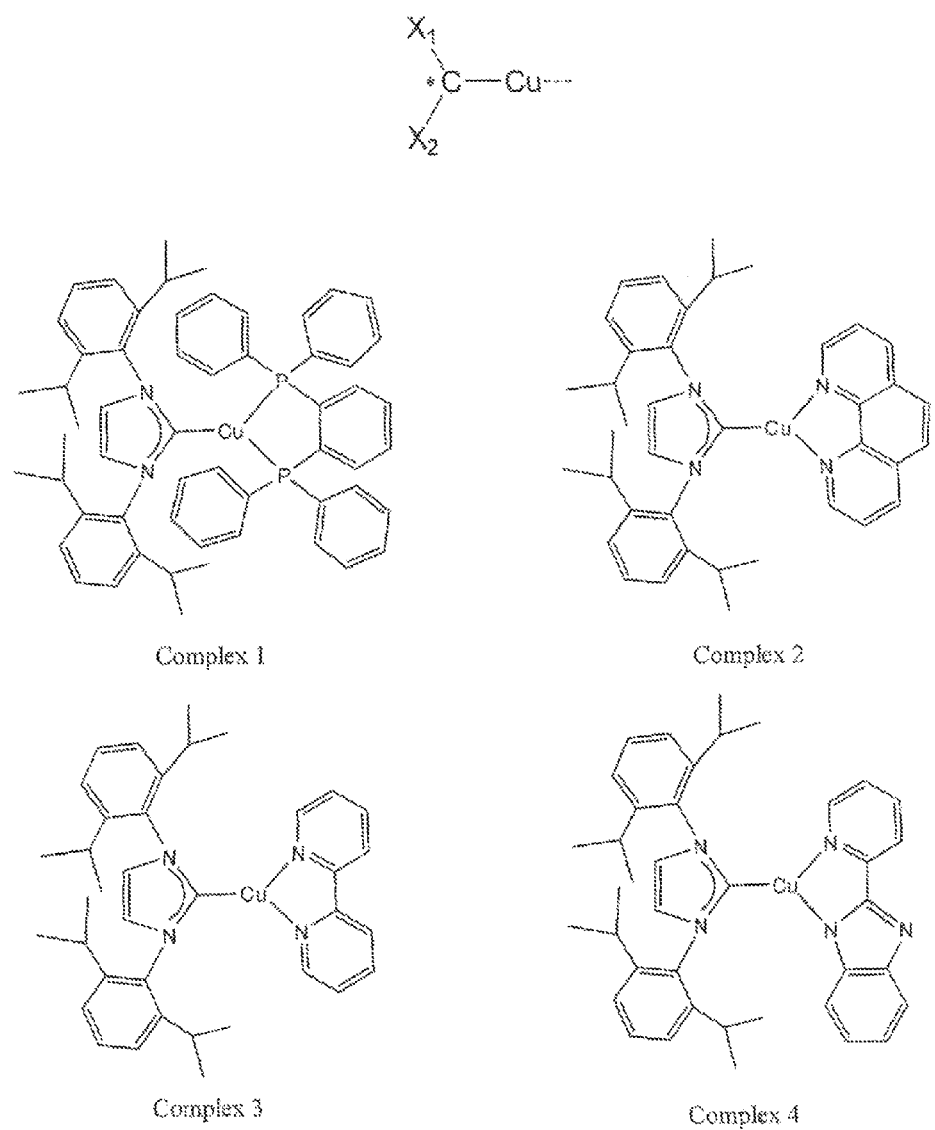
FIG. 3 shows complexes comprising a carbene ligand coordinated to a three coordinate copper atom.
Figure 4:
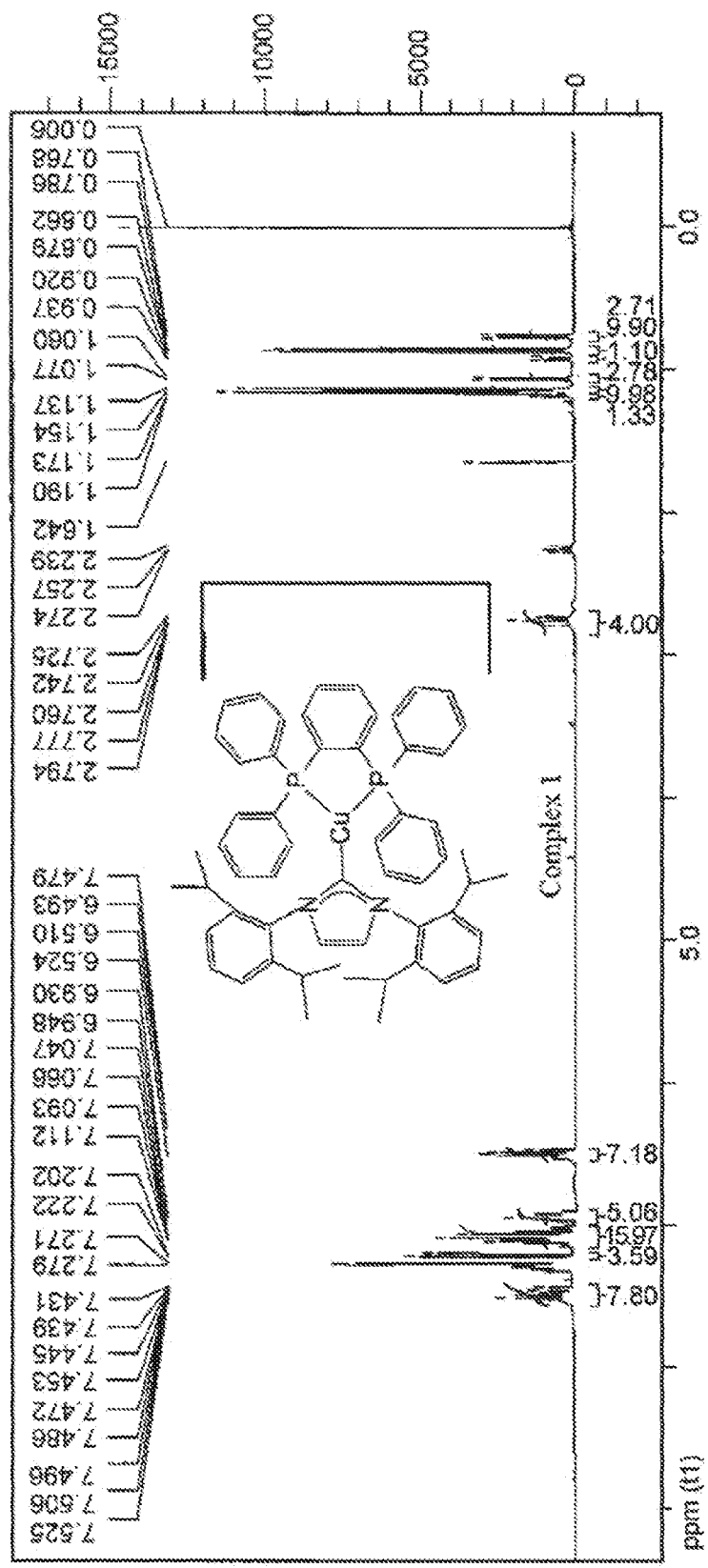
FIG. 4 shows $^1$H-NMR spectrum of Complex 1.
Figure 5:
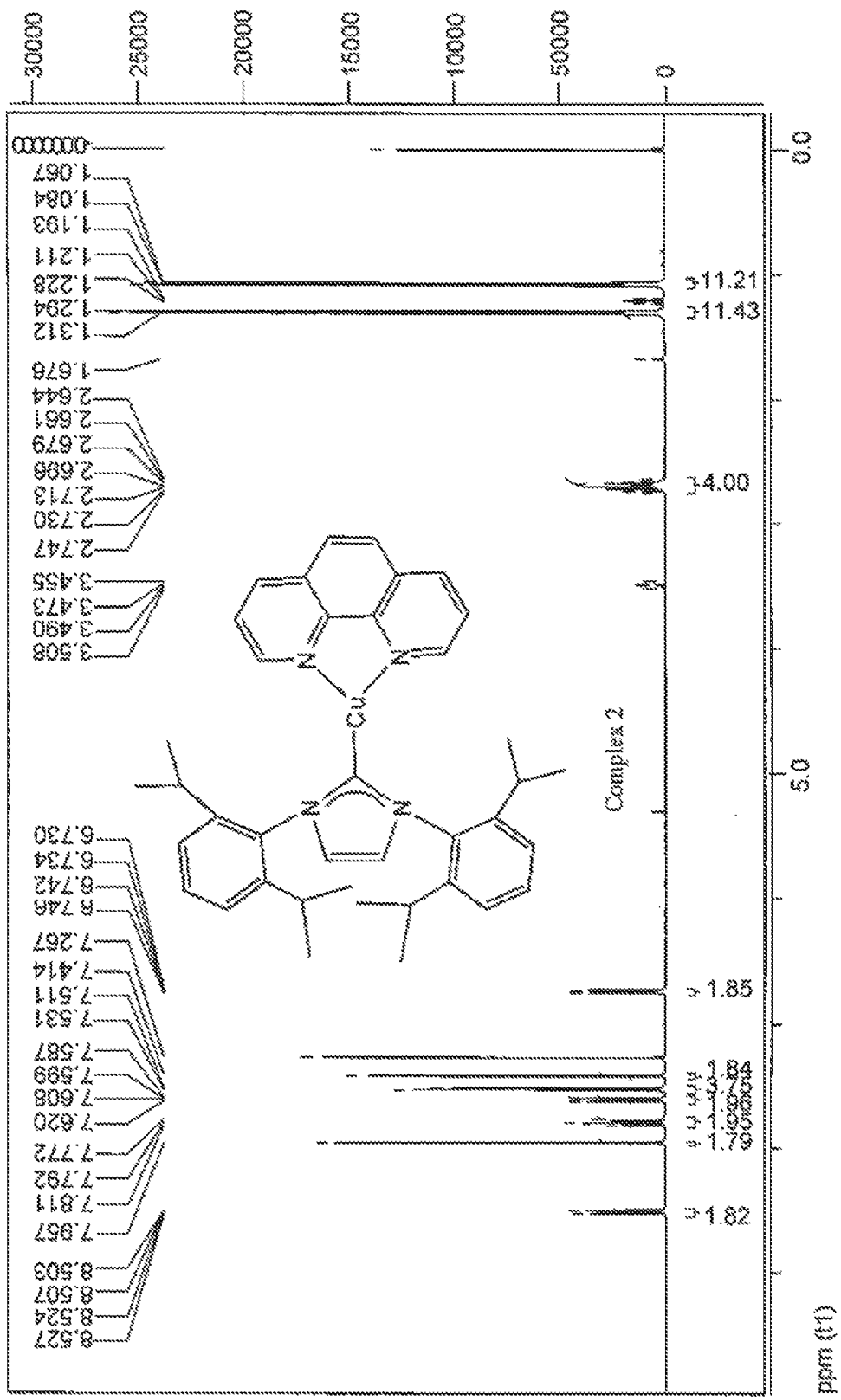
FIG. 5 shows $^1$H-NMR spectrum of Complex 2.
Figure 6:
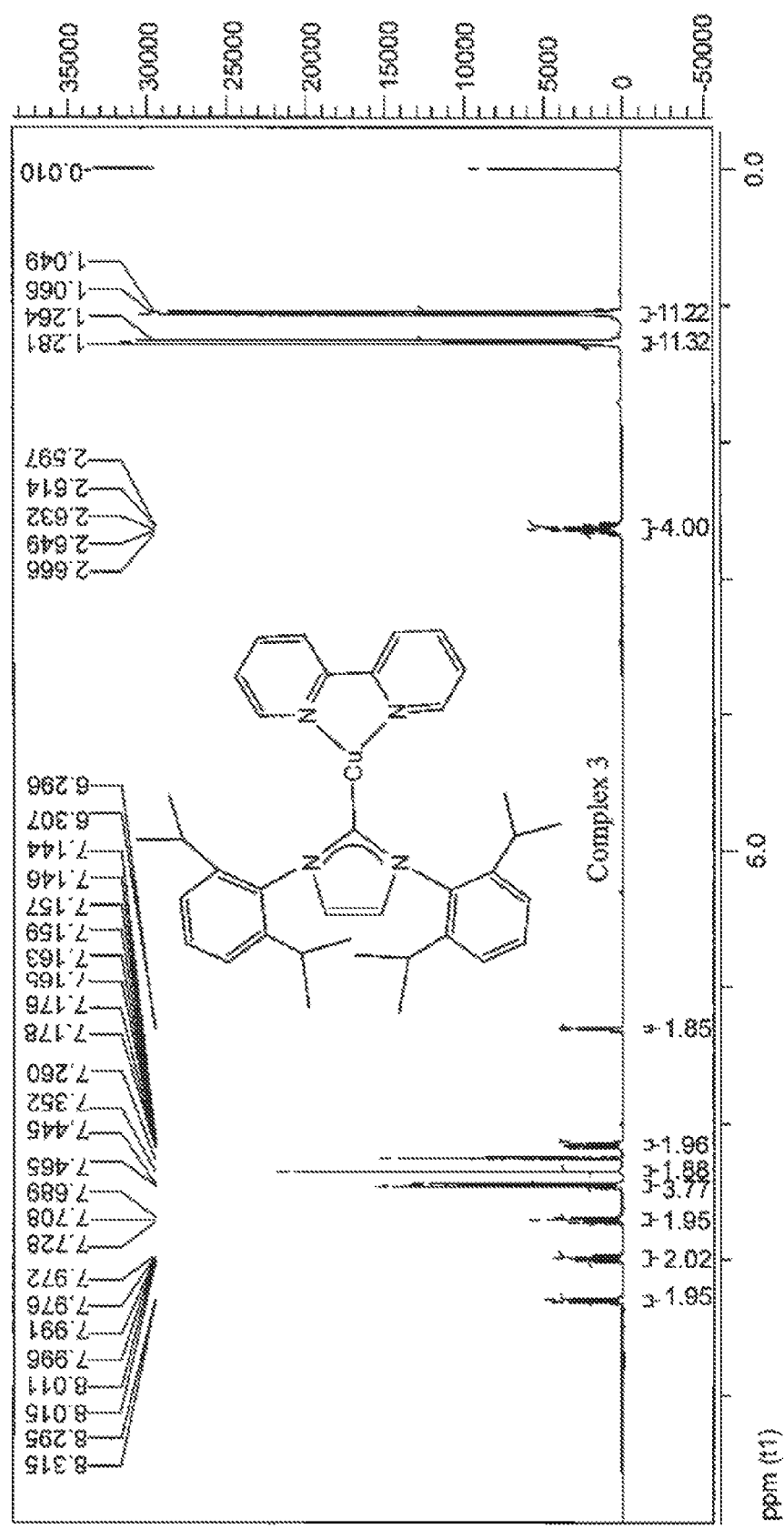
FIG. 6 shows $^1$H-NMR spectrum of Complex 3.
Figure 7:
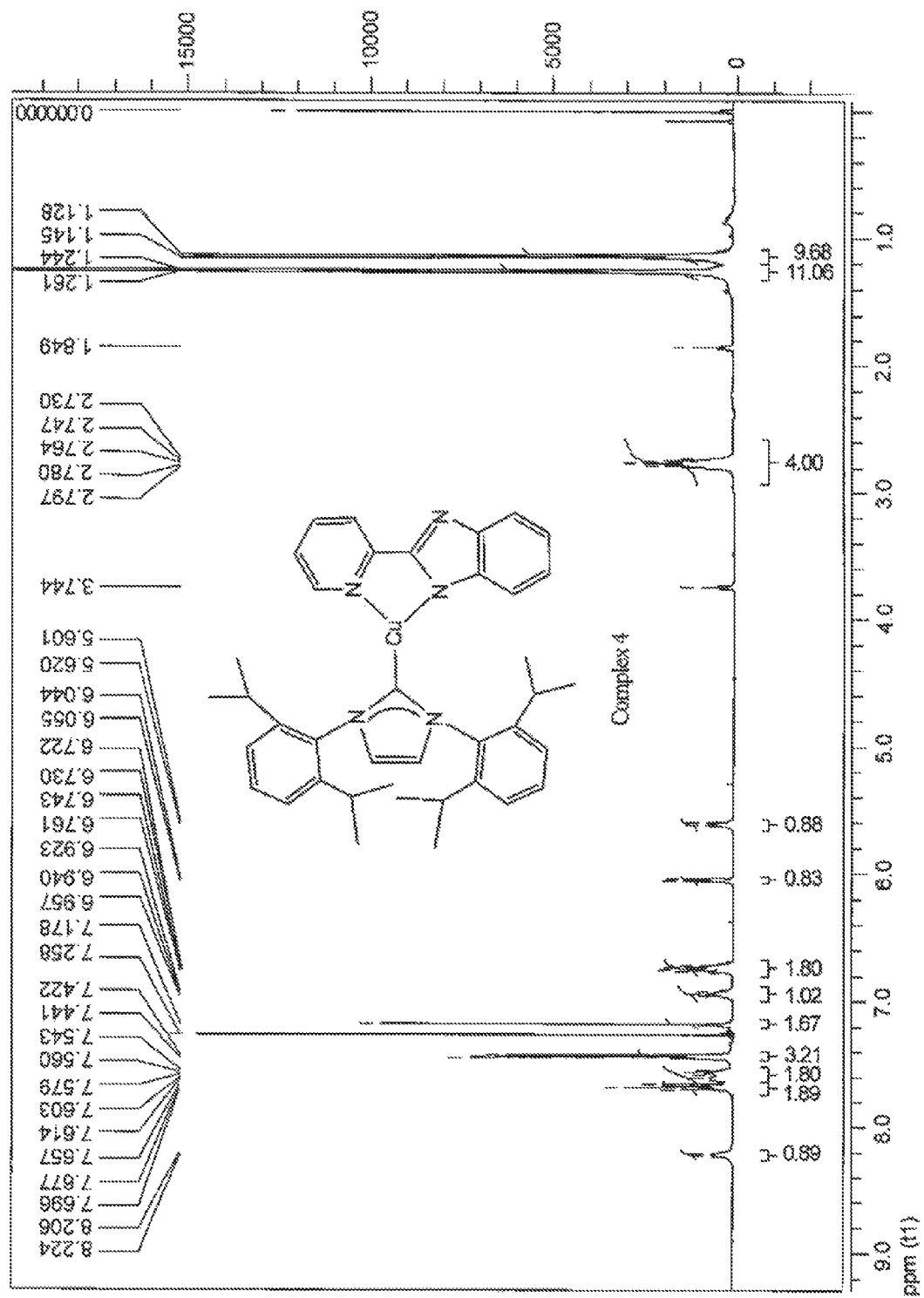
FIG. 7 shows $^1$H-NMR spectrum of Complex 4.
Figure 8:
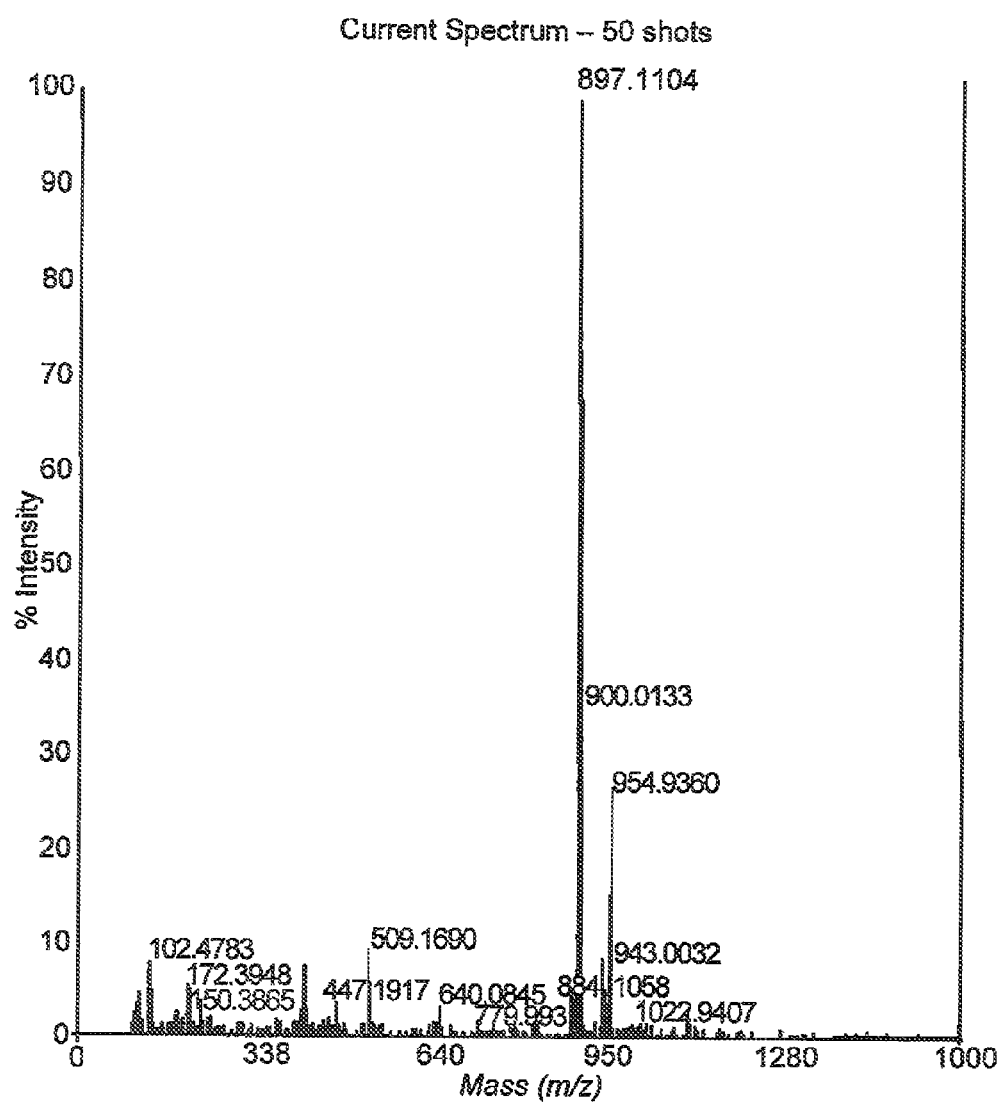
FIG. 8 shows MALDI spectrum of Complex 1.
Figure 9:
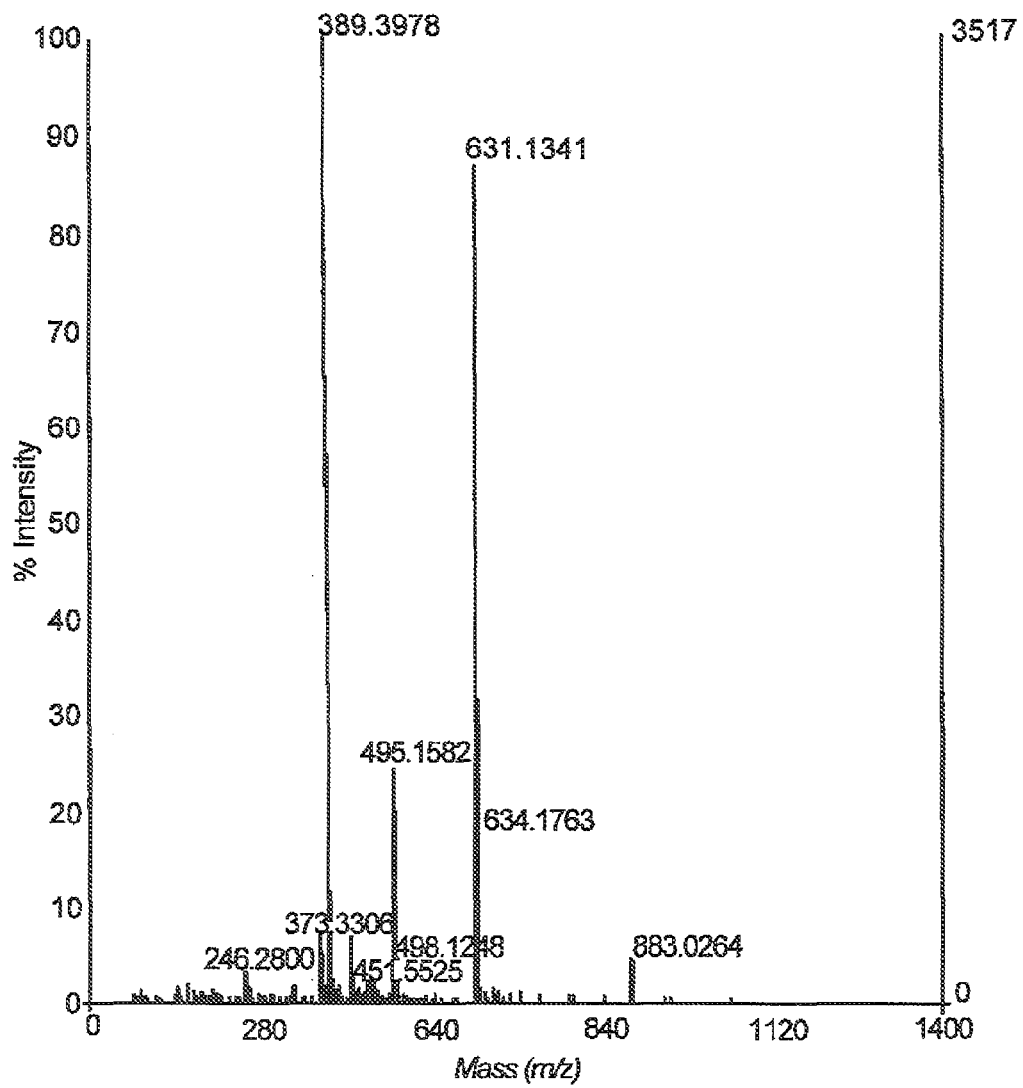
FIG. 9 shows MALDI spectrum of Complex 2.
Figure 10:
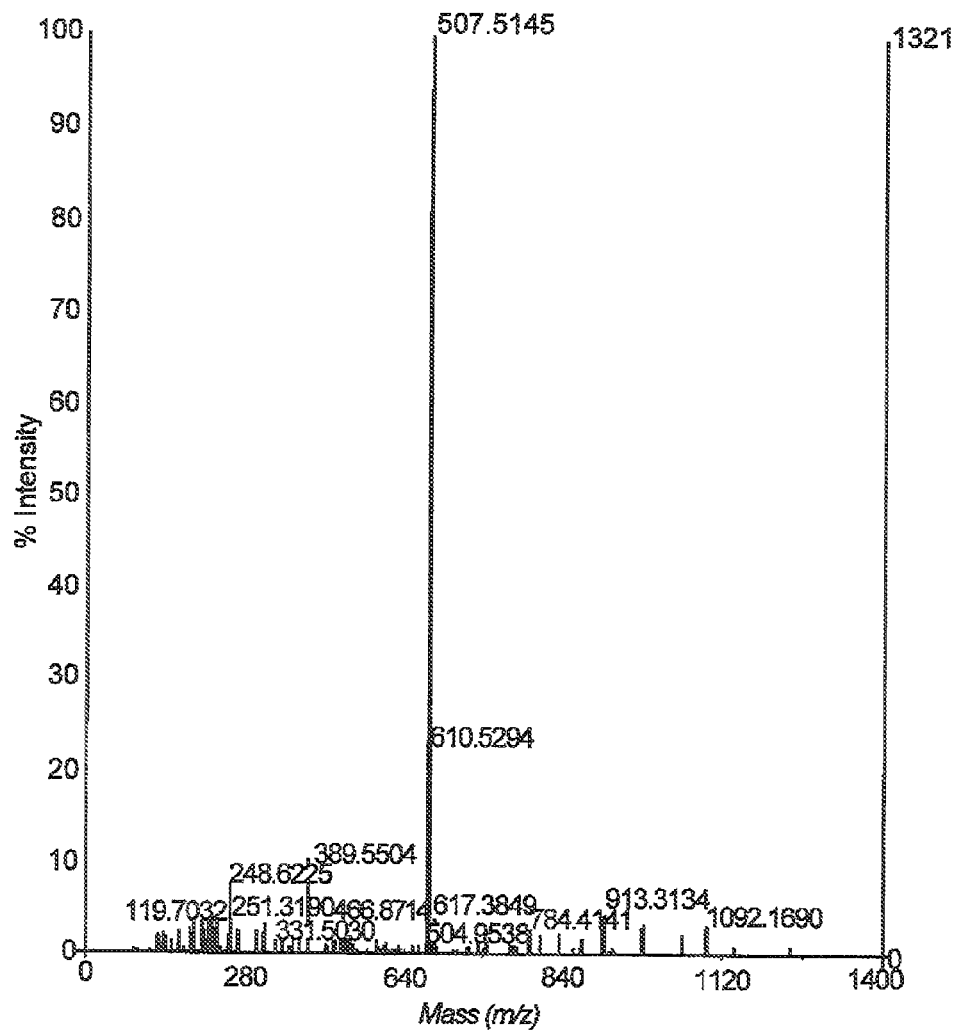
FIG. 10 shows MALDI spectrum of Complex 3.
Figure 11:
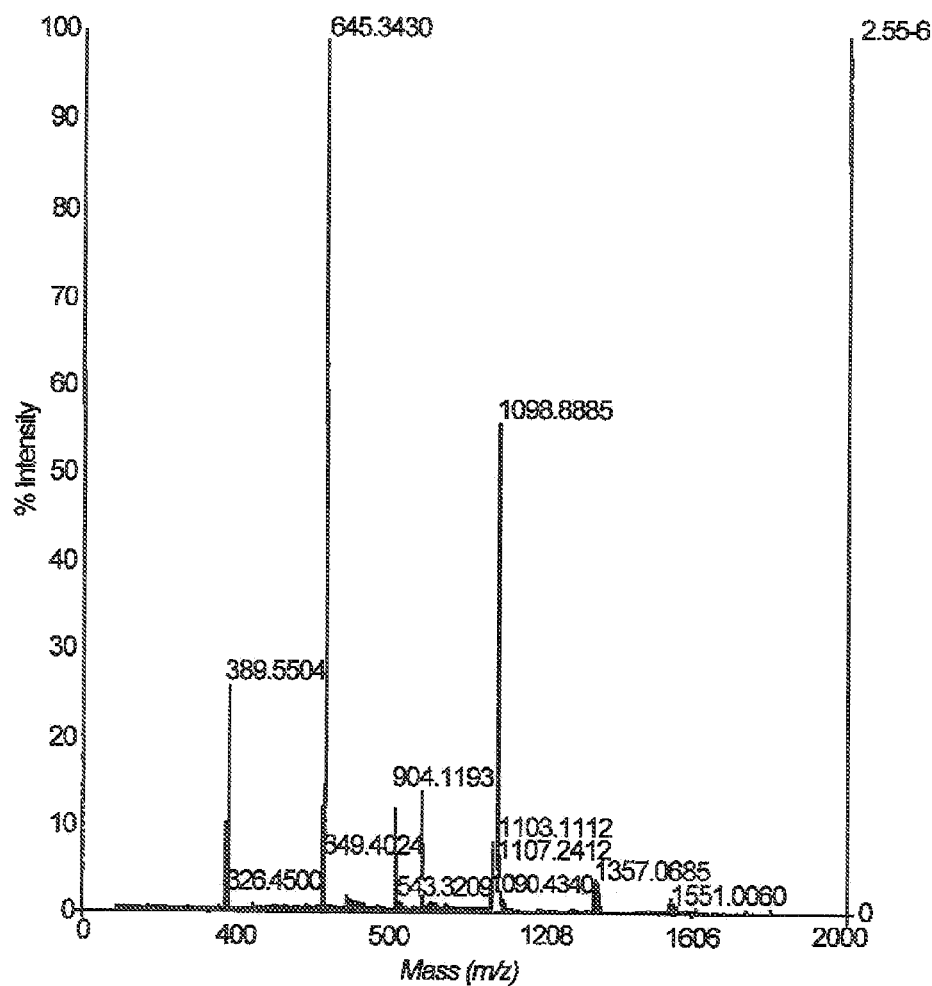
FIG. 11 shows MALDI spectrum of Complex 4.
Figure 12:
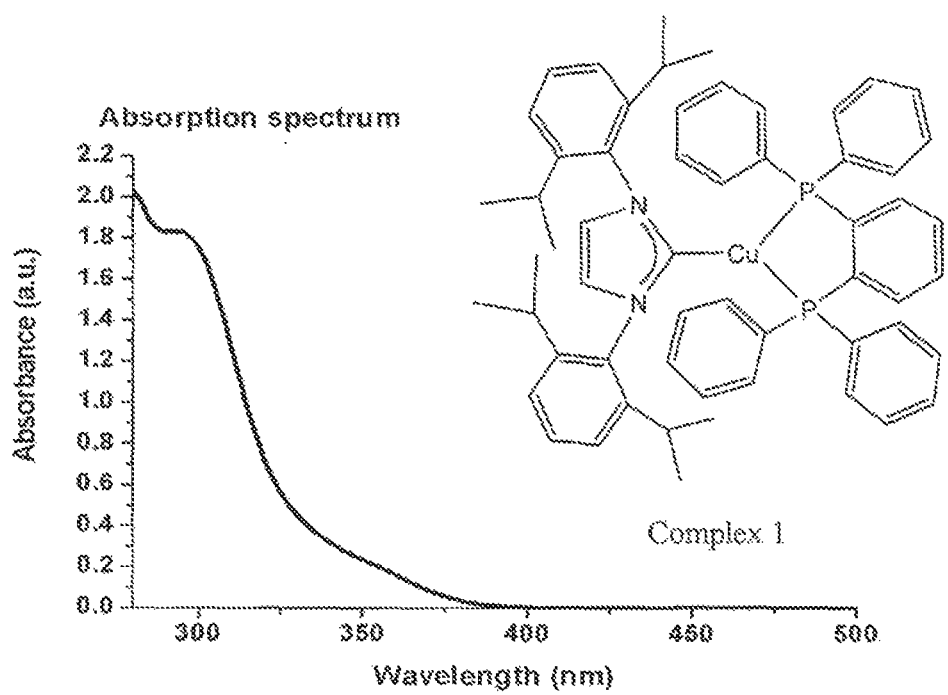
FIG. 12 shows the absorption spectrum of Complex 1.
Figure 13:
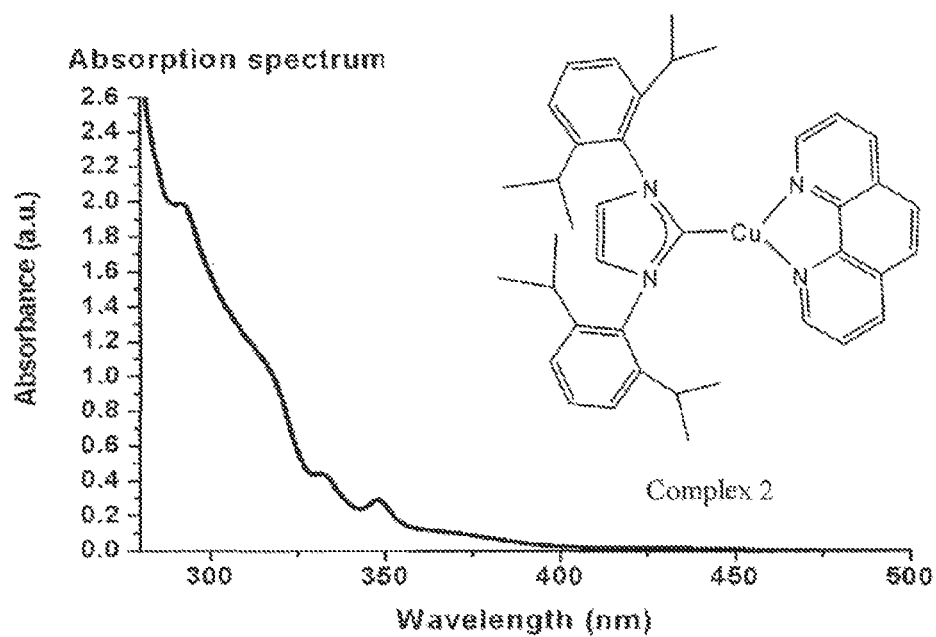
FIG. 13 shows the absorption spectrum of Complex 2.
Figure 14:
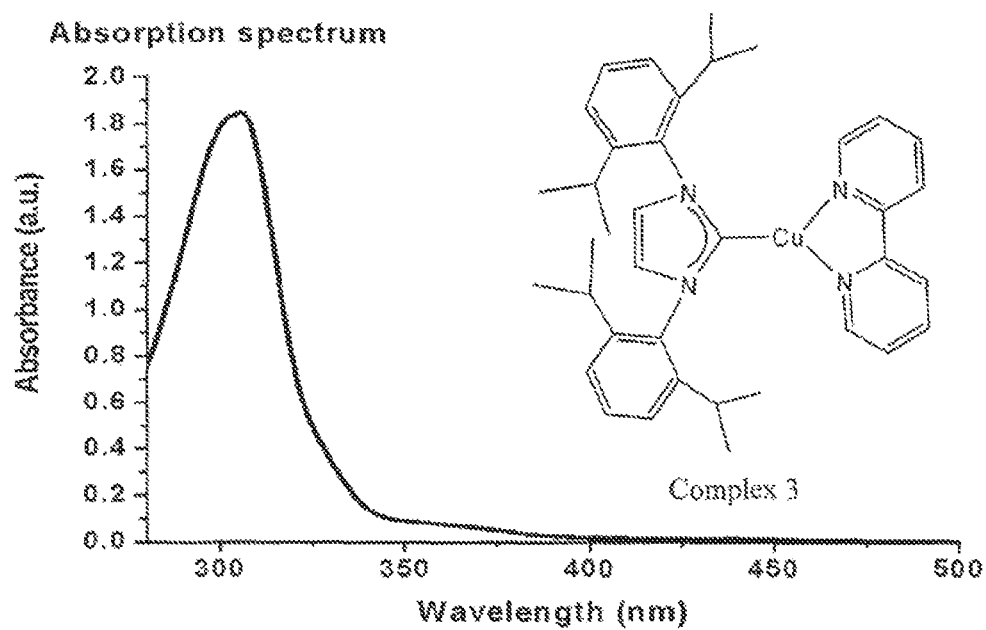
FIG. 14 shows the absorption spectrum of Complex 3.
Figure 15:
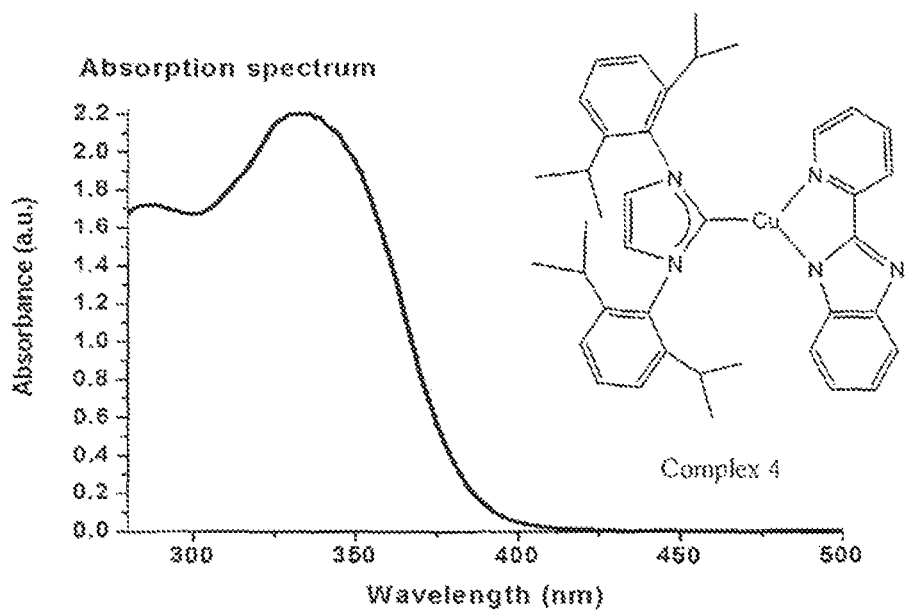
FIG. 15 shows the absorption spectrum of Complex 4.
Figure 16:
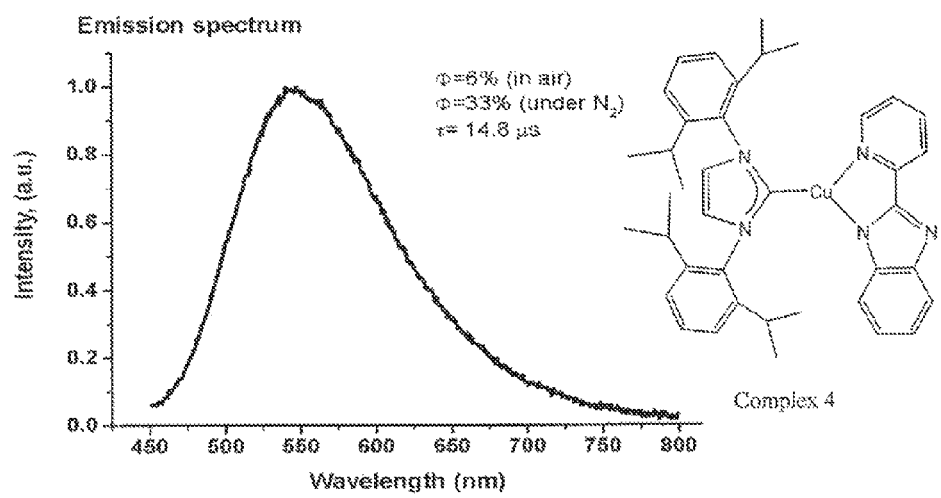
FIG. 16A shows absorption spectrum of Complex 4.
FIG. 16B shows the emission spectra of Complex 4.
Figure 16:
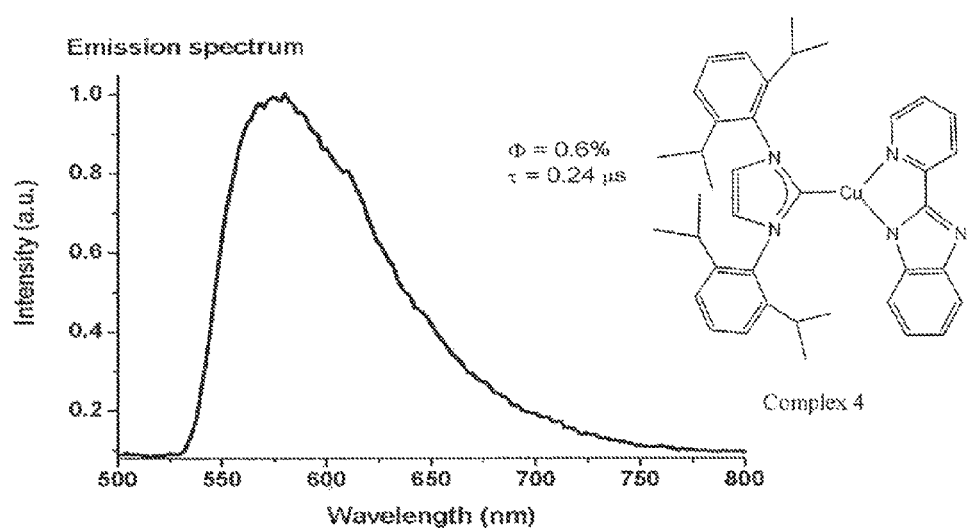
Figure 17:
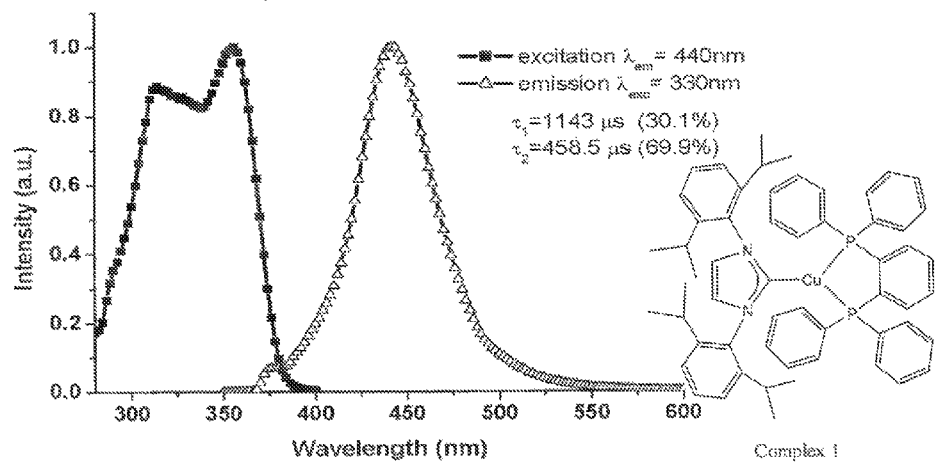
FIG. 17A shows excitation and emission spectra of Complex 1.
FIG. 17B shows excitation and emission spectra of Complex 2.
Figure 17:
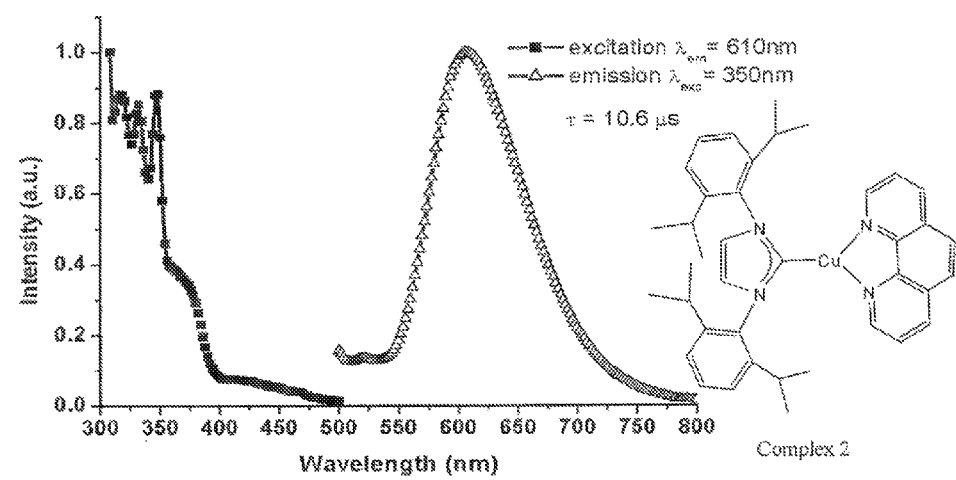
Figure 18:
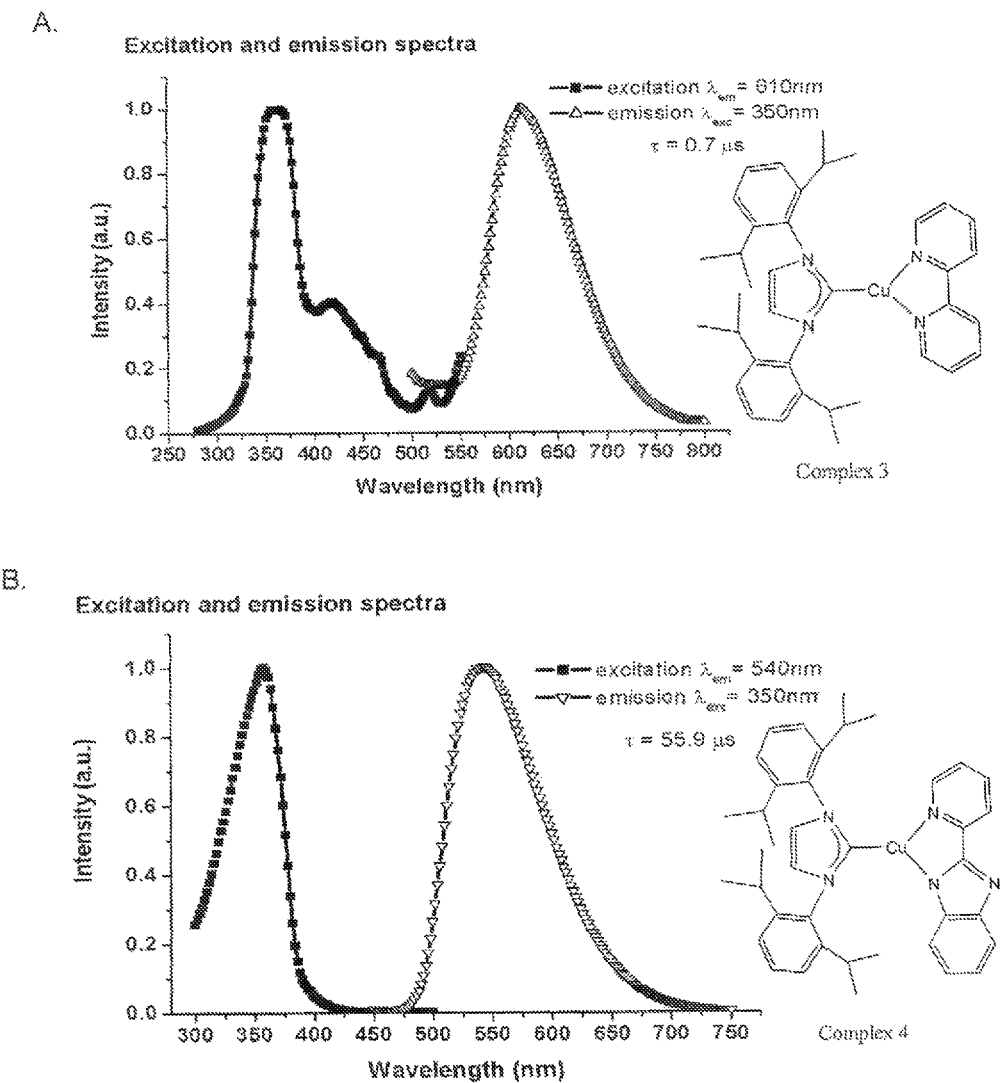
FIG. 18A shows excitation and emission spectra of Complex 3.
FIG. 18B shows excitation and emission spectra of Complex 4.
Figure 19:
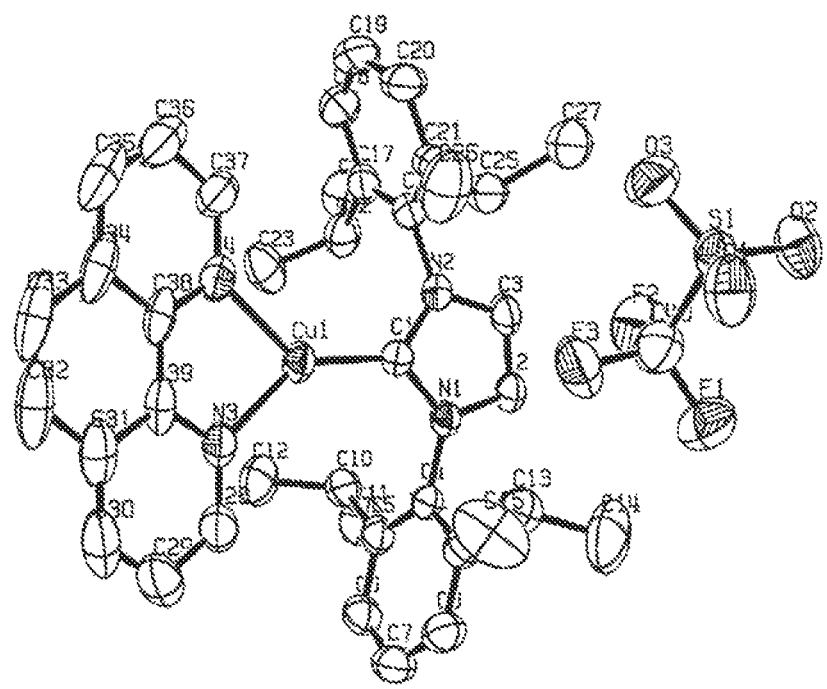
FIG. 19A shows the x-ray structure of Complex 2.
FIG. 19B shows the x-ray structure of Complex 4.
Figure 20:
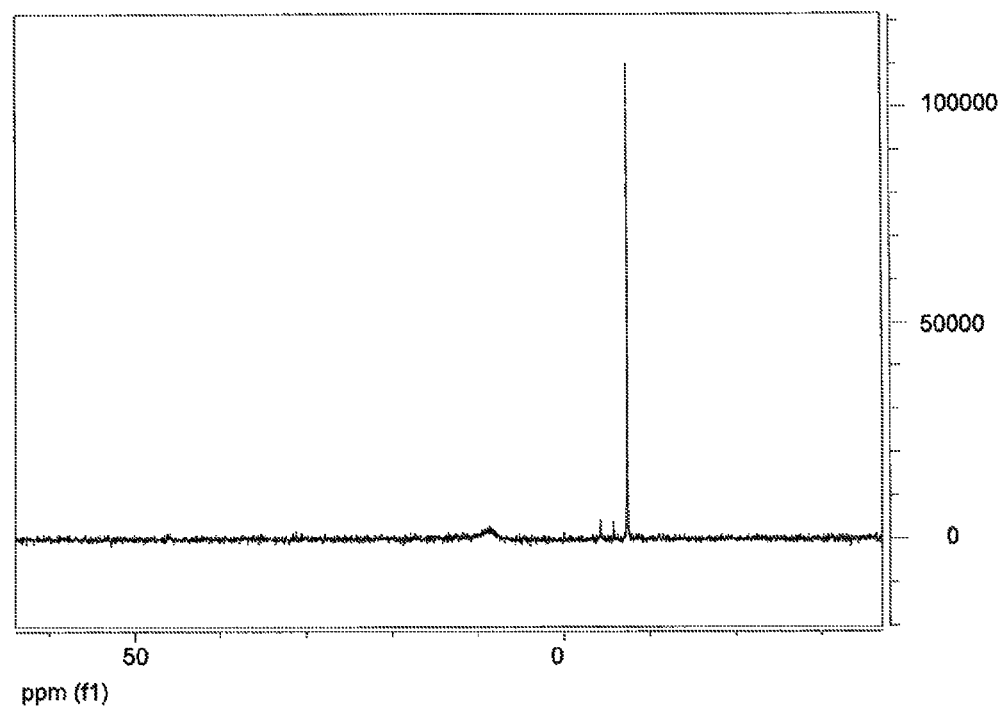
FIG. 20 shows the $^{31}$P-NMR spectrum of Complex 1.
Figure 21:
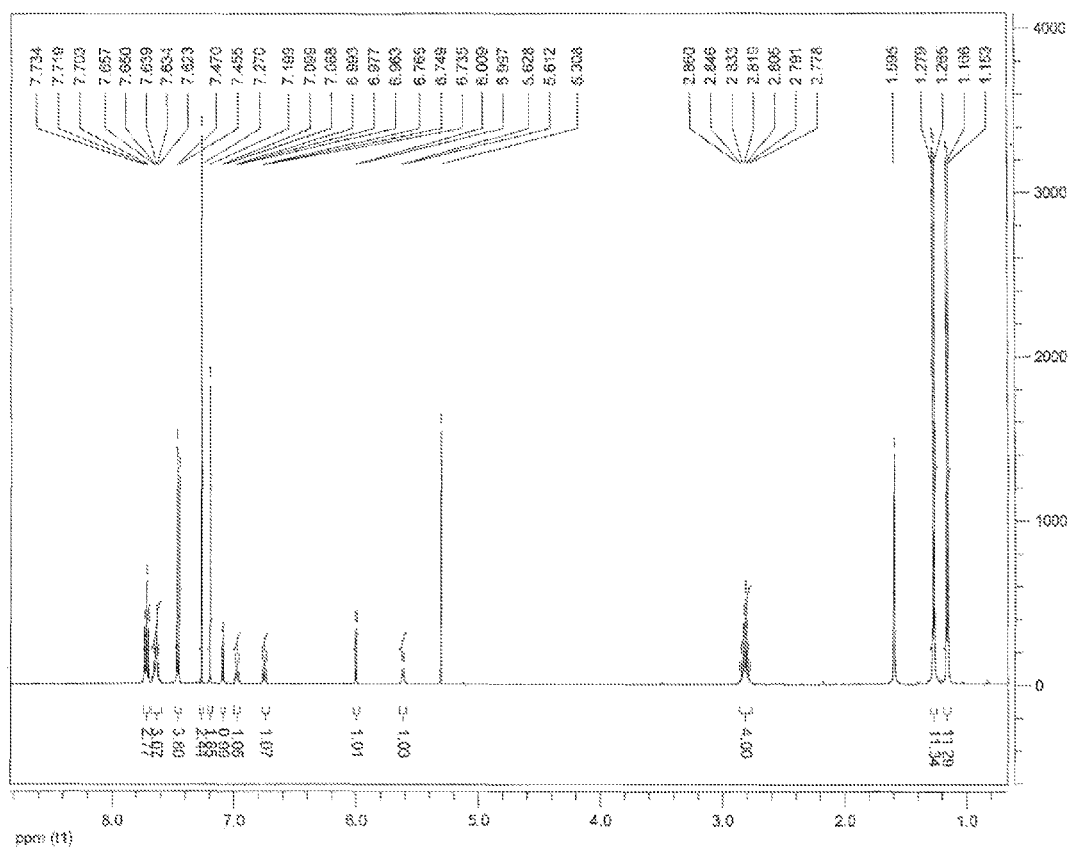
FIG. 21. shows the $^1$H-NMR spectrum of Complex 5.
Figure 22:
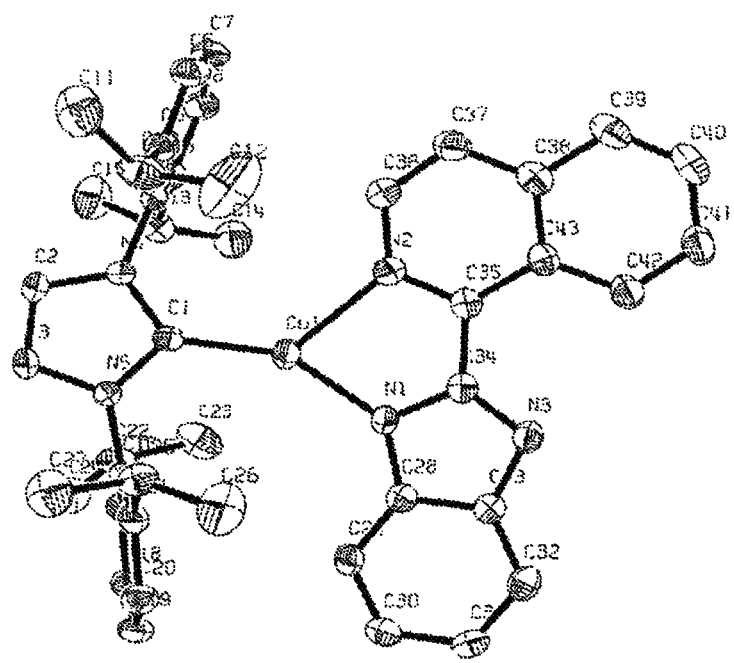
FIG. 22 shows the X-ray structure of Complex 5.
Figure 23:
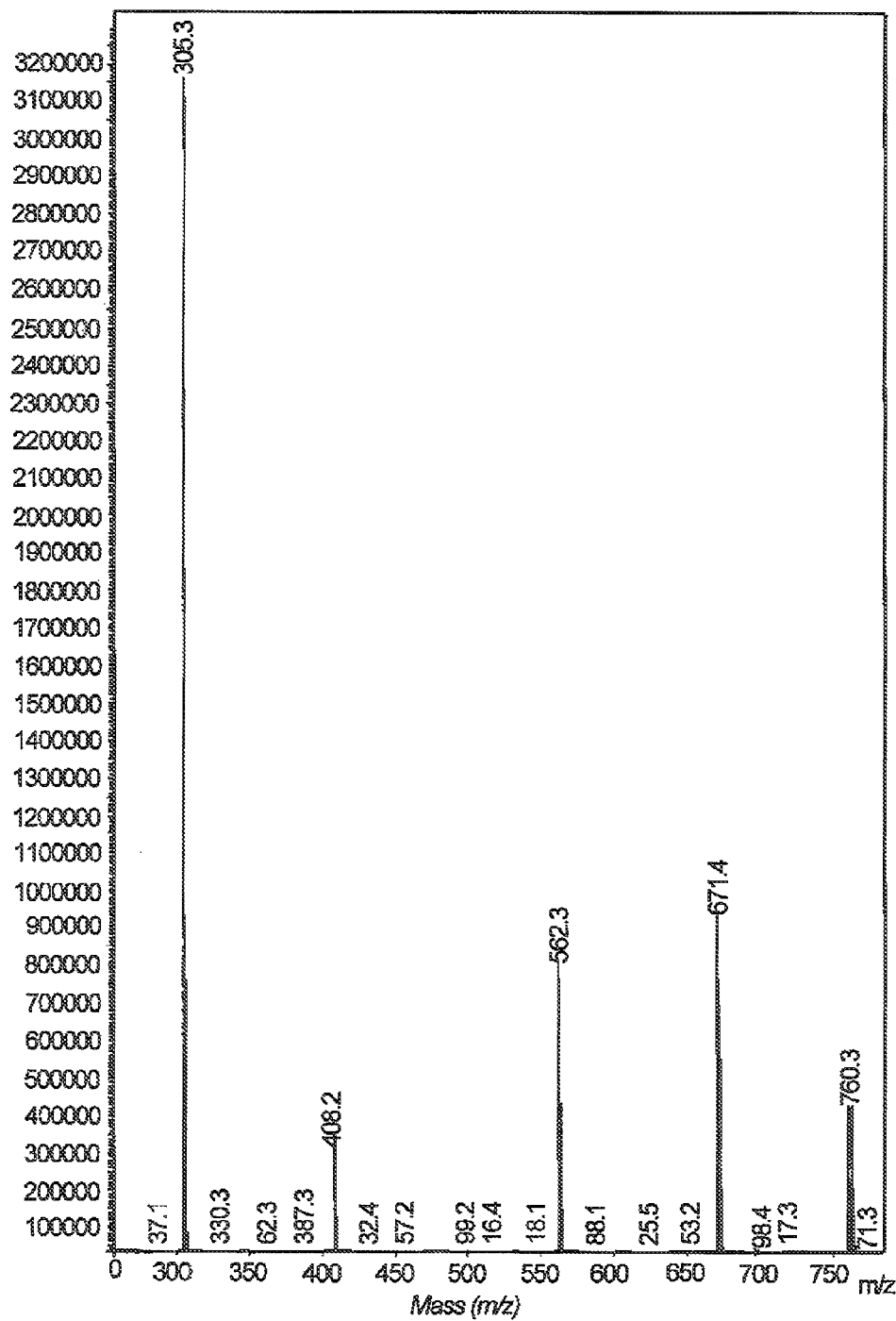
FIG. 23 shows LCMS spectrum of Complex 6.
Figure 24:
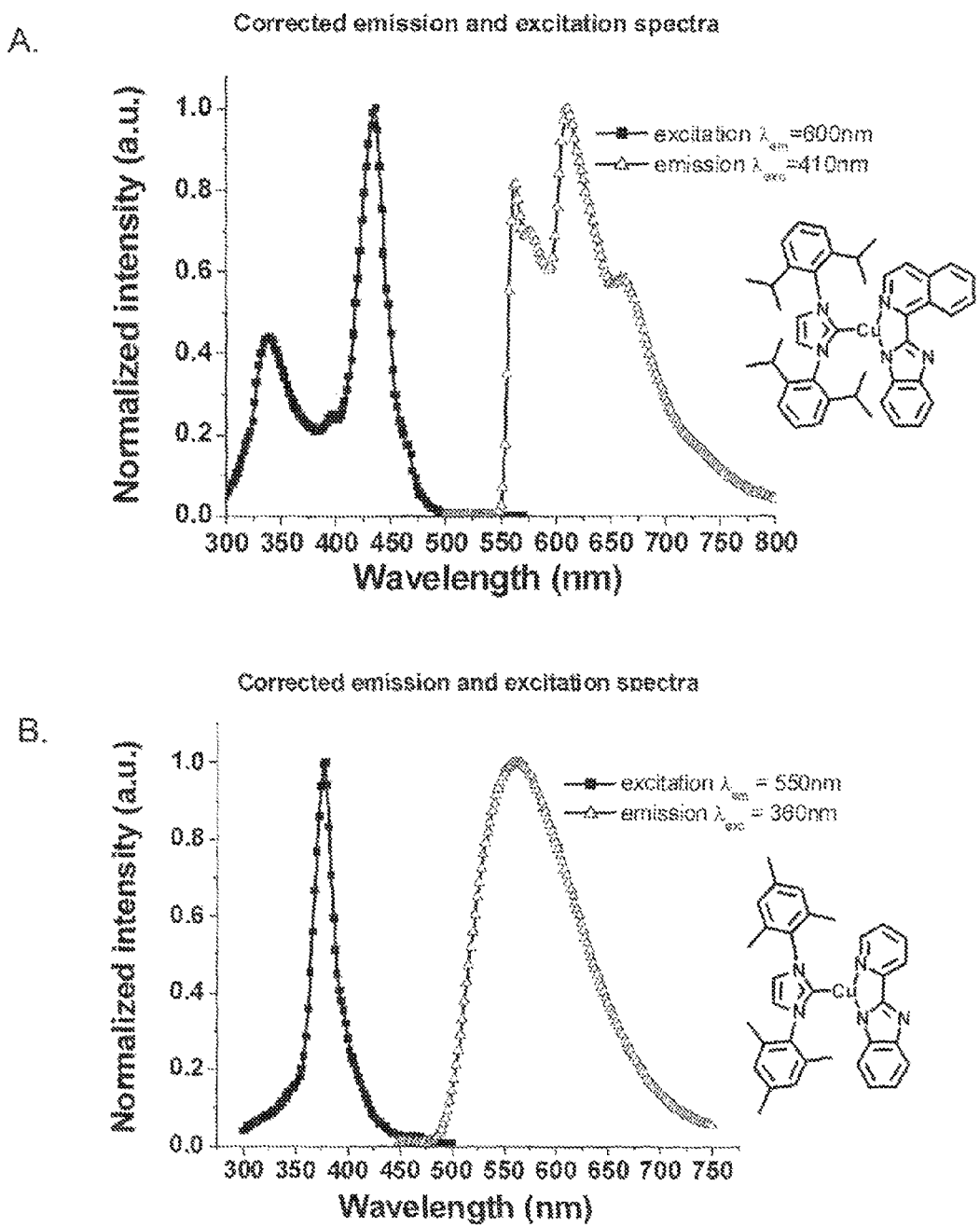
FIG. 24A shows corrected emission and excitation spectra of Complex 5 in 2MeTHF at 77K.
FIG. 24B shows corrected emission and excitation spectra of Complex 6 in 2MeTHF at 77K.
Figure 25:
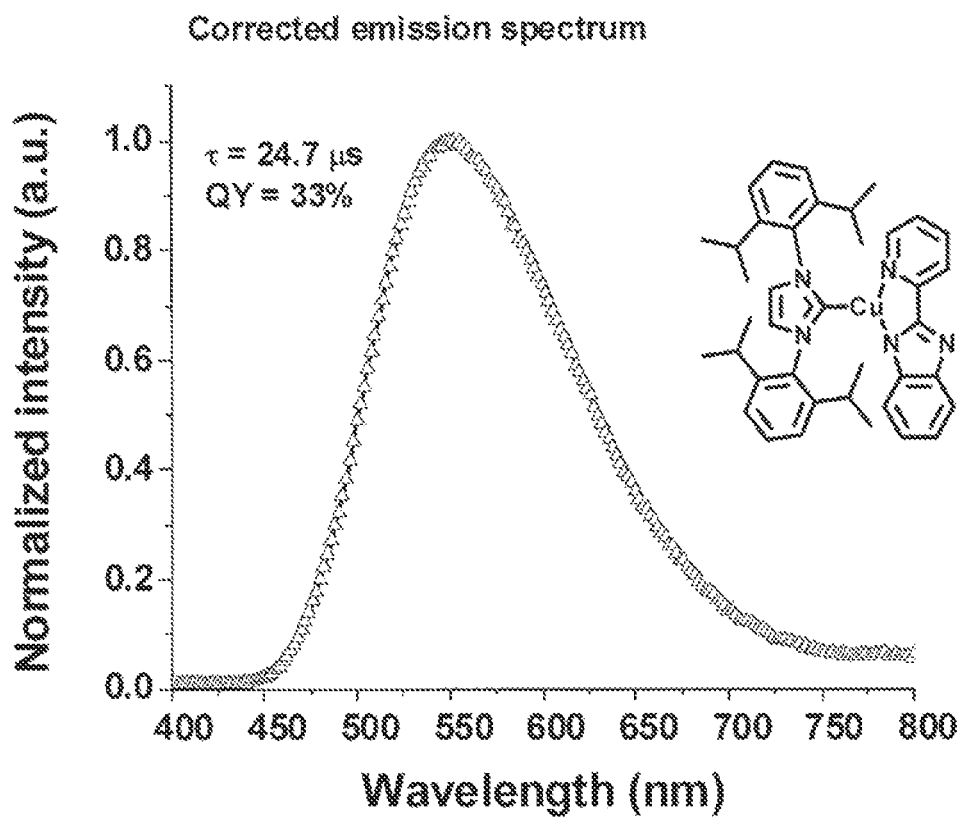
FIG. 25 shows a corrected emission spectrum of Complex 4 in PMMA film at room temperature.
Figure 26:
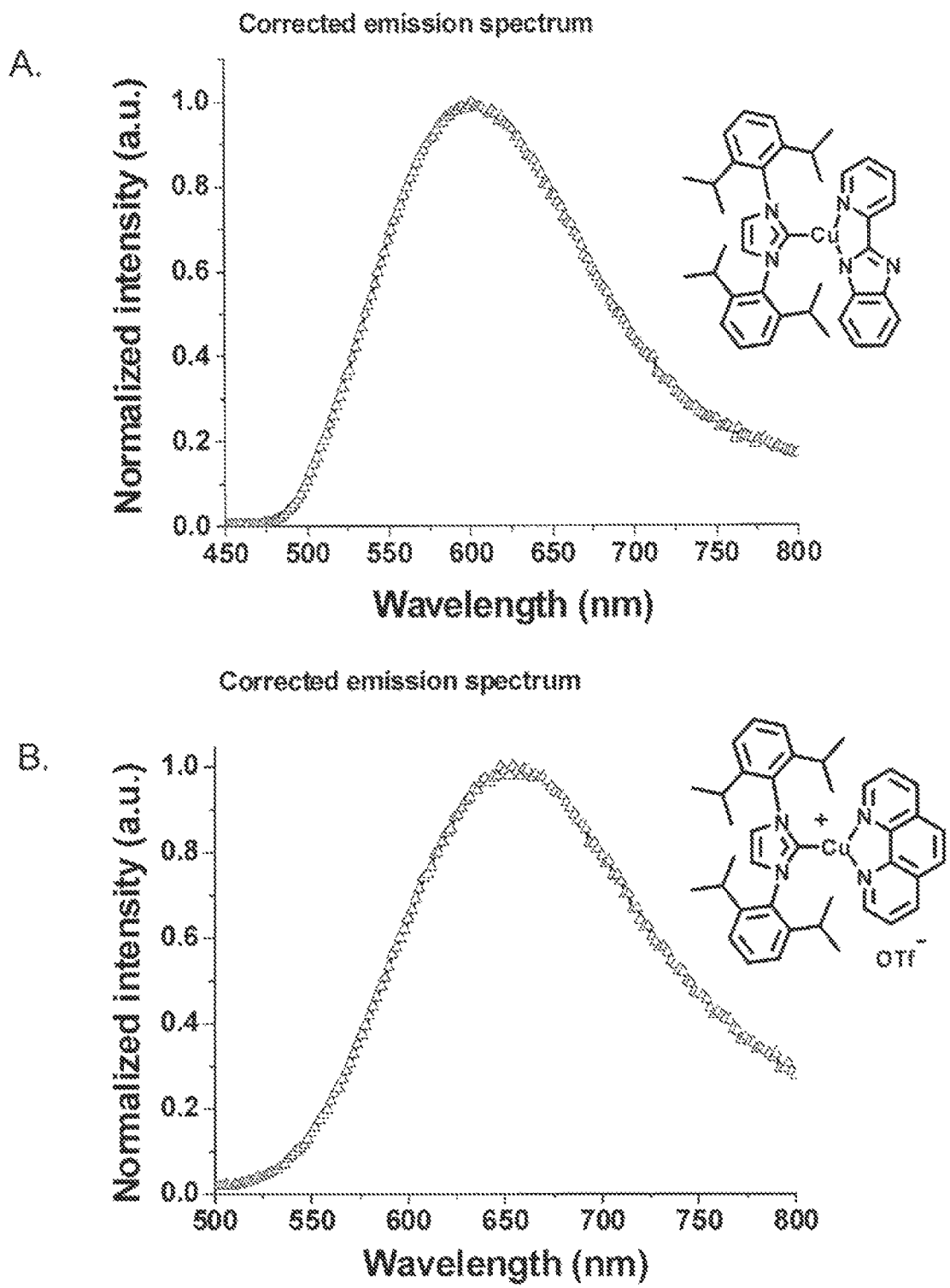
FIG. 26A shows a corrected emission spectrum of Complex 4 in $CH_2Cl_2$ at room temperature.
FIG. 26B shows a corrected emission spectrum of Complex 2 in $CH_2Cl_2$ at room temperature.
Figure 27:
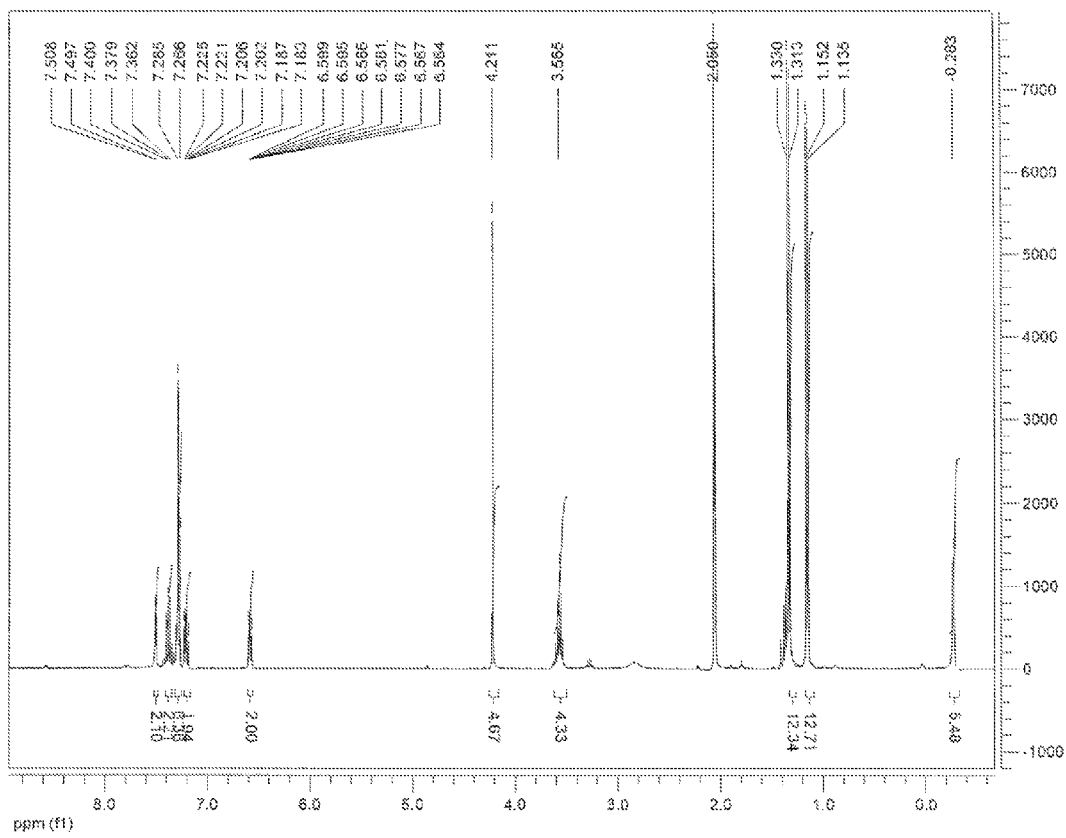
FIG. 27 shows $^1$H-NMR spectrum of Complex 7.
Figure 28A:
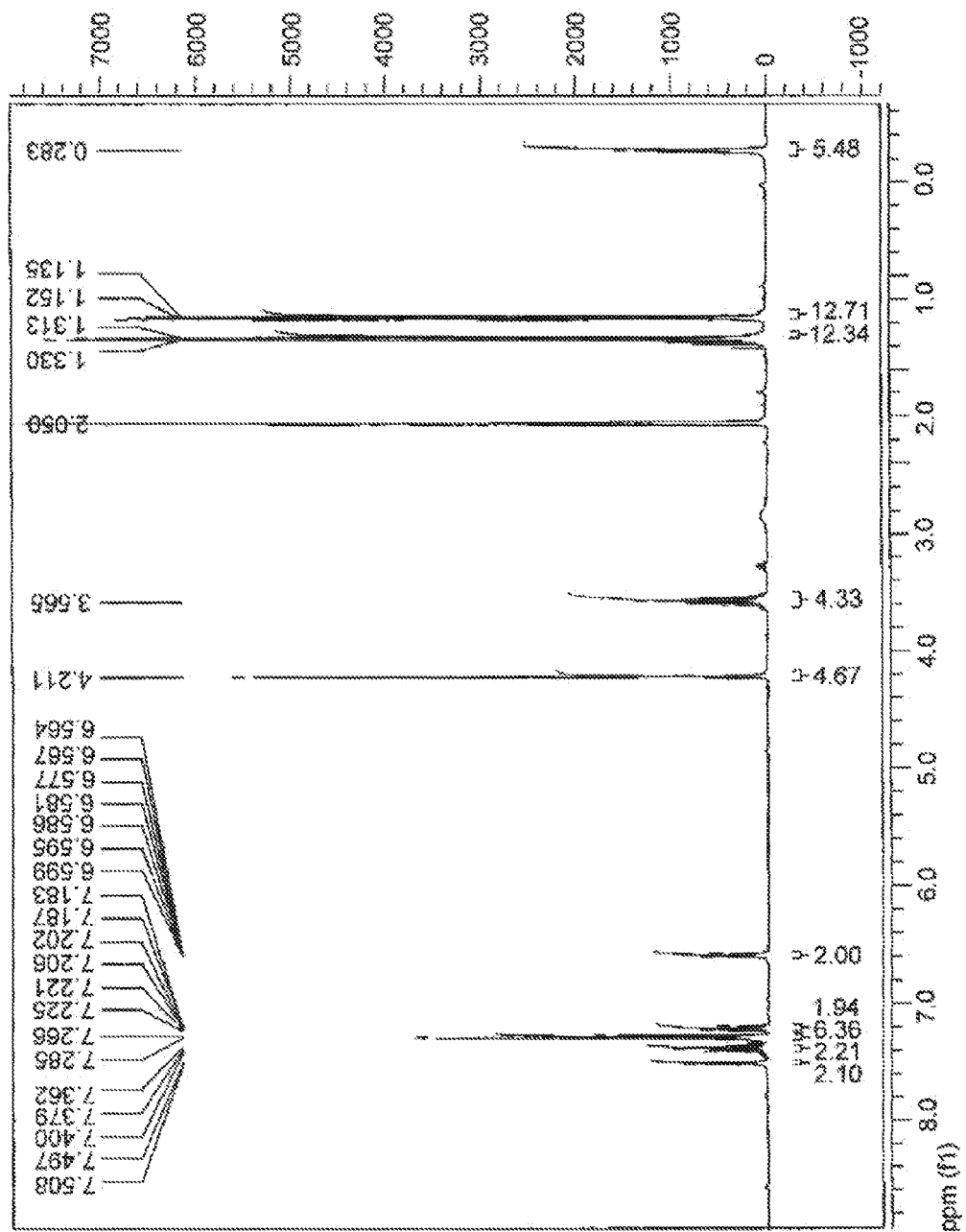
FIG. 28A shows $^1$H-NMR spectrum of Complex 7.
Figure 28B:
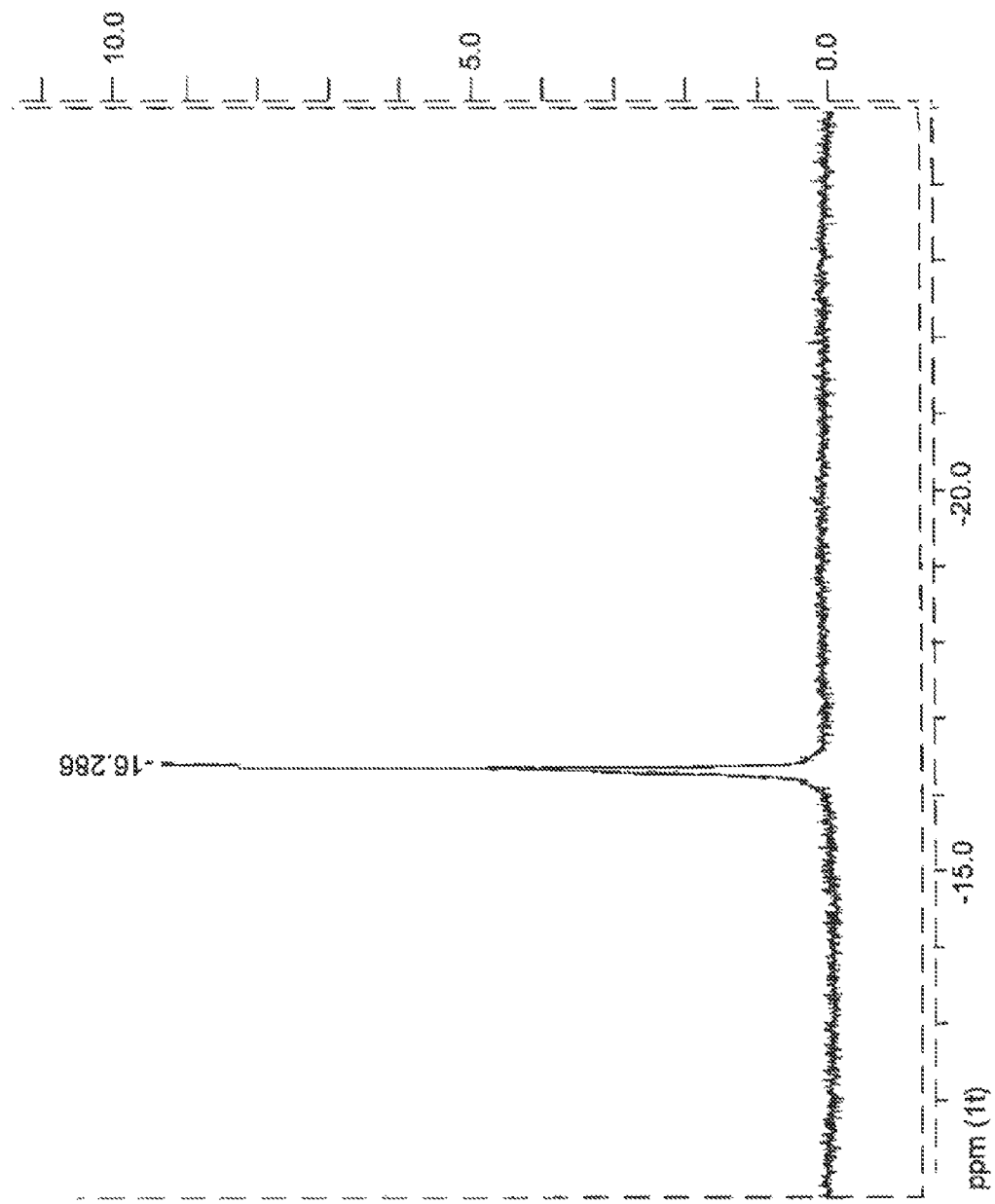
FIG. 28B shows the $^{11}$B-NMR spectrum of Complex 7.
Figure 29:
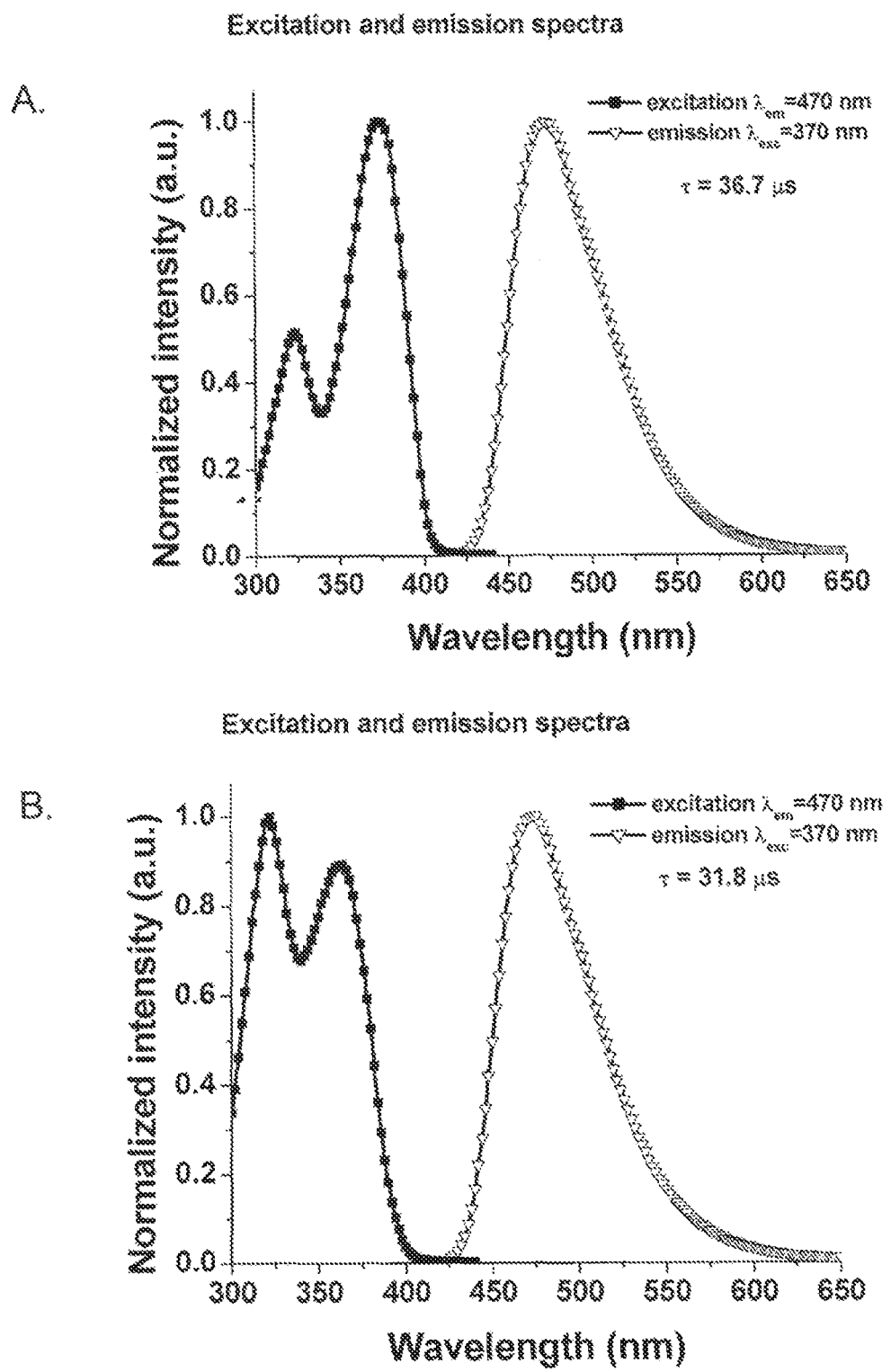
FIG. 29A shows excitation and emission spectra of Complex 7 in 2MeTHF at 77K.
FIG. 29B shows excitation and emission spectra of Complex 8 in 2MeTHF at 77K.
Figure 30:
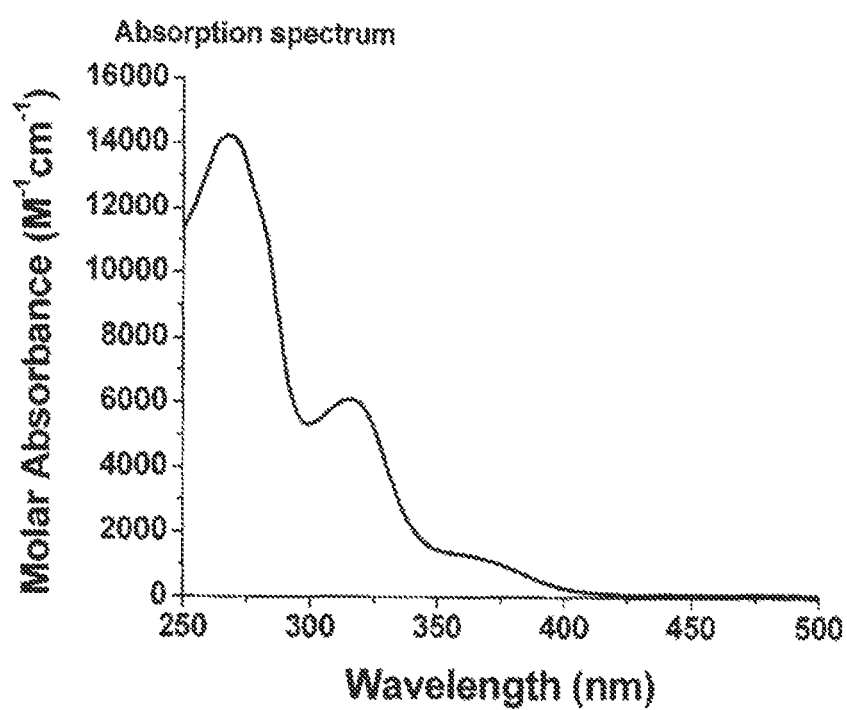
FIG. 30A shows absorption spectrum of Complex 7.
FIG. 30B shows the X-ray structure of Complex 7.
Figure 30:
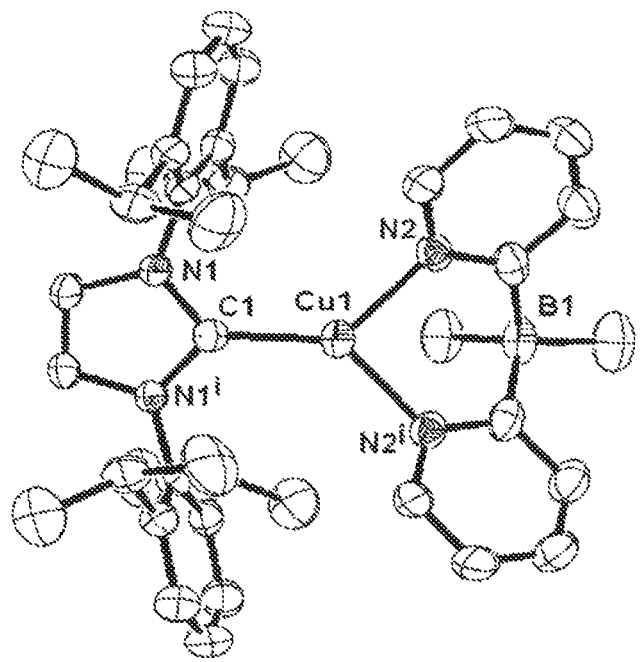

Novel trigonal planar copper complexes with a carbene ligand are provided (illustrated in FIG. 3). In particular, the complexes include a monodentate or a bidentate carbene ligand coordinated to a three coordinate copper atom. The complex can be either charged or neutral. These complexes may be advantageously used in organic light emitting devices.

Phosphorescent copper complexes and their incorporation into organic light emitting diodes (OLEDs) is known. See, e.g., Armaroli, N.; Accorsi, G.; Holler, M.; Moudam, O.;

Nierengarten, J. F.; Zhou, Z.; Wegh, R. T.; Welter, R., Highly luminescent Cu—I complexes for light-emitting electrochemical cells. *Advanced Materials* 2006, 18, (10), 1313-1316; Zhang, Q. S.; Zhou, Q. G.; Cheng, Y. X.; Wang, L. X.; Ma, O. G.; Jing, X. B.; Wang, F. S., Highly efficient green phosphorescent organic light-emitting diodes based on Cu—I complexes. *Advanced Materials* 2004, 16, (5), 432436; Yersin, H.; Monkowius, D.; Czerwieniec, R.; Yu, 1., Copper(I) N-heterocyclic chelate phosphine complexes as blue-emitting materials for organic electroluminescence devices. PCT Int. Appl. (2010), WO 2010031485 A1 20100325; and Ikeda, S.; Nagashima, H.; Ogiwara, T., Copper complexes and their use for luminescent materials, organic electroluminescence elements, and devices containing the elements. Jpn. Kokai Tokkyo Koho (2008), JP 2008303152 A 20081218. However, the reported complexes have limitations. A new class of highly phosphorescent copper complexes, with both carbene and chelating anionic ligands, are provided. It is believed that the carbene ligand will give the complex stability and enhance phosphorescence. The chelating anionic ligand is a high triplet energy ligand, capable of supporting metal-to-ligand charge transfer interactions. The complexes in this class may provide high energy phosphorescence, which can be useful in the fabrication of doped OLEDs, in which the copper complex is an emissive dopant. These materials may also be used as host materials to support an emissive dopant in an OLED structure. For example, a dipyridyl borate complex in this class of compounds has an emission maximum of 475 nm and a photoluminescence efficiency of 0.95 in the solid state. Suitable substitution of the pyridyl groups can red or blue shift this emission substantially. The ability to tune emission energies may make these copper complexes excellent emitters and host materials for OLEDs. It is thought that the emission energy may be shifted high enough to make these compounds suitable host materials for deep blue to violet emissive dopants.

Phosphorescent OLEDs have relied largely on heavy metal complexes as emitters. In particular, devices often utilize emitters containing Ir or Pt to induce spin orbit coupling. Tetrahedral copper complexes have been reported, and are known to phosphoresce at room temperature. However, tetrahedral copper complexes may have certain limitations. In particular, flattening distortions may increase the non-radiative rate, which leads to a decrease in luminescence efficiency. Trigonal planar copper carbene complexes have now been found to give efficient phosphorescence at room temperature. We believe that this is the first observation of phosphorescence from trigonal planar copper complexes.

Trigonal planar copper complexes may also have several advantages for use in OLEDs. In particular, the trigonal planar copper complexes have comparatively short lifetimes, in the tens of microsecond range (see Table 1). Table 1 shows the lifetimes of several different trigonal planar copper carbene complexes. Generally, the lifetime of the trigonal copper complex is longer than an Ir complex (i.e., 1-10 µs) but shorter than that of a platinum porphyrin complex.

TABLE 1

| | Solid state QY | Lifetime 77K 2MeTHF | λmax 77K 2MeTHF |
|---|---|---|---|
| Complex 1 | 31.8% | $\tau_1$ = 1143 µs (30.1%) $\tau_2$ = 458.5 µs (69.6%) | 440 nm |

TABLE 1-continued

| | Solid state QY | Lifetime 77K 2MeTHF | λmax 77K 2MeTHF |
|---|---|---|---|
| Complex 2 | 2.6% | τ = 10.6 µs | 605 nm |
| Complex 3 | 0.5% | τ = 0.7 µs | 615 nm |
| Complex 4 | 43.3% 33% (PMMA film) | τ = 55.9 µs | 545 nm |

In particular, several of the copper complexes provide efficient phosphorescence at room temperature and have comparatively short lifetimes, i.e., in the 10's of microsecond range. Table 2 shows the lifetimes of several different trigonal planar copper carbene complexes.

TABLE 2

| | Solid state QY | Lifetime 77K 2MeTHF | λmax 77K 2MeTHF |
|---|---|---|---|
| Complex 1 | 31.8% | τ = 656 µs | 443 nm |
| Complex 2 | 2.6% | $\tau_1$ = 1.8 µs (24%) $\tau_2$ = 4.6 µs (76%) | 630 nm |
| Complex 3 | 0.5% | τ = 0.7 µs | 645 nm |
| Complex 4 | 58% 35% (PMMA film) | τ = 55.9 µs | 555 nm |
| Complex 5 | 13.5% | τ = 2312 µs | 562; 574; 610; 660 nm |
| Complex 6 | 21% | τ = 55 µs | 560 nm |

Trigonal planar copper complexes may also be particularly useful in OLEDs used for certain applications. In particular, copper complexes provide a broader line spectrum which is especially useful for lighting applications. Further, a device comprising a trigonal planar copper complex in combination with only one other complex may cover red, green, and blue colors. For example, a device comprising a trigonal planar copper complex and a blue emitter may cover all colors required for lighting.

Novel phosphorescent complexes are provided, the complexes comprising a carbene ligand coordinated to a three coordinate copper atom.

In one aspect, the carbene ligand has the formula:

Formula I

*C is a divalent carbon atom coordinated to a monovalent copper atom Cu. $X_1$ and $X_2$ are substituents independently selected from alkyl, amine, phosphine, heteroalkyl, aryl and heteroaryl. $X_1$ and $X_2$ may be further substituted, and $X_1$ and $X_2$ are optionally linked to form a cycle. In one aspect, the carbene ligand is monodentate. Preferably, each of $X_1$ and $X_2$ independently forms a bond with *C. A first bond is formed between *C and an atom $X'_1$ in substituent $X_1$, and a second bond is formed between *C and an atom $X'_2$ in substituent $X_2$. $X'_1$ and $X'_2$ are independently selected from the group consisting of C, N, O, S and P.

In another aspect, the carbene ligand is monodentate.

In one aspect, $X_1$ and $X_2$ are not joined to form a cycle.

In another aspect, $X_1$ and $X_2$ are joined to form a cycle.

In one aspect, the copper complex is neutral. Neutral complexes may be particularly beneficial for use in OLEDs.

For example, a neutral complex can be deposited via vapor deposition. In another aspect, the copper complex is charged.

In one aspect, the complex has the formula:

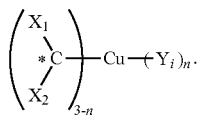

Formula II

Yi is independently selected from the group consisting of alkyl, alkoxy, amino, alkenyl, alkynyl, arylalkyl, heteroalkyl, aryl and heteroaryl. Yi is a monodentate ligand or a bidentate ligand. n is 1 or 2. Preferably, n is 2.

In another aspect, the complex has the formula:

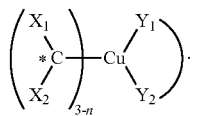

Formula III $Y_1$ and $Y_2$ are substituents that are independently selected from the group consisting of alkyl, heteroalkyl, aryl and heteroaryl. $Y_1$ and $Y_2$ may be further substituted. $Y_1$ and $Y_2$ are joined. Each of $Y_1$ and $Y_2$ form a bond with Cu. A first bond is formed between Cu and an atom $Y'_1$ in substituent $Y_1$ and a second bond is formed between Cu and an atom $Y'_2$ in substituent $Y_2$. $Y'_1$ is selected from the group consisting of N, P, *C, O, and S. $Y'_2$ is selected from the group consisting of N, P, *C, tetravalent carbon, O, and S. Preferably, $Y'_1$ is N.

The Cu atom, the $Y'_1$ atom and the $Y'_2$ atom in the complex are included in a ring that can be, for example, a 4-membered, 5-membered, 6-membered, 7-membered, or 8-membered ring. Preferably, the ring comprising Cu, $Y'_1$ and $Y'_2$ is a 5-membered or 6-membered ring.

In one aspect, $Y_1$ is selected from the group consisting of pyridyl, pyrazole, alkyl amine, imidazole, benzimidazole, triazole, tetrazole, pyridazine, pyrimidine, pyrazine, triazine, tetrazine, oxazole, thiazole, benzoxazole and benzothiazole.

In another aspect, $Y_1$-$Y_2$ is selected from the group consisting of:

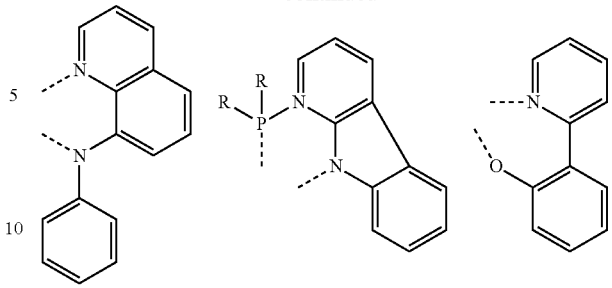

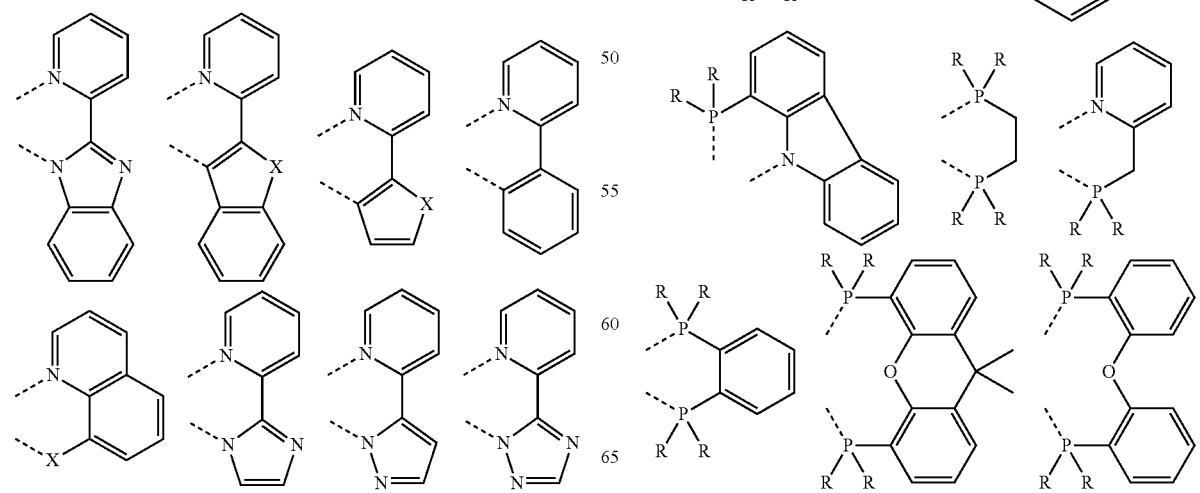

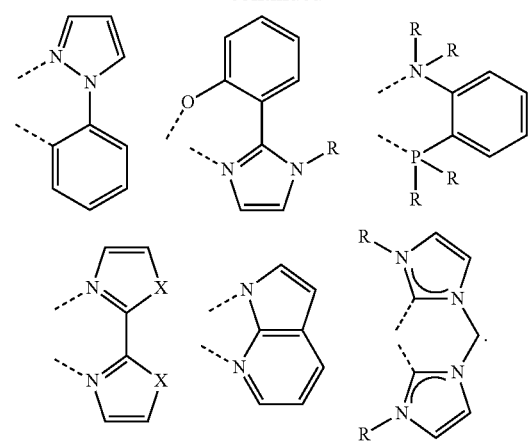

X is selected from the group consisting of NR, O, S, Se, CR$_2$, and CO. Each R is independently selected from the group consisting of hydrogen, alkyl, alkoxy, amino, alkenyl, alkynyl, arylalkyl, heteroalkyl, aryl and heteroaryl. Each ring is further substituted by a substituent selected from the group consisting of hydrogen, alkyl, alkoxy, amino, alkenyl, alkynyl, arylalkyl, heteroalkyl, aryl and heteroaryl.

In one aspect, each R includes a substituent independently selected from the group consisting of carbazole, dibenzofuran, dibenzothiophene, azacarbazole, azadibenzofuran, and azadibenzothiophene.

In yet another aspect, Y$_1$-Y$_2$ is selected from the group consisting of:

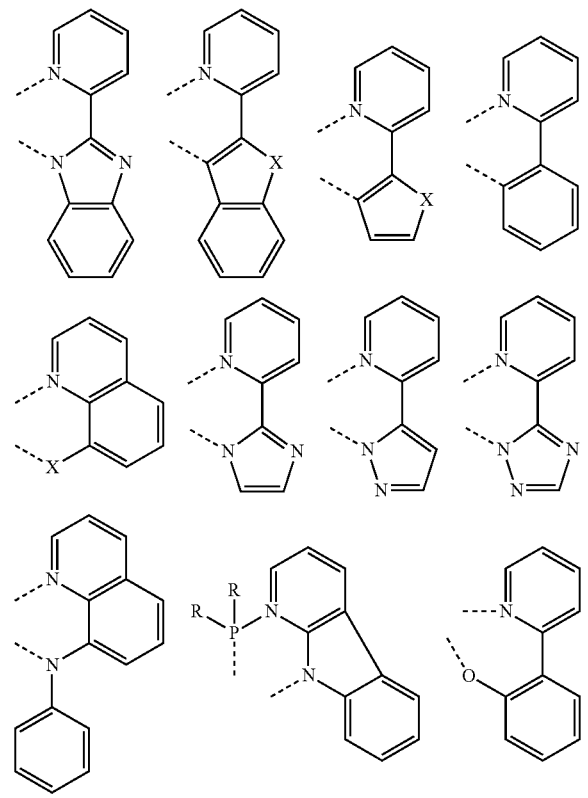

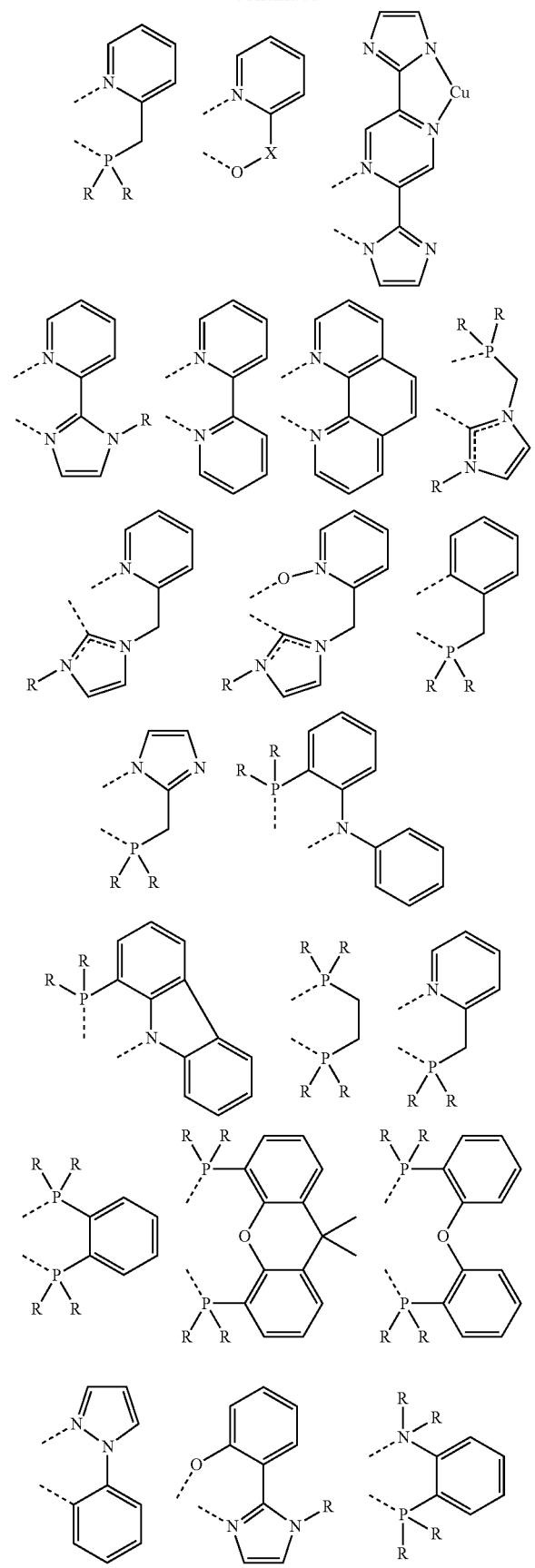

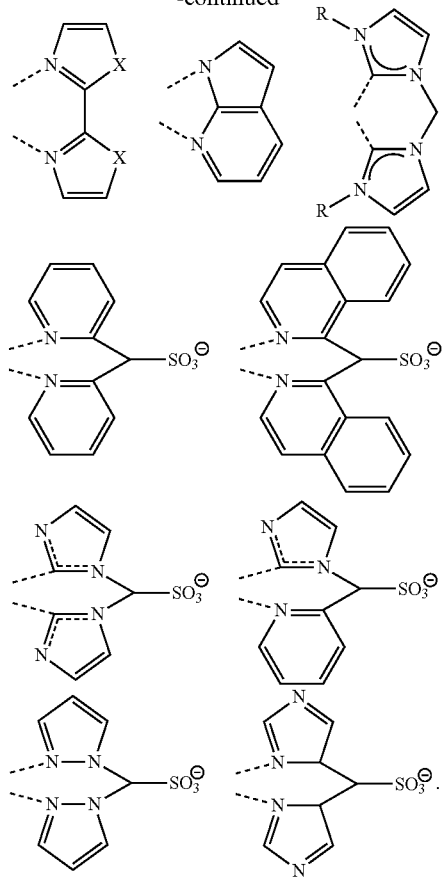

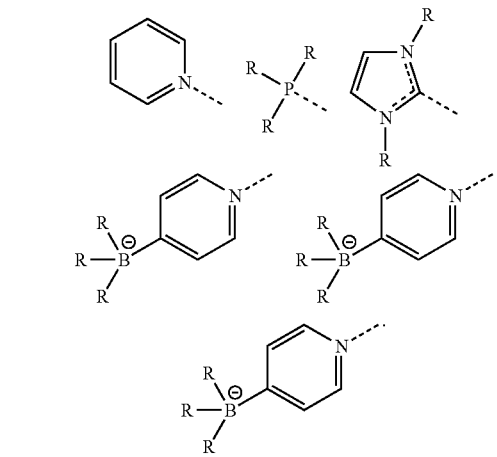

$Y_1$ and $Y_2$ are independently selected from the group consisting of pyridyl, pyrimidyl, pyrazinyl, pyridazinyl, triazinyl, tetrazinyl, triazolyl, tetrazolyl, pyrazolyl, imidazolyl, benzimidazolyl, oxazolyl, thiszolyl, benzoxazolyl, benzothiazolyl and phosphine. $Y_1$ and $Y_2$ may be extended by fusion, e.g., benzanulation. Additionally, $Y_1$ and $Y_2$ may be further substituted with alkyl, aryl, donor or acceptor groups. $Y_3$ and $Y_4$ are independently selected from the group consisting of hydrogen, alkyl, aryl, alkoxy, amino, alkenyl, alkynyl, arylalkyl, heteralkyl and heteroaryl. In one aspect, $Y_3$ and $Y_4$ are joined to form a cycle, may be extended by fusion, e.g., benzanulation.

In another aspect, $Y_i$ is a bidentate ligand having the formula $BY_4^-$. Preferably, the ligand $Y_i$ is selected from the group consisting of:

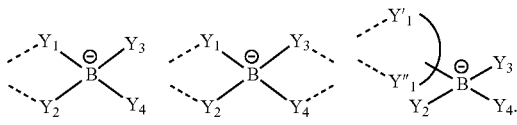

In this aspect, $Y_1$ is a bidentate chelating ligand having the formula:

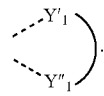

$Y'_1$-$Y'''_1$ represents a neutral, i.e., uncharged, chelating ligand. $Y'_1$-$Y'''_1$ are capable of coordinating to a metal center.

Specific examples of the $Y'_1$-$Y'''_1$ ligand include, but are not limited to, ligands having the structure:

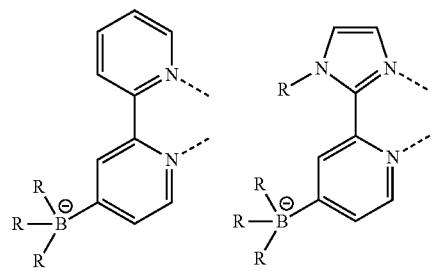

X is selected from the group consisting of NR, O, S, Se, $CR_2$, and CO. Each R is independently selected from the group consisting of hydrogen, alkyl, alkoxy, amino, alkenyl, alkynyl, arylalkyl, heteroalkyl, aryl and heteroaryl. Each ring is further substituted by a substituent selected from the group consisting of hydrogen, alkyl, alkoxy, amino, alkenyl, alkynyl, arylalkyl, heteroalkyl, aryl and heteroaryl.

In one aspect, each R includes a substituent independently selected from the group consisting of carbazole, dibenzofuran, dibenzothiophene, azacarbazole, azadibenzofuran, and azadibenzothiophene.

In another aspect, $Y_i$ is an unconjugated, monoanionic ligand containing $BY_4^-$, $SO_3Y^-$, $CY_4^-$, $SiO_4^-$, $OY_2^-$, or $SY_2^-$. Each Y is independently selected from the group consisting of hydrogen, alkyl, aryl, alkoxy, amino, alkenyl, alkynyl, arylalkyl, heteralkyl and heteroaryl.

In one aspect, $Y_i$ is $BY_4^-$. In another aspect, the ligand Yi comprises two monodentate ligands, at least one of which is $BY_4^-$. Preferably, the ligand $Y_i$ has the formula:

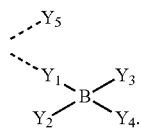

More preferably, the ligand $Y_i$ that comprises two monodentate ligands, at least one of which is $BY_4^-$, is selected from the group consisting of:

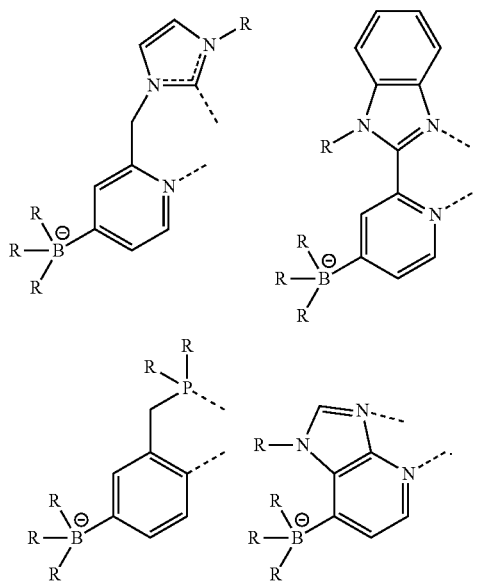

Each R is independently selected from the group consisting of hydrogen, alkyl, alkoxy, amino, alkenyl, alkynyl, arylalkyl, heteroalkyl, aryl and heteroaryl.

$Y_1$ and $Y_2$ are independently selected from the group consisting of pyridyl, pyrimidyl, pyrazinyl, pyridazinyl, triazinyl, tetrazinyl, triazolyl, tetrazolyl, pyrazolyl, imidazolyl, benzimidazolyl, oxazolyl, thiszolyl, benzoxazolyl, benzothiazolyl and phosphine. $Y_1$ and $Y_2$ may be extended by fusion, e.g., benzanulation. Additionally, $Y_1$ and $Y_2$ may be further substituted with alkyl, aryl, donor or acceptor groups.

$Y_3$ and $Y_4$ are independently selected from the group consisting of hydrogen, alkyl, aryl, alkoxy, amino, alkenyl, alkynyl, arylalkyl, heteralkyl and heteroaryl. In one aspect, $Y_3$ and $Y_4$ are joined to form a cycle, which may be extended by fusion, e.g., benzanulation.

In one aspect, $Y_1$ and $Y_2$ are the same. Specific examples of ligands where $Y_1$ and $Y_2$ are the same include, but are not limited to, ligands selected from the group consisting of:

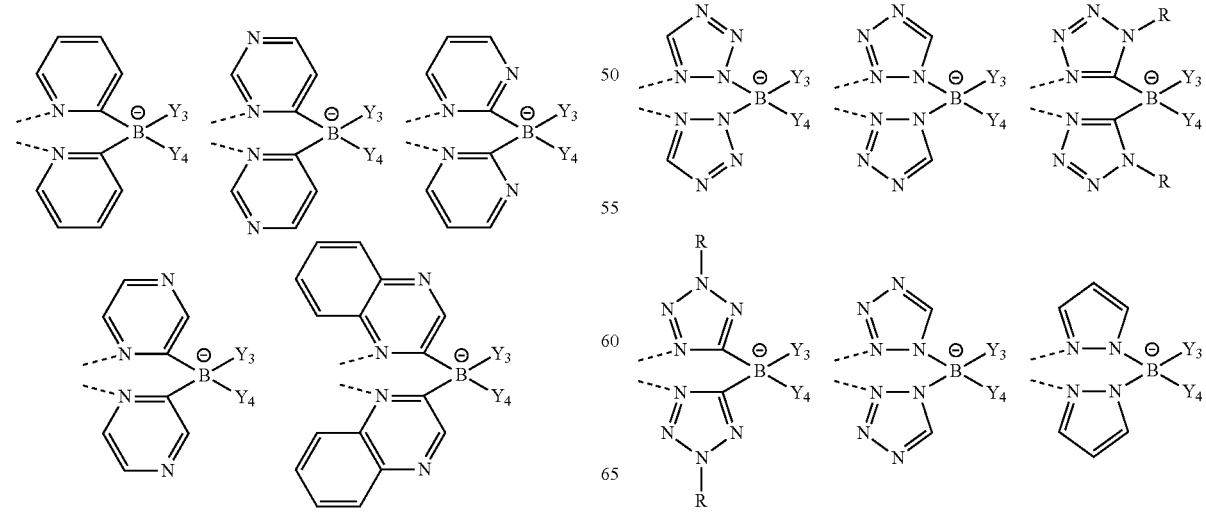

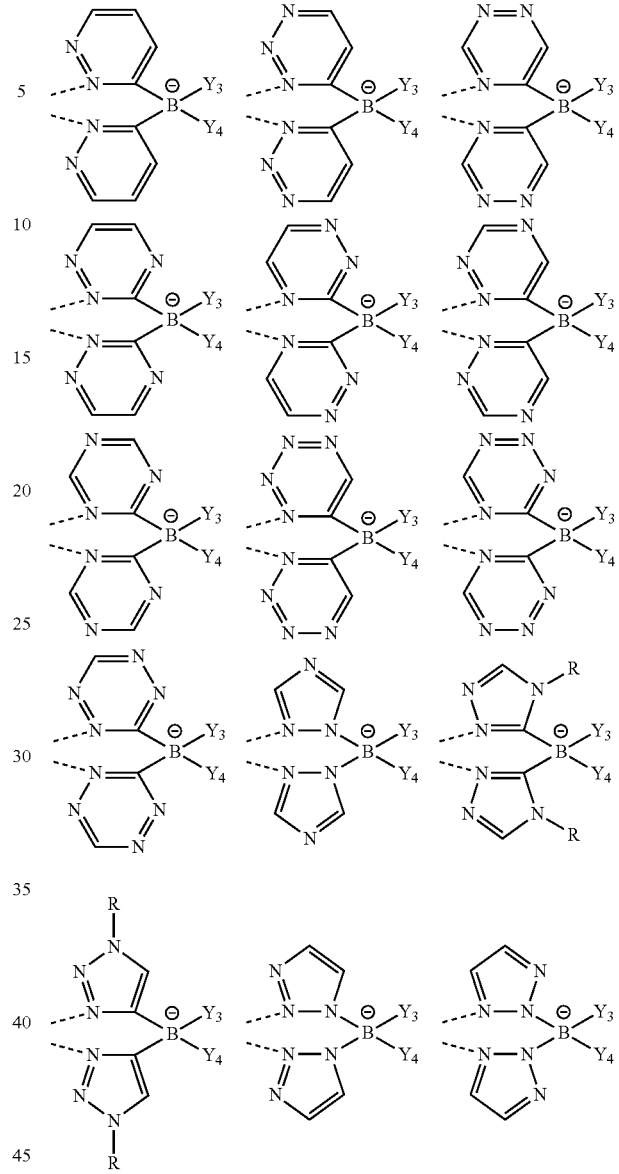

-continued

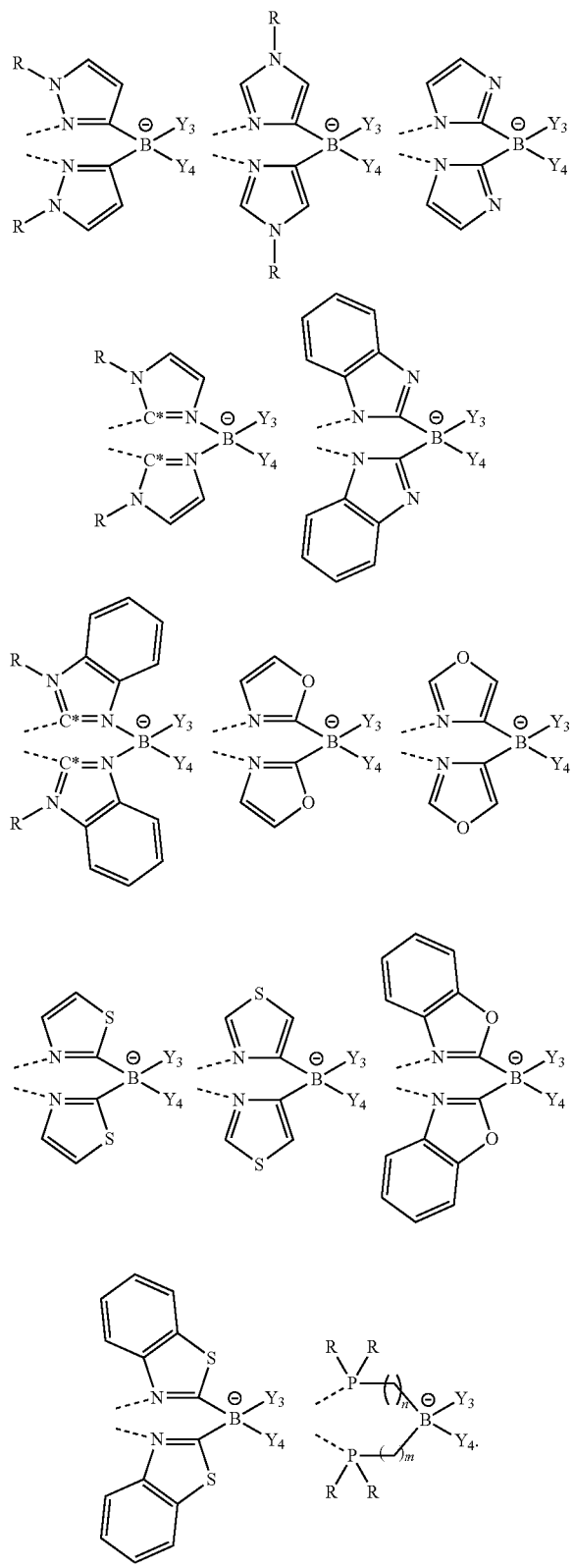

Each R is independently selected from the group consisting of hydrogen, alkyl, alkoxy, amino, alkenyl, alkynyl, arylalkyl, heteroalkyl, aryl and heteroaryl. C* is a divalent carbon atom. n is 0, 1, or 2. m is 0, 1, or 2.

In one aspect, $Y_1$ and $Y_2$ are different. Specific examples of ligands where $Y_1$ and $Y_2$ are different include, but are not limited to, ligands selected from the group consisting of:

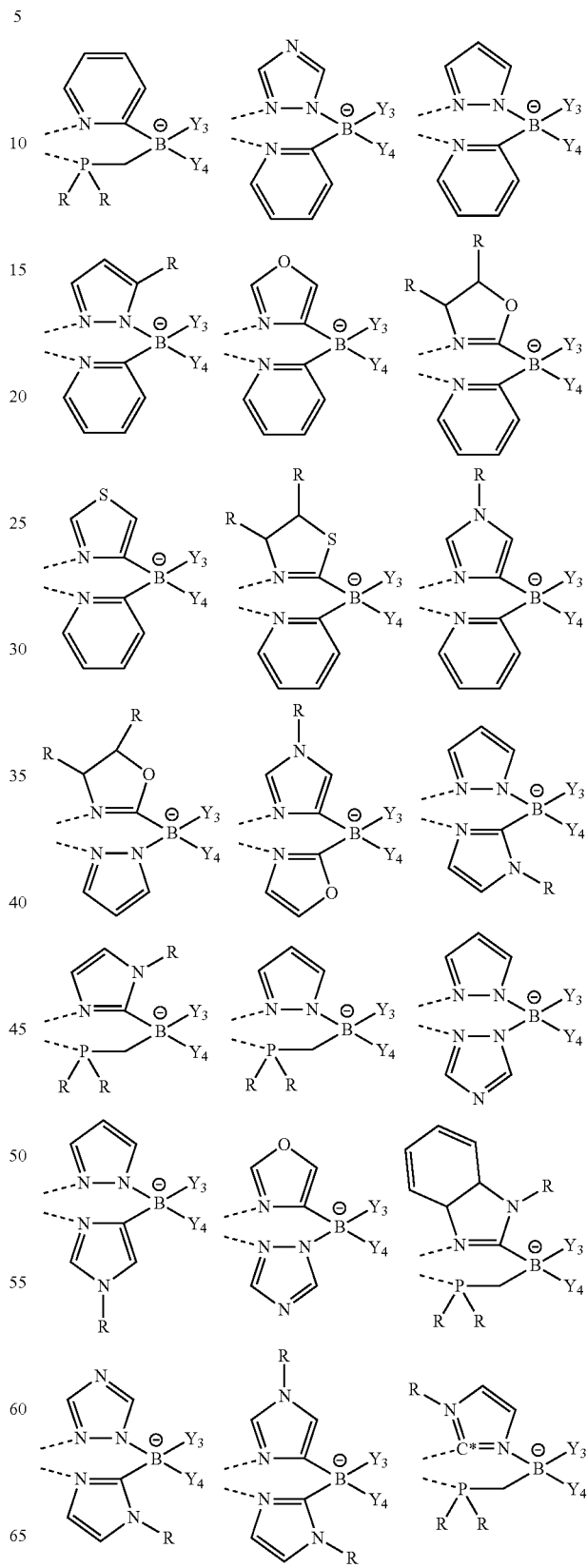

-continued

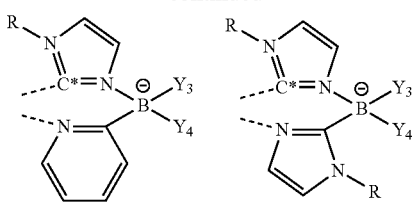

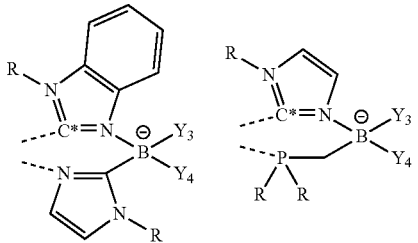

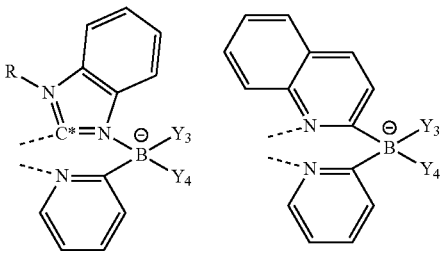

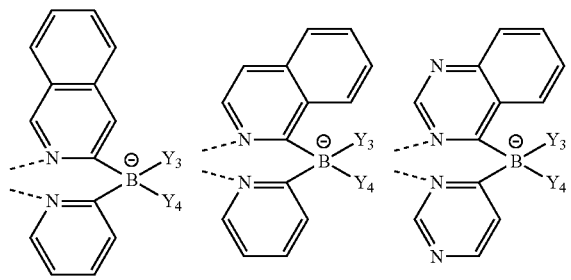

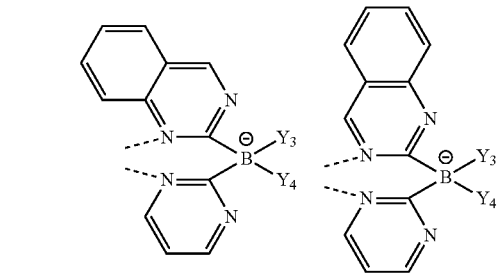

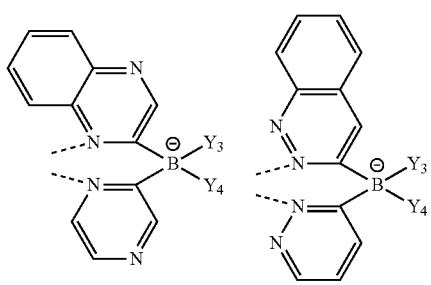

-continued

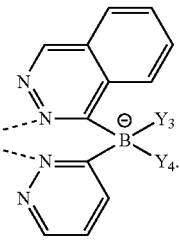

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

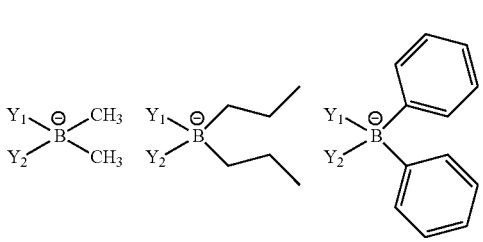

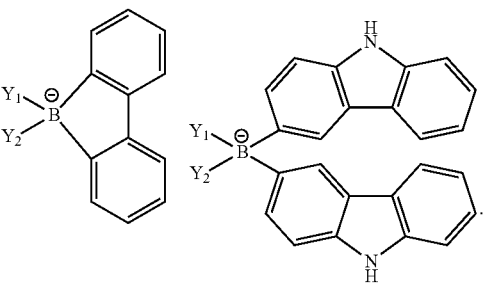

In one aspect, $Y_i$ is $SO_3Y^-$. Specific examples of ligands $Y_i$ having the formula $SO_3Y^-$ include, but are not limited to, ligands having the structure:

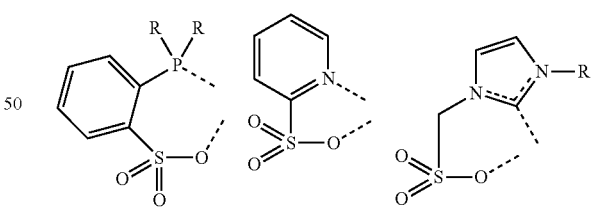

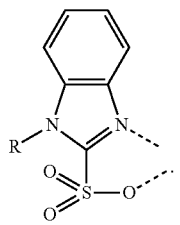

Each R is independently selected from the group consisting of hydrogen, alkyl, alkoxy, amino, alkenyl, alkynyl, arylalkyl, heteroalkyl, aryl and heteroaryl.

In one aspect, $Y_i$ is $CY_4^-$. Preferably, $CY_4^-$ has the formula:

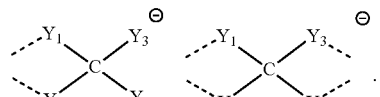

Specific examples of ligands $Y_i$ having the formula $CY_4^-$ include, but are not limited to, ligands having the structure:

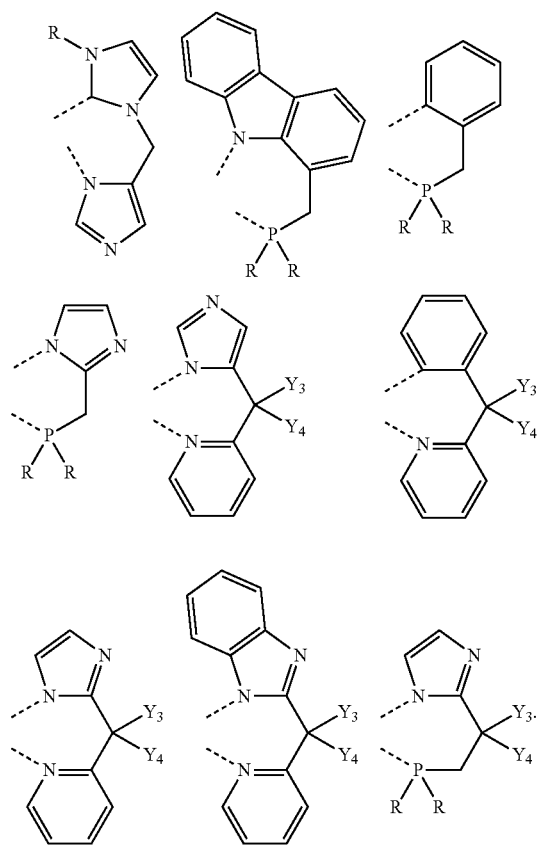

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

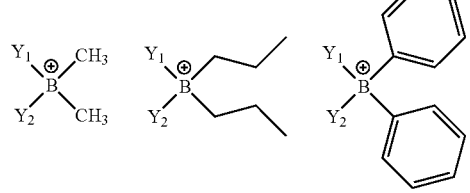

-continued

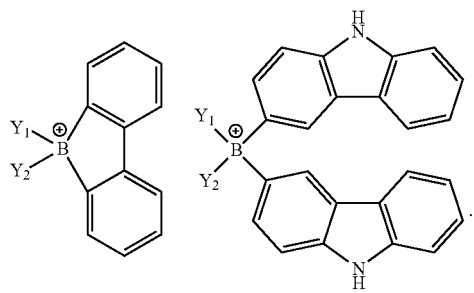

In another aspect, $Y_i$ is $SiY_4^-$. Specific examples of ligands $Y_i$ having the formula $SiY_4^-$ include, but are not limited to, ligands having the structure:

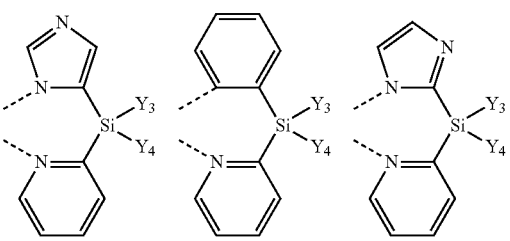

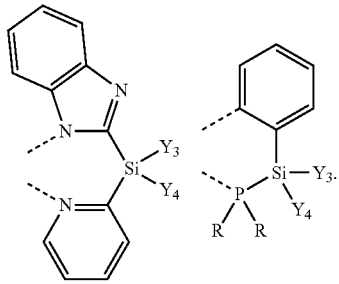

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

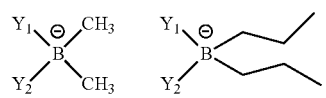

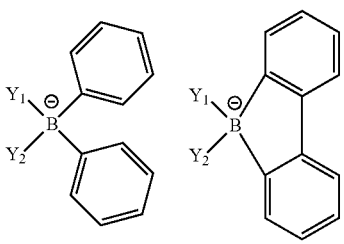

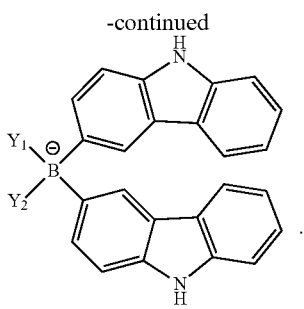

In another aspect, $Y_i$ is $OY_2^-$. Preferably, $OY_2^-$ has the formula:

Specific examples of ligands $Y_i$ having the formula $OY_2^-$ include, but are not limited to, ligands having the structure:

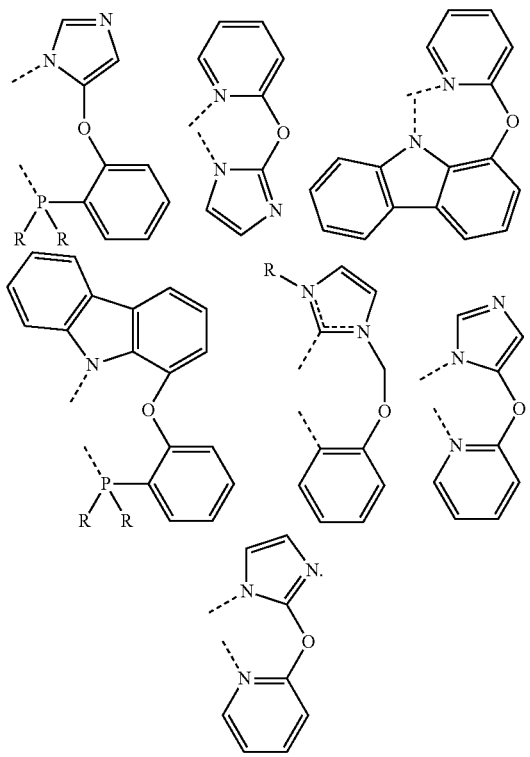

Each R is independently selected from the group consisting of hydrogen, alkyl, alkoxy, amino, alkenyl, alkynyl, arylalkyl, heteroalkyl, aryl and heteroaryl.

In one aspect, $Y_3$ and $Y_4$ are selected from the group consisting of:

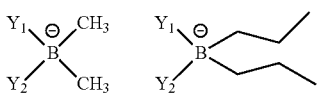

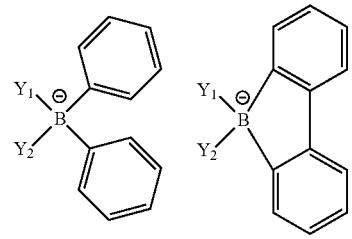

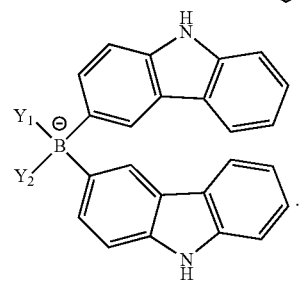

In yet another aspect, $Y_i$ is $SY_2^-$. Preferably, $SY_2^-$ has the formula:

Specific examples of ligands $Y_i$ having the formula $SY_2^-$ include, but are not limited to, ligands having the structure:

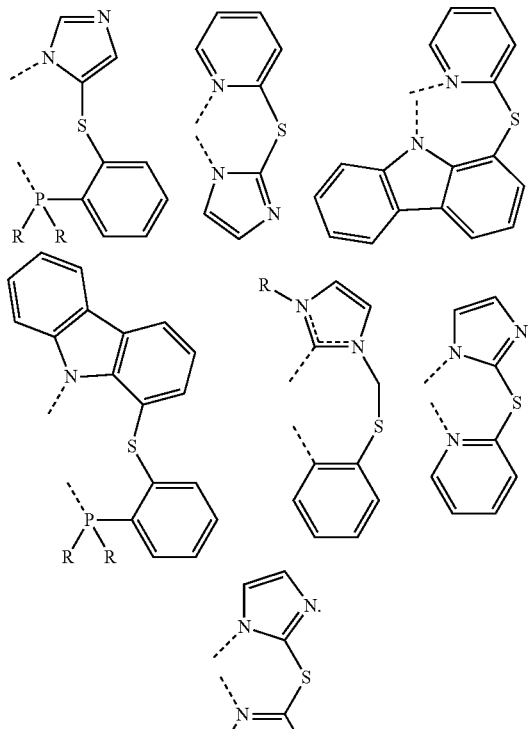

Each R is independently selected from the group consisting of hydrogen, alkyl, alkoxy, amino, alkenyl, alkynyl, arylalkyl, heteroalkyl, aryl and heteroaryl.

In one aspect, the complex comprises two copper (I) centers. Non-limiting examples of complexes comprising two copper (I) centers include complexes selected from the group consisting of:

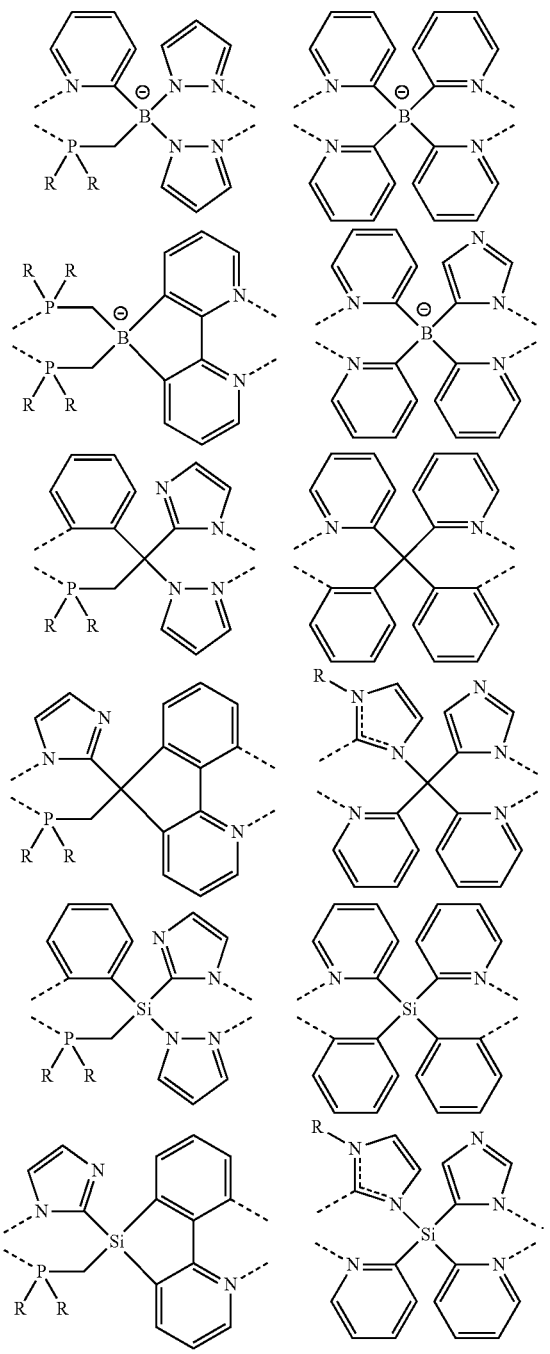

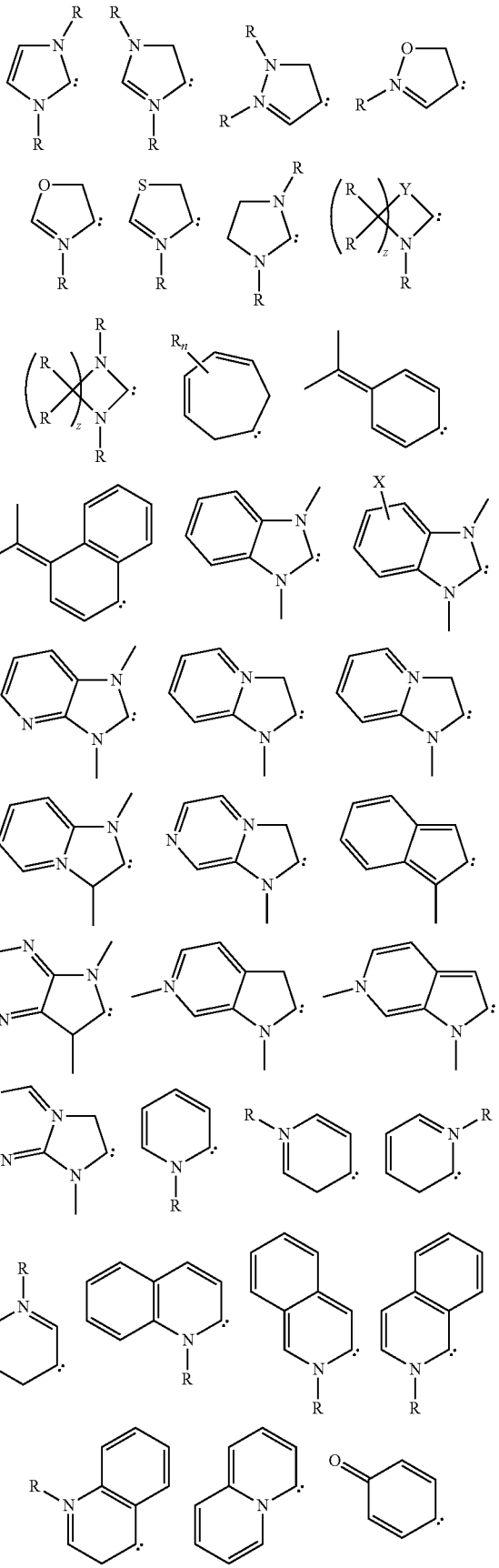

Each R is independently selected from the group consisting of hydrogen, alkyl, alkoxy, amino, alkenyl, alkynyl, arylalkyl, heteroalkyl, aryl and heteroaryl.

In a further aspect, the carbene ligand is selected from the group consisting of:

-continued

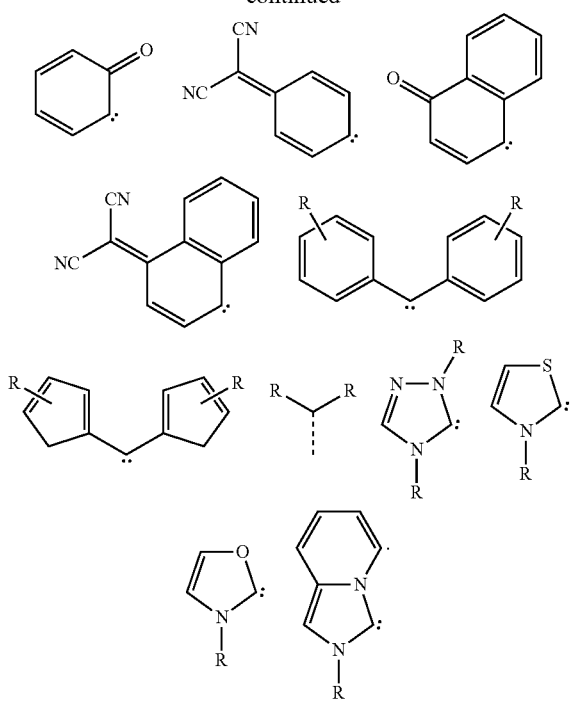

Each R is independently selected from the group consisting of hydrogen, alkyl, alkoxy, amino, alkenyl, alkynyl, arylalkyl, heteroalkyl, aryl and heteroaryl. z is 1, 2, 3, or 4.

Preferably, the carbene is

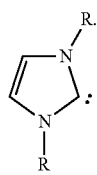

More preferably, the carbene is

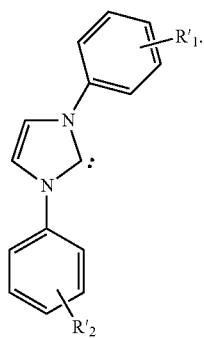

$R'_1$ and $R'_2$ may represent mono, di, tri, or tetra substitutions. $R'_1$ and $R'_2$ are independently selected from the group consisting of hydrogen, alkyl, alkoxy, amino, alkenyl, alkynyl, arylalkyl, heteroalkyl, aryl and heteroaryl. In one aspect, at least one of $R'_1$ and $R'_2$ is an alkyl having three or more carbon atoms.

Preferably, the complex is selected from the group consisting of:

Complex 1

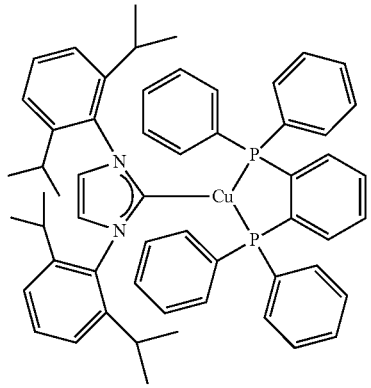

Complex 2

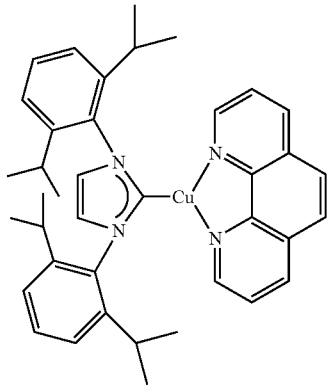

Complex 3

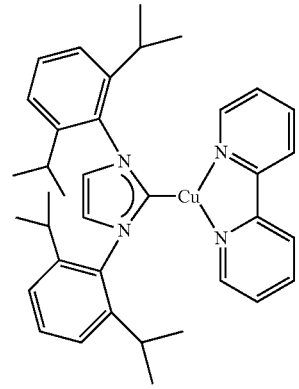

Complex 4

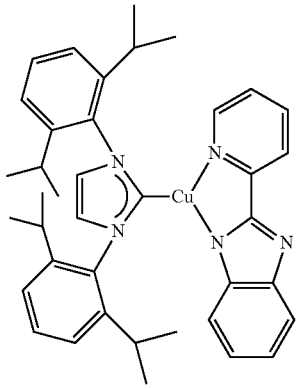

-continued
Complex 5
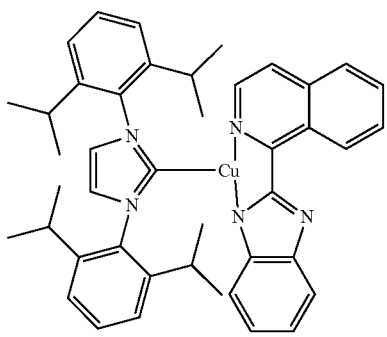
Complex 6
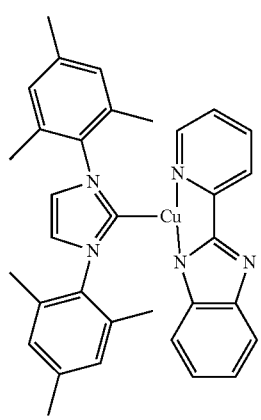
Complex 7
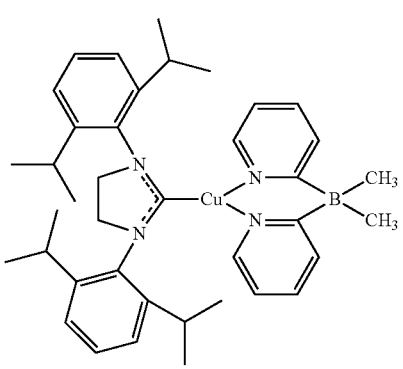
Complex 8
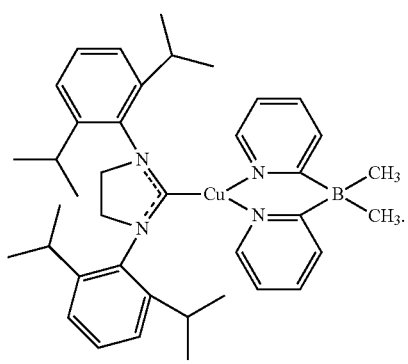
Preferably, the complex is selected from the group consisting of:
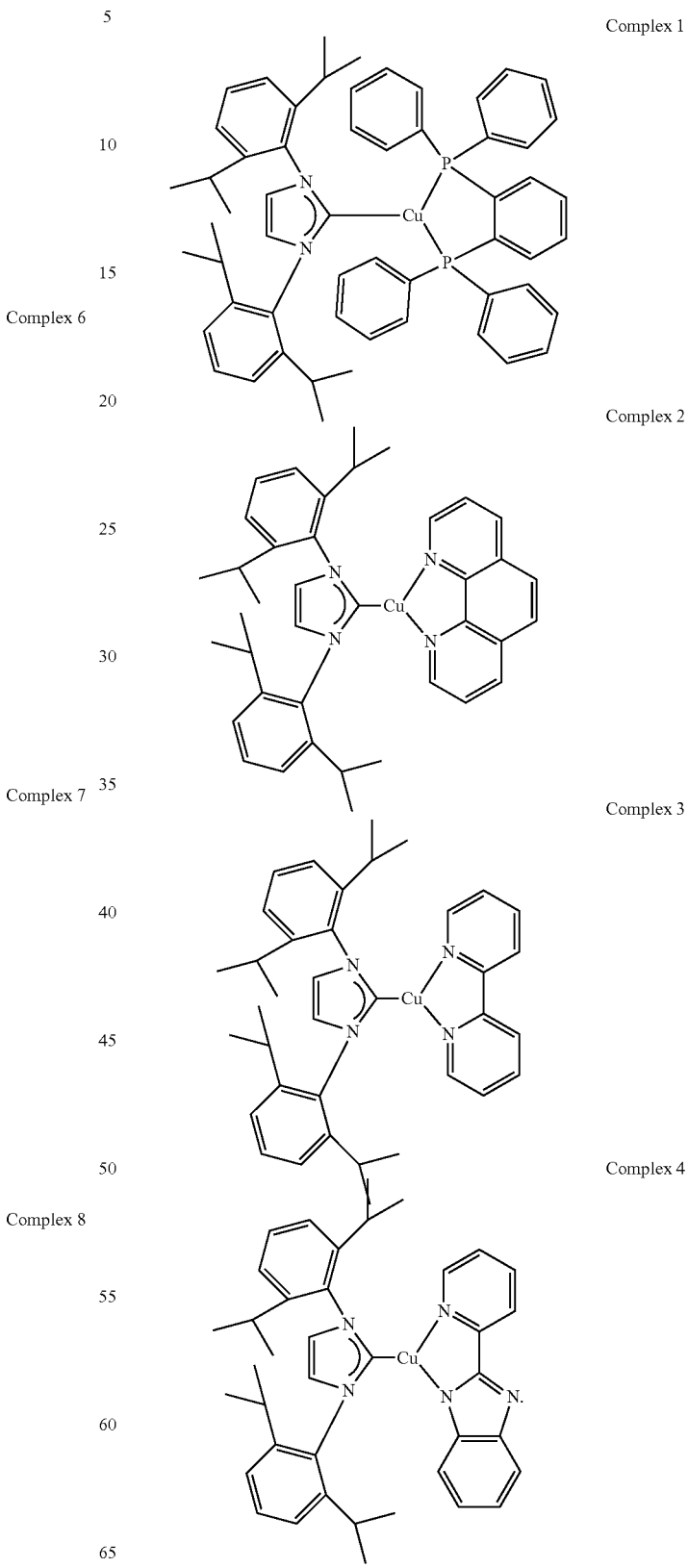

More preferably, the complex is:

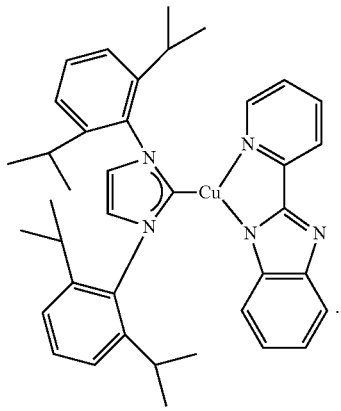

Complex 4

In another aspect, the complex has the formula:

$$\left( \begin{array}{c} X_1 \\ {}^*C \\ X_2 \end{array} \right) Cu \begin{array}{c} Y_1 \\ Y_2 \end{array}$$

Formula IV $Y_1$ and $Y_2$ are substituents that are independently selected from the group consisting of alkyl, heteroalkyl, aryl and heteroaryl. $Y_1$ and $Y_2$ may be further substituted. $Y_1$ and $Y_2$ are not joined. Each of $Y_1$ and $Y_2$ form a bond with Cu.

In one aspect, the complex is selected from the group consisting of:

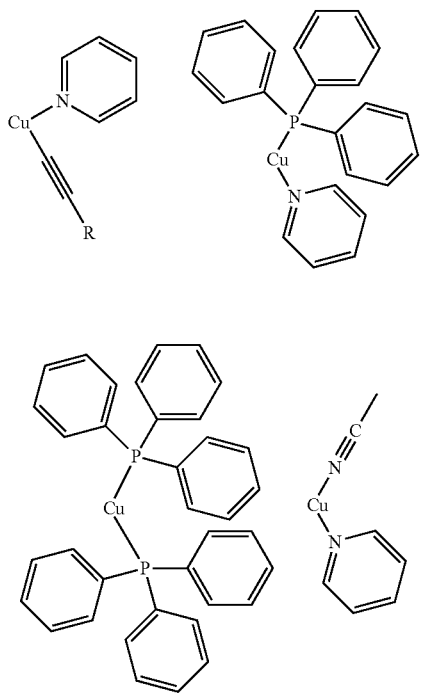

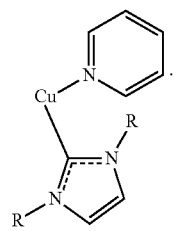

Each R is independently selected from the group consisting of hydrogen, alkyl, alkoxy, amino, alkenyl, alkynyl, arylalkyl, heteroalkyl, aryl and heteroaryl.

In another aspect, the carbene ligand is bidentate. Preferably, the complex is selected from the group consisting of:

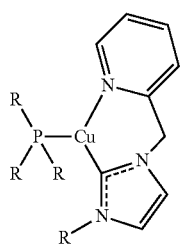 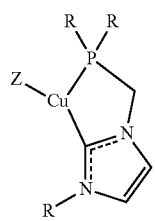

Each R is independently selected from the group consisting of hydrogen, alkyl, alkoxy, amino, alkenyl, alkynyl, arylalkyl, heteroalkyl, aryl and heteroaryl. Z is a monodentate ligand.

In one aspect, the complex is included in a polymer. In another aspect, the complex is included in the repeat unit of the polymer. In yet another aspect, the complex is pendant on the polymer. Preferably, the polymer is selected from the group consisting of:

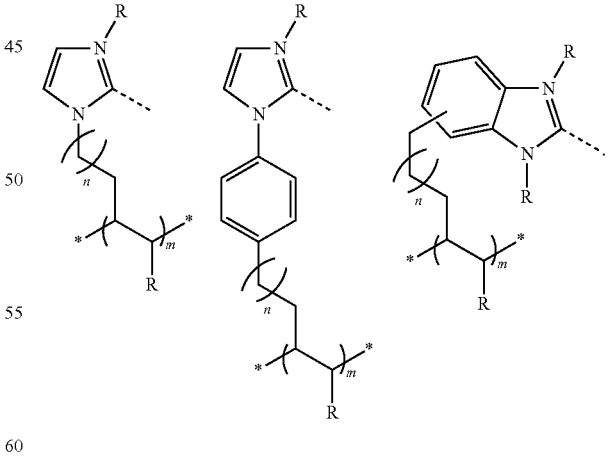

Each R is independently selected from the group consisting of hydrogen, alkyl, alkoxy, amino, alkenyl, alkynyl, arylalkyl, heteroalkyl, aryl and heteroaryl. m is greater than 2. n is 0-20.

In another aspect, the complex is included in a dendritic complex. Preferably, the dendritic complex is

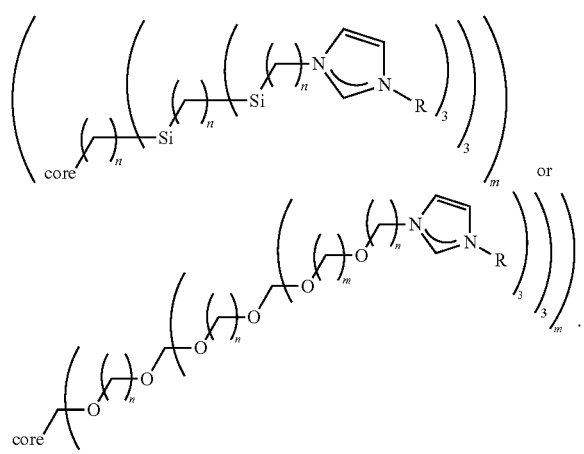

The core is a molecule or a polyvalent element selected from the group consisting of C, Si, Ge, Sn, Pb, N, P, and As. Each R is independently selected from the group consisting of hydrogen, alkyl, alkoxy, amino, alkenyl, alkynyl, arylalkyl, heteroalkyl, aryl and heteroaryl. m is greater than 1. n is 0-20.

In yet another aspect, the complex is included in a small molecule.

Devices comprising the phosphorescent complexes are also provided. A first device comprising an organic light emitting device further comprising an anode, a cathode; and an organic layer, disposed between the anode and the cathode. The organic layer further comprising a phosphorescent complex itself comprising a three coordinate copper atom and a carbene ligand. Preferably, the first device is a consumer product. The device may comprise a complex having Formula I, Formula II, Formula III, or Formula IV, as described above. Selections for the substituents, ligands, and complexes described as preferred for the complexes having Formula I, Formula II, Formula III, or Formula IV are also preferred for use in a device that comprises a complex including a complex having Formula I, Formula II, Formula III, or Formula IV. These selections include those described for $X_1$, $X_2$, $X'_1$, $X'_2$, $Y_1$, $Y_2$, $Y'_1$, $Y'_2$, Yi, R, X, and Z.

Selections for the substituents, ligands, and complexes described as preferred for the complexes having Formula I, Formula II, Formula III, or Formula IV are also preferred for use in a device that comprises a complex including a complex having Formula I, Formula II, Formula III, or Formula IV. These selections include those described for $X_1$, $X_2$, $X'_1$, $X'_2$, $Y_1$, $Y_2$, $Y_3$, $Y_4$, $Y_5$, $Y''_1$, $Y'_2$, $Y_i$, R, X, and Z.

Such devices may contain the trigonal copper complex as a neat thin film. In particular, an OLED comprising a pure film of the complex may have a higher luminescent efficiency than an OLED that comprises the complex doped with another material. Previously, it was thought that complexes cannot be used in pure films because of self-quenching. However, the trigonal copper complexes provided herein may not demonstrate the self-quenching problems seen in other complexes.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the complexes disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of complexes for each class, and references that disclose the materials.

TABLE 3

| MATERIAL | EXAMPLES OF MATERIAL | PUBLICATIONS |
| --- | --- | --- |
| Hole injection materials | | |
| Phthalocyanine and porphryin complexes | | Appl. Phys. Lett. 69, 2160 (1996) |

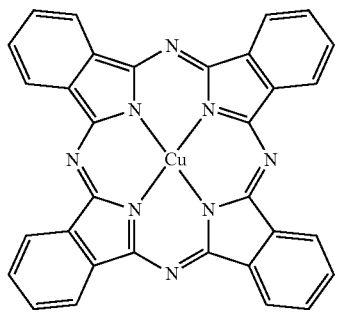

TABLE 3-continued

| MATERIAL | EXAMPLES OF MATERIAL | PUBLICATIONS |
| --- | --- | --- |
| Starburst triarylamines | | J. Lumin. 72-74, 985 (1997) |
| CF$_x$ Fluorohydrocarbon polymer | $-\!\!+\!\!CH_xF_y\!\!+\!\!_n$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |
| Triarylamine or polythiophene polymers with conductivity dopants | | EA01725079A1 | and

TABLE 3-continued

| MATERIAL | EXAMPLES OF MATERIAL | PUBLICATIONS |
| --- | --- | --- |
| Arylamines complexed with metal oxides such as molybdenum and tungsten oxides | | SID Symposium Digest, 37, 923 (2006) WO2009018009 |
| p-type semiconducting organic complexes | | US20020158242 |
| Metal organometallic complexes | | US20060240279 |

TABLE 3-continued

| MATERIAL | EXAMPLES OF MATERIAL | PUBLICATIONS |
| --- | --- | --- |
| Cross-linkable complexes | | US20080220265 |//
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |

TABLE 3-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |

TABLE 3-continued

| MATERIAL | EXAMPLES OF MATERIAL | PUBLICATIONS |
|---|---|---|
| Arylamine carbazole complexes | | Adv. Mater. 6, 677 (1994), US20080124572 |
| Triarylamine with (di)benzothiophene/ (di)benzofuran | | US20070278938, US20080106190 |
| Indolocarbazoles | | Synth. Met. 111, 421 (2000) |
| Isoindole complexes | | Chem. Mater. 15, 3148 (2003) |

TABLE 3-continued

| MATERIAL | EXAMPLES OF MATERIAL | PUBLICATIONS |
| --- | --- | --- |
| Metal carbene complexes | | US20080018221 |
| Phosphorescent OLED host materials | | |
| Red hosts | | |
| Arylcarbazoles | | Appl. Phys. Lett. 78, 1622 (2001) |
| Metal 8-hydroxy-quinolates (e.g., Alq₃, BAlq) | | Nature 395, 151 (1998) |
| | | US20060202194 |
| | | WO2005014551 |
| | | WO2006072002 |

TABLE 3-continued

| MATERIAL | EXAMPLES OF MATERIAL | PUBLICATIONS |
| --- | --- | --- |
| Metal phenoxybenzothiazole complexes | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2009062578 |

Green hosts

| | | |
| --- | --- | --- |
| Arylcarbazoles | | Appl. Phys. Lett. 78, 1622 (2001) |
| | | US20030175553 |

TABLE 3-continued

| MATERIAL | EXAMPLES OF MATERIAL | PUBLICATIONS |
|---|---|---|
| | | WO2001039234 |
| Aryltriphenylene complexes | | US20060280965 |
| | | US20060280965 |
| | | WO2009021126 |
| Donor acceptor type molecules | | WO2008056746 |

TABLE 3-continued
| MATERIAL | EXAMPLES OF MATERIAL | PUBLICATIONS |
|---|---|---|
| Aza-carbazole/DBT/DBF | 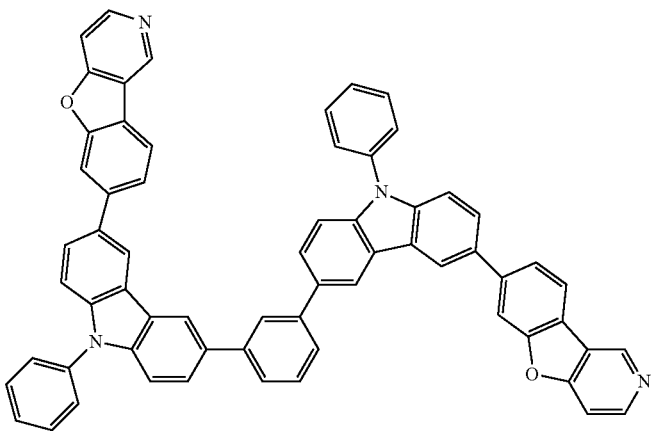 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 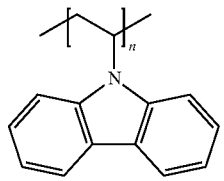 | Appl. Phys. Lett. 77, 2280 (2000) |
| Spirofluorene complexes | 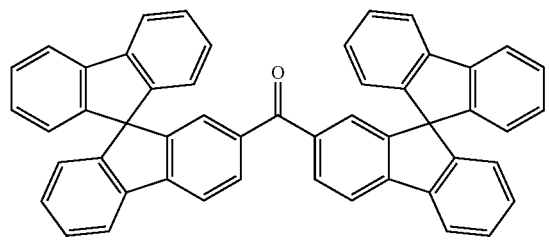 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole complexes | 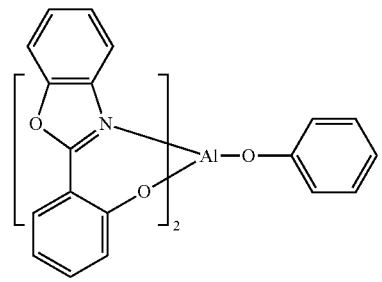 | WO2005089025 |
| | 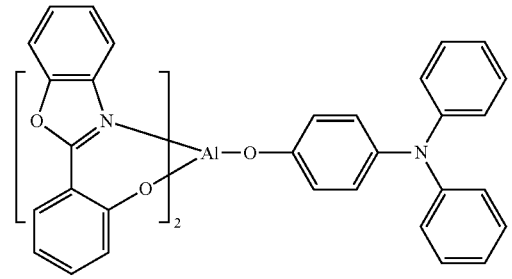 | WO2006132173 |

| MATERIAL | EXAMPLES OF MATERIAL | PUBLICATIONS |
|---|---|---|
| | | JP200511610 |
| | 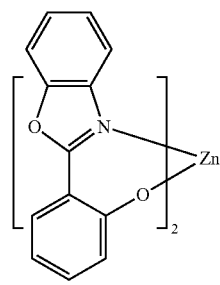 | |
| Spirofluorene-carbazole complexes | | JP2007254297 |
| | 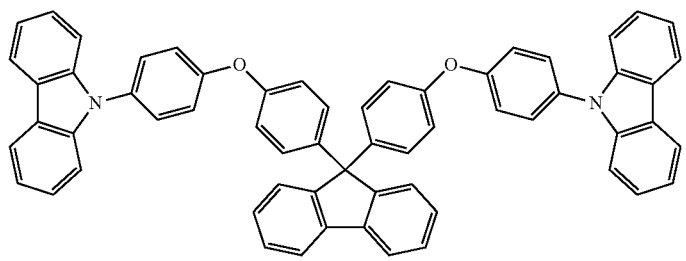 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | |
| | | JP2007254297 |
| | 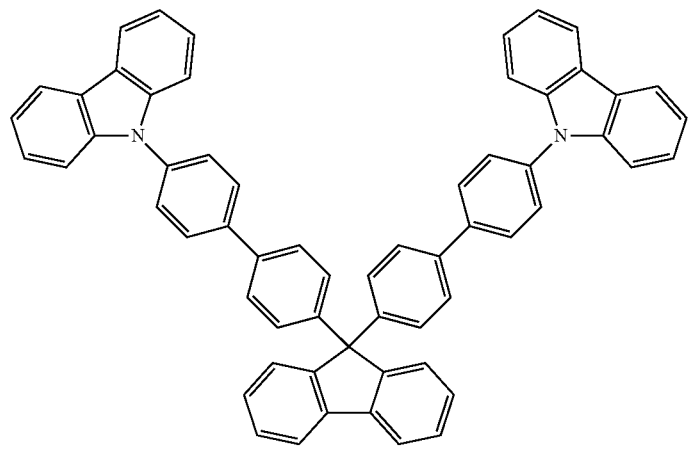 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | |
| Indolocabazoles | | WO2007063796 |
| | 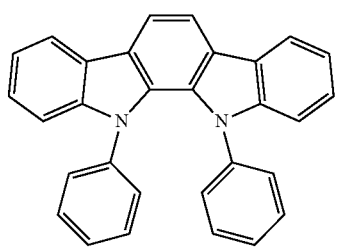 [SMILES: c1ccc(-n2c3ccccc3c3ccc4c5ccccc5n(-c5ccccc5)c4c32)cc1] | |

TABLE 3-continued

| MATERIAL | EXAMPLES OF MATERIAL | PUBLICATIONS |
|---|---|---|
|  |  | WO2007063754 |
| 5-member ring electron deficient heterocycles (e.g., triazole, oxadiazole) |  | J. Appl. Phys. 90, 5048 (2001) |
|  |  | WO2004107822 |
| Tetraphenylene complexes |  | US20050112407 |
| Metal phenoxypyridine complexes |  | WO2005030900 |

TABLE 3-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |ает
| Blue hosts | | |
| Arylcarbazoles | | Appl. Phys. Lett. 82, 2422 (2003) |
| | | US20070190359 |
| Dibenzothiophene/ Dibenzofuran-carbazole complexes | | WO2006114966, US20090167162 |
| | | US20090167162 |
| | | WO2009086028 |

| MATERIAL | EXAMPLES OF MATERIAL | PUBLICATIONS |
|---|---|---|
| | 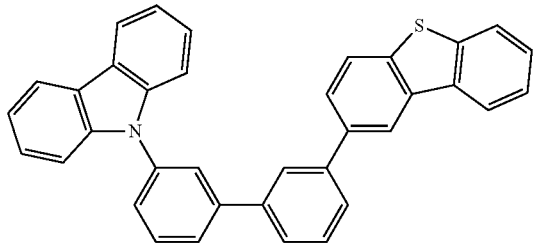 [SMILES: c1cc(-c2cccc(-n3c4ccccc4c4ccccc43)c2)cc(-c2ccc3sc4ccccc4c3c2)c1] | US20090030202, US20090017330 |
| Silicon aryl complexes | 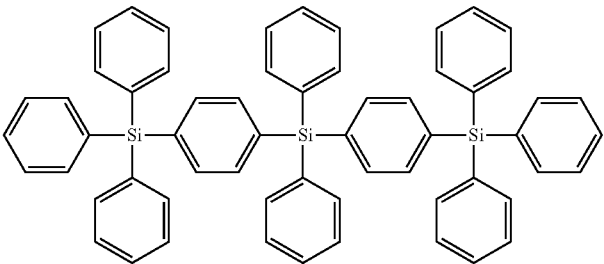 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 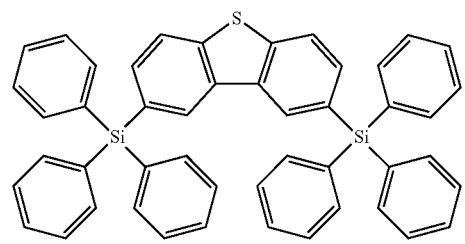 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl complexes | 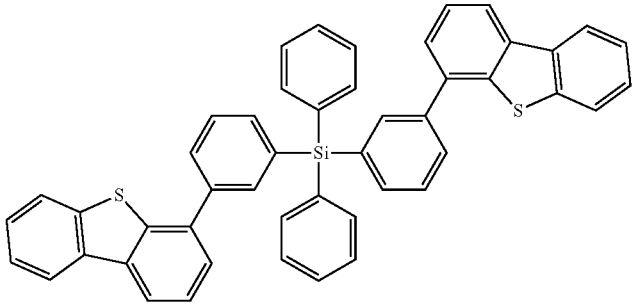 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 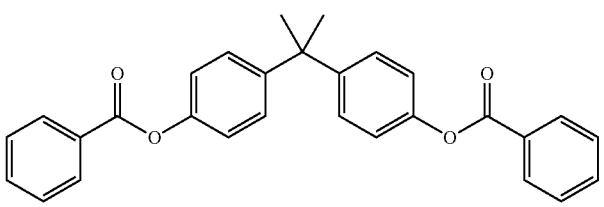 [SMILES: CC(C)(c1ccc(OC(=O)c2ccccc2)cc1)c1ccc(OC(=O)c2ccccc2)cc1] | WO2006100298 |
| High triplet metal organometallic complex | 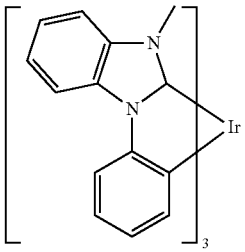 | U.S. Pat. No. 7,154,114 |

TABLE 3-continued

| MATERIAL | EXAMPLES OF MATERIAL | PUBLICATIONS |
| --- | --- | --- |
| Phosphorescent dopants Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 3-continued

| MATERIAL | EXAMPLES OF MATERIAL | PUBLICATIONS |
| --- | --- | --- |
| | | US20060202194 |
| | | US20070087321 |
| | | US20070087321 |
| | | Adv. Mater. 19, 739 (2007) |
| | | WO2009100991 |

TABLE 3-continued
| MATERIAL | EXAMPLES OF MATERIAL | PUBLICATIONS |
|---|---|---|
| | 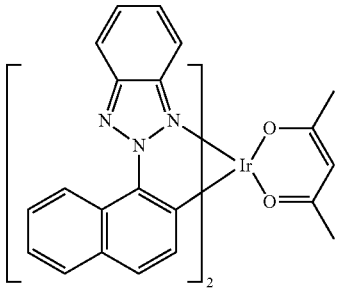 | WO2008101842 |
| Platinum(II) organometallic complexes | 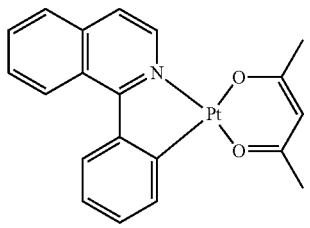 | WO2003040257 |
| Osminum(III) complexes | 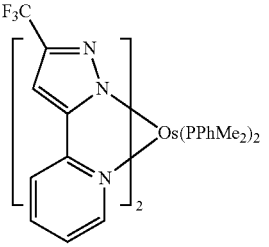 | Chem. Mater. 17, 3532 (2005) |
| Ruthenium(II) complexes | 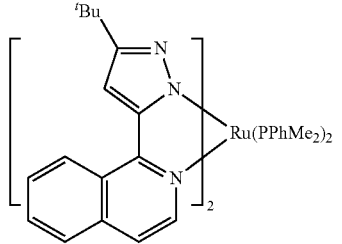 | Adv. Mater. 17, 1059 (2005) |
| Rhenium (I), (II), and (III) complexes | 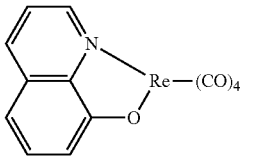 | US20050244673 |
Green dopants

TABLE 3-continued
| MATERIAL | EXAMPLES OF MATERIAL | PUBLICATIONS |
|---|---|---|
| Iridium(III) organometallic complexes | 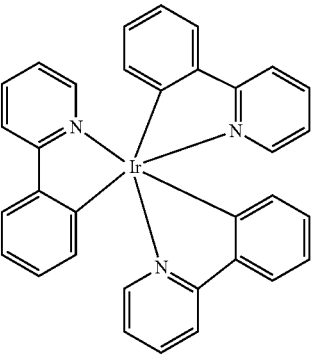<br>and its derivatives | Inorg. Chem. 40, 1704 (2001) |
| | 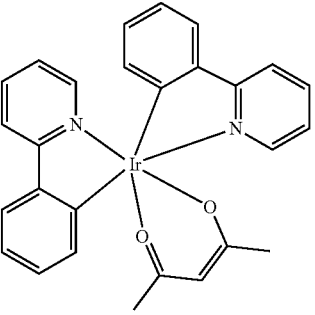 | US20020034656 |
| | 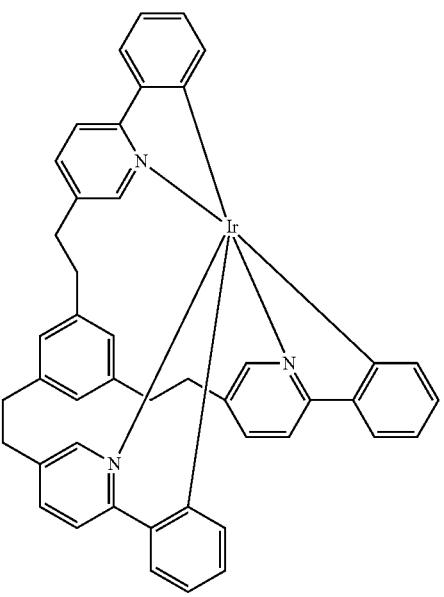 | U.S. Pat. No. 7,332,232 |
| | 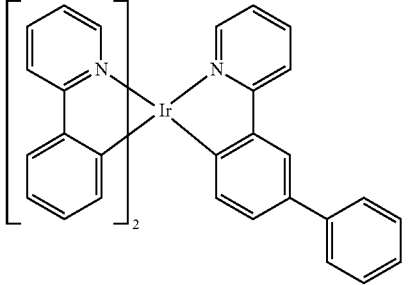 | US20090108737 |

TABLE 3-continued

| MATERIAL | EXAMPLES OF MATERIAL | PUBLICATIONS |
|---|---|---|
| | | US20090039776 |
| | | U.S. Pat. No. 6,921,915 |
| | | U.S. Pat. No. 6,687,266 |
| | | Chem. Mater. 16, 2480 (2004) |
| | | US20070190359 |

TABLE 3-continued

| MATERIAL | EXAMPLES OF MATERIAL | PUBLICATIONS |
|---|---|---|
| | | US 20060008670 <br> JP2007123392 |
| | | Adv. Mater. 16, 2003 (2004) |
| | | Angew. Chem. Int. Ed. 2006, 45, 7800 |
| | | WO2009050290 |
| | | US20090165846 |
| | | US20080015355 |

TABLE 3-continued

| MATERIAL | EXAMPLES OF MATERIAL | PUBLICATIONS |
| --- | --- | --- |
| Monomer for polymeric metal organometallic complexes | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 3-continued

| MATERIAL | EXAMPLES OF MATERIAL | PUBLICATIONS |
| --- | --- | --- |
|  | (Pt complex structure) | US20060263635 |
| Cu complexes | (Cu complex structure) | WO2009000673 |
| Gold complexes | (Au complex structure) | Chem. Commun. 2906 (2005) |
| Rhenium(II) complexes | (Re complex structure) | Inorg. Chem. 42, 1248 (2003) |

TABLE 3-continued

| MATERIAL | EXAMPLES OF MATERIAL | PUBLICATIONS |
| --- | --- | --- |
| Deuterated organometallic complexes | (deuterated Ir(ppy)₃ complex structure) | US20030138657 |
| Organometallic complexes with two or more metal centers | (dinuclear Ir complex structure) | US20030152802 |
| | (dinuclear Pt complex with fluorinated phenylpyridine and thiolate bridges) | U.S. Pat. No. 7,090,928 |
| Blue dopants | | |
| Iridium(III) organometallic complexes | (bis(difluorophenylpyridine) Ir picolinate structure) | WO2002002714 |

TABLE 3-continued
| MATERIAL | EXAMPLES OF MATERIAL | PUBLICATIONS |
|---|---|---|
| | 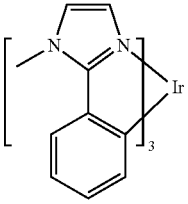 | WO2006009024 |
| | 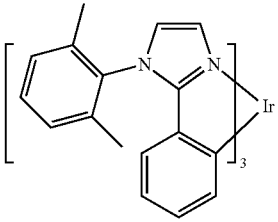 | US20060251923 |
| | 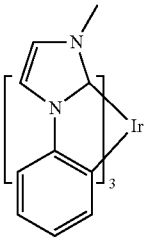 | U.S. Pat. No. 7,393,599, WO2006056418, US20050260441, WO2005019373 |
| | 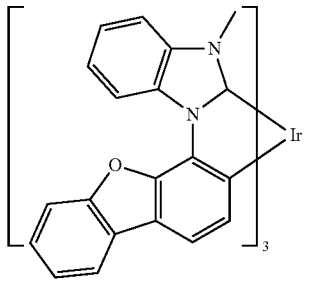 | U.S. Pat. No. 7,534,505 |
| | 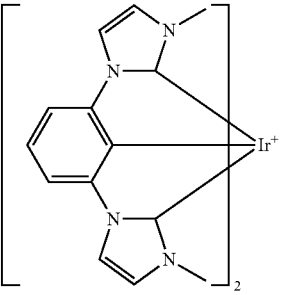 | U.S. Pat. No. 7,445,855 |
| | 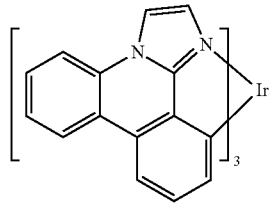 | US20070190359, US20080297033 |

| MATERIAL | EXAMPLES OF MATERIAL | PUBLICATIONS |
|---|---|---|
| | 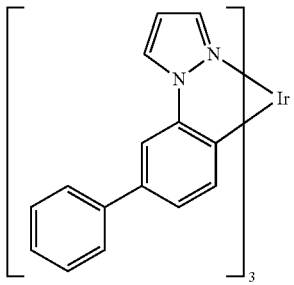 | U.S. Pat. No. 7,338,722 |
| | 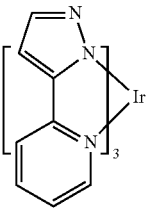 | US20020134984 |
| | 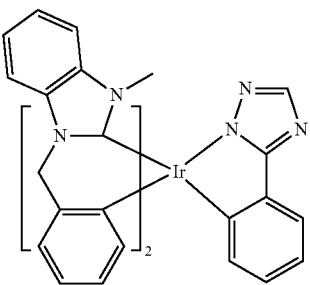 | Angew. Chem. Int. Ed. 47, 1 (2008) |
| | 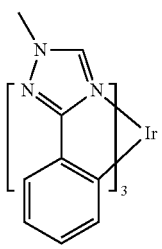 | Chem. Mater. 18, 5119 (2006) |
| | 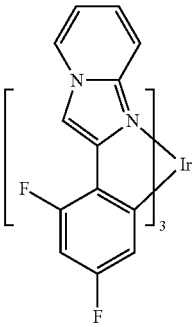 | Inorg. Chem. 46, 4308 (2007) |

TABLE 3-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 3-continued

| MATERIAL | EXAMPLES OF MATERIAL | PUBLICATIONS |
|---|---|---|
| | | Organometallics 23, 3745 (2004) |
| Gold complexes | | Appl. Phys. Lett. 74, 1361 (1999) |
| Platinum(II) complexes | | WO2006098120, WO2006103874 |
| Exciton/hole blocking layer materials | | |
| Bathocuprine complexes (e.g., BCP, BPhen) | | Appl. Phys. Lett. 75, 4 (1999) |
| | | Appl. Phys. Lett. 79, 449 (2001) |
| Metal 8-hydroxy-quinolates (e.g., BAlq) | | Appl. Phys. Lett. 81, 162 (2002) |

TABLE 3-continued
| MATERIAL | EXAMPLES OF MATERIAL | PUBLICATIONS |
| --- | --- | --- |
| 5-member ring electron deficient heterocycles such as triazole, oxadiazole, imidazole, benzoimidazole | 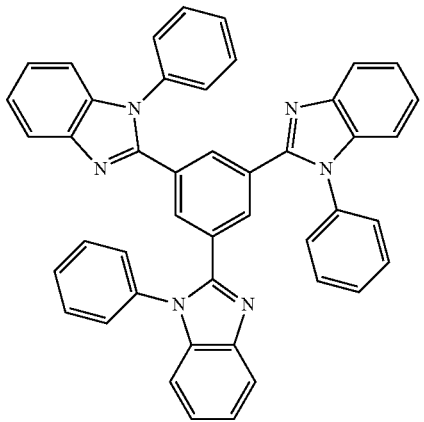 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene complexes | 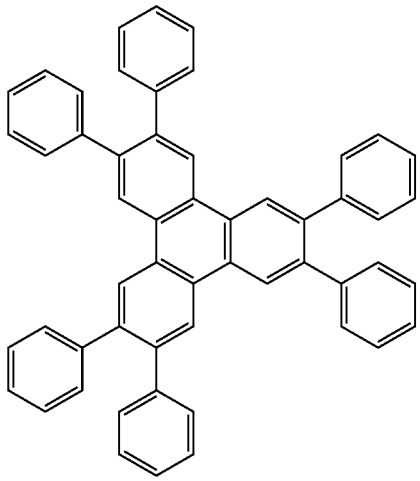 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic complexes | 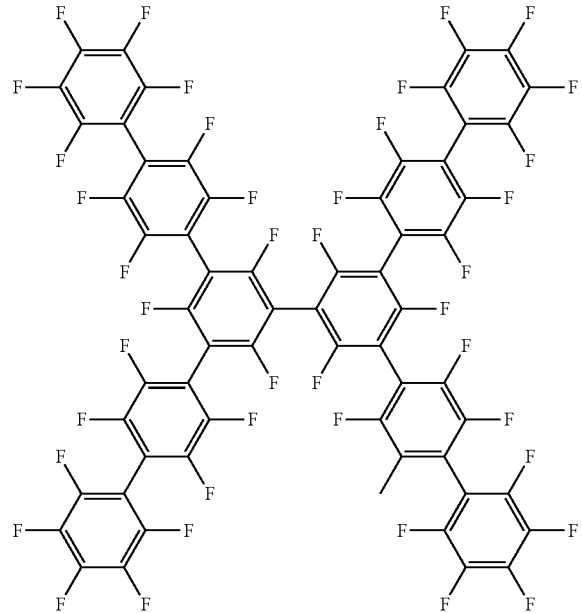 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 3-continued

| MATERIAL | EXAMPLES OF MATERIAL | PUBLICATIONS |
|---|---|---|
| Phenothiazine-S-oxide | | WO2008132085 |
| Electron transporting materials | | |
| Anthracene-benzoimidazole complexes | | WO2003060956 |
| | | US20090179554 |
| Aza triphenylene derivatives | | US20090115316 |
| Anthracene-benzothiazole complexes | | Appl. Phys. Lett. 89, 063504 (2006) |

TABLE 3-continued

| MATERIAL | EXAMPLES OF MATERIAL | PUBLICATIONS |
| --- | --- | --- |
| Metal 8-hydroxy-quinolates (e.g., $Alq_3$, $Zrq_4$) | | Appl. Phys. Lett. 51, 913 (1987) U.S. Pat. No. 7,230,107 |
| Metal hydroxy-benoquinolates | | Chem. Lett. 5, 905 (1993) |
| Bathocuprine complexes such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE 3-continued
| MATERIAL | EXAMPLES OF MATERIAL | PUBLICATIONS |
|---|---|---|
| | 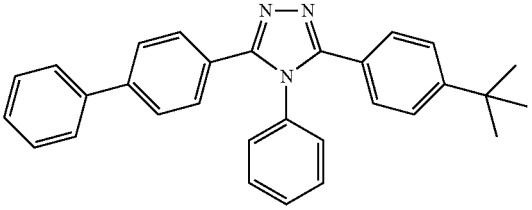 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole complexes | 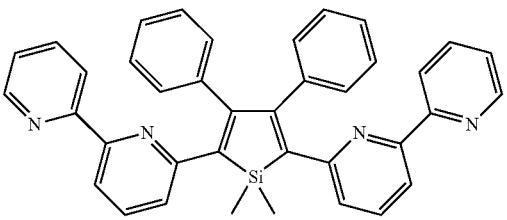 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane complexes | 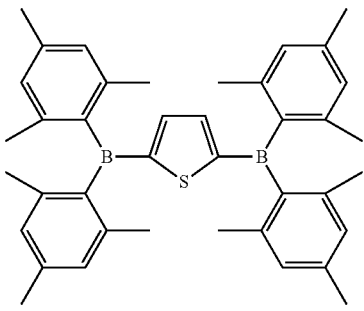 | J. Am. Chem. Soc. 120, 9714 (1998) |
| Fluorinated aromatic complexes | 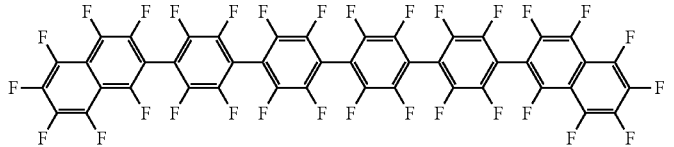 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 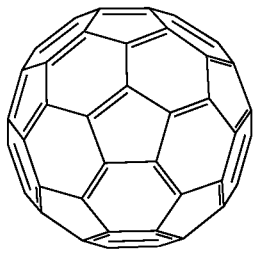 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 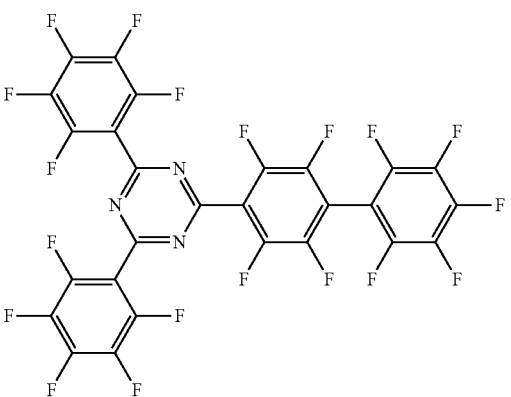 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

| MATERIAL | EXAMPLES OF MATERIAL | PUBLICATIONS |
| --- | --- | --- |
| Zn (N^N) complexes | | U.S. Pat. No. 6,528,187 |

EXPERIMENTAL

Complex Examples

Several of the complexes were synthesized as follows:

Example 1. Synthesis of Complex 1

Chloro[1,3-bis(2,6-di-1-propylphenyl)imidazol-2-ylidene]copper(I) (487.59 mg, 0.25 mmol) and silver triflate (64.2 mg, 0.25 mmol) were mixed under nitrogen in 25 mL flask and 10 mL of dry THF were added. Reaction mixture was stirred at RT for 30 minutes. Solution of 1,2-bis(diphenylphosphino)benzene (111.6 mg, 0.25 mmol) in dry THF (5 mL) was added. Reaction mixture was stirred at RT overnight. Resulting mixture was filtered through Celite® and solvent was evaporated on rotovap. Recrystallization from $CH_2Cl_2$ by vapor diffusion of $Et_2O$ gave 130 mg (49.6%) of white needle crystals. Structure confirmed by $^1$H-NMR spectrum of [(IPR)Cu(dppbz)]OTf ($CDCl_3$, 400 MHz).

Example 2. Synthesis of Complex 2

Chloro[1,3-bis(2,6-di-1-propylphenyl)imidazol-2-ylidene]copper(I) (121.9 mg, 0.25 mmol) and silver triflate (64.2 mg, 0.25 mmol) were mixed under nitrogen in 25 mL flask and 10 mL of dry THF were added. Reaction mixture was stirred at RT for 30 minutes. Solution of 1,10-phenanthroline (45.05 mg, 0.25 mmol) in dry THF (5 mL) was added. Reaction mixture turned yellow and was stirred at RT overnight. Resulting mixture was filtered through Celite® and solvent was evaporated on rotovap. Recrystallization from $CH_2Cl_2$ by vapor diffusion of $Et_2O$ gave 120 mg (61.4%) of yellow crystals. Anal. calcd. for $C_{40}H_{44}CuF_3N_4O_3S$: C, 61.48; H, 5.68; N, 7.17. Found: C, 61.06; H, 5.61; N, 7.14. Structure was confirmed by $^1$H-NMR spectrum of [(IPR)Cu(phen)]OTf ($CDCl_3$, 400 MHz).

Example 3. Synthesis of Complex 3

Chloro[1,3-bis(2,6-di-1-propylphenyl)imidazol-2-ylidene]copper(I) (195.1 mg, 0.4 mmol) and silver triflate (102.7 mg, 0.4 mmol) were mixed under nitrogen in 25 mL flask and 10 mL of dry THF were added. Reaction mixture was stirred at RT for 30 minutes. Solution of 2,2'-bipyridine (62.4 mg, 0.4 mmol) in dry THF (5 mL) was added. Reaction mixture turned orange and was stirred at RT overnight. Resulting mixture was filtered through Celite® and solvent was evaporated on rotovap. Recrystallization from $CH_2Cl_2$ by vapor diffusion of $Et_2O$ gave 215 mg (70.9%) of orange crystals. Anal. calcd. for $C_{38}H_{44}CuF_3N_4O_3S$: C, 60.26; H, 5.86; N, 7.40; Found: C, 60.18; H, 5.82; N, 7.38. Structure was confirmed by $^1$H-NMR spectrum of [(IPR)Cu(bipy)]OTf ($CDCl_3$, 400 MHz).

Example 4. Synthesis of Complex 4

2-(2-Pyridyl)benzimidazole (78.1 mg, 0.4 mmol) was dissolved in 10 mL of dry THF under $N_2$ and this solution was transferred via cannula to suspension of sodium hydride (17.6 mg, 0.44 mmol, 60% in mineral oil) in dry THF. Reaction mixture was stirred at RT for 1 h and then chloro[1,3-bis(2,6-di-1-propylphenyl)imidazol-2-ylidene]copper(I) (195.1 mg, 0.4 mmol) was added. Reaction mixture was stirred at RT for 3 h. The resulting mixture was filtered through Celite® and solvent was removed by rotary evaporation. Recrystallization by vapor diffusion of $Et_2O$ into a $CH_2Cl_2$ solution of product gave 154 mg (59.5%) of dark yellow crystals. Anal. calcd. for $C_{39}H_{44}CuN_5$: C, 72.47; H, 6.86; N, 10.48. Found: C, 72.55; H, 6.94; N, 10.84.

Example 5. Synthesis of Complex 5

1-(1H-benzimidazol-2-yl)-isoquinoline (46 mg, 0.19 mmol) was dissolved in 10 mL of dry THF under $N_2$ and this solution was transferred via cannula to suspension of sodium hydride (8.36 mg, 0.209 mmol, 60% in mineral oil) in dry THF. The reaction mixture was stirred at RT for 1 h and then chloro[1,3-bis(2,6-di-1-propylphenyl)imidazol-2-ylidene]copper(I) (92.6 mg, 0.19 mmol) was added. The reaction mixture was stirred at RT for 3 h. The resulting mixture was filtered through Celite® and solvent was removed by rotary evaporation. Recrystallization by vapor diffusion of $Et_2O$ into a $CH_2Cl_2$ solution of product gave 50 mg (38%) of orange crystals.

Example 6. Synthesis of Complex 6

2-(2-Pyridyl)benzimidazole (78.1 mg, 0.4 mmol) was dissolved in 10 mL of dry THF under $N_2$ and this solution was transferred via cannula to suspension of sodium hydride (17.6 mg, 0.44 mmol, 60% in mineral oil) in dry THF. The reaction mixture was stirred at RT for 1 h and then chloro [1,3-bis(2,4,6-trimethylphenyl)imidazol-2-ylidene]copper (I) (161.4 mg, 0.4 mmol) was added. The reaction mixture was stirred at RT for 3 h. The resulting mixture was filtered through Celite®. Solvent was removed by rotary evaporation and 178 mg (79%) of light-yellow solid was obtained.

Example 7. Synthesis of Complex 7

Sodium dimethylbis(2-pyridyl)borate Na[(CH$_3$)$_2$B(py)$_2$] (66 mg, 0.3 mmol) and chloro[1,3-bis(2,6-di-1-propylphenyl)-4,5-dihydroimidazol-2-ylidene]copper(I) (SIPr)CuCl (146.9 mg, 0.3 mmol) were mixed under N$_2$ atmosphere in 25 mL flask. Freshly distilled THF (10 ml) was added and reaction mixture was stirred at RT for 1 h. Resulting mixture was filtered through Celite® and solvent was evaporated on rotovap. Recrystallization from acetone/hexane gave 85 mg (43.5%) of white solid. $^1$H-NMR (acetone-d$_6$, 400 MHz, ppm): δ −0.28 (s, 6H), 1.14 (d, 12H), 1.32 (d, 12H), 3.56 (sept, 4H), 4.21 (s, 4H), 6.56-6.60 (m, 2H), 7.20 (td, 2H), 7.27-7.30 (m, 6H), 7.38 (t, 2H), 7.50 (d, 2H).

Example 8. Synthesis of Complex 8

Sodium dimethylbis(2-pyridyl)borate Na[(CH$_3$)$_2$B(py)$_2$] (68.7 mg, 0.312 mmol) and chloro[1,3-bis(2,4,6-trimethylphenyl)imidazol-2-ylidene]copper(I) (106 mg, 0.26 mmol) were mixed under N$_2$ atmosphere in 25 mL flask. Freshly distilled THF (10 ml) was added and reaction mixture was stirred at RT for 1 h. Solvent was evaporated on rotovap. The crude solid was washed with hexane, redissolved in CH$_2$Cl$_2$ and filtered. Removal of solvent gave 90 mg (61.3%) of white solid. $^1$H-NMR (acetone-d$_6$, 400 MHz, ppm): δ −0.13 (broad d, 6H), 2.21 (s, 12H), 2.30 (s, 6H), 6.57-6.60 (m, 2H), 7.02 (s, 4H), 7.23 (td, 2H), 7.34 (d, 2H), 7.44 (s, 2H), 7.52 (d, 2H).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:
1. A first device comprising an organic light emitting device, further comprising:
   an anode;
   a cathode; and
   an organic layer, disposed between the anode and the cathode, the organic layer comprising an emissive dopant and a first host material comprising a carbene ligand coordinated to a three coordinate copper atom, wherein the first host material has the formula:

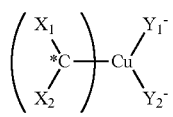

wherein Cu is a monovalent copper atom;
   wherein the carbene represented by X$_1$—C*—X$_2$ is a monodentate ligand selected from the group consisting of

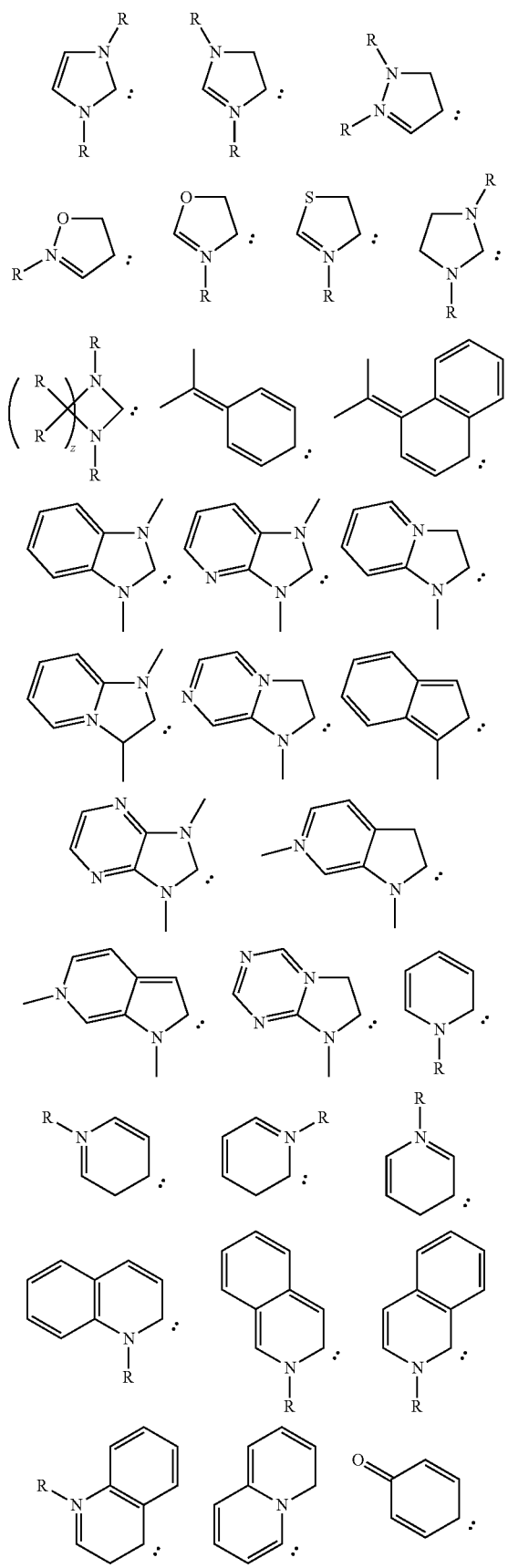

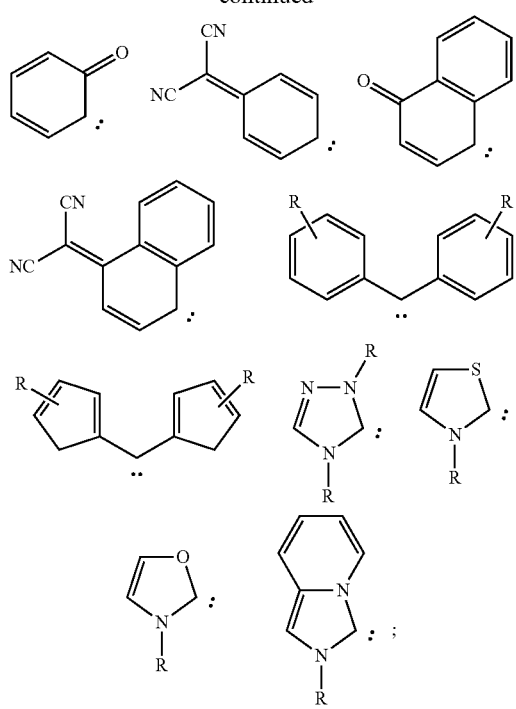
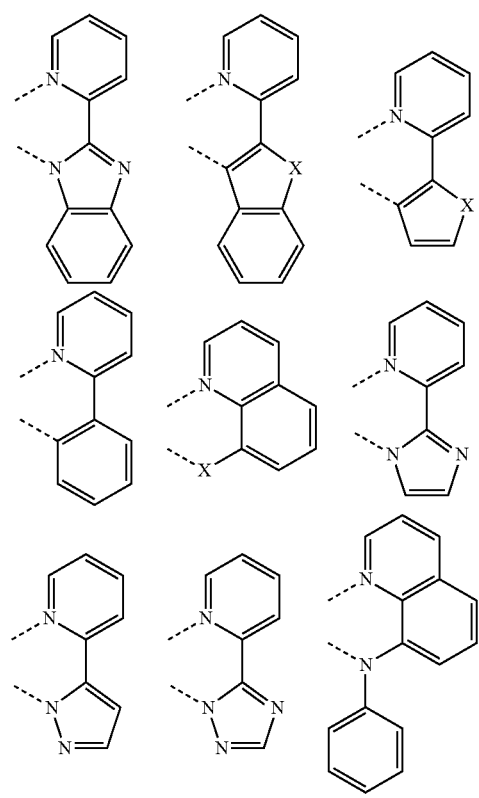
wherein z is 1, 2, 3, or 4;
wherein each of $Y_1$ and $Y_2$ form a bond with Cu;
wherein at least one of (i) to (x) is true:
(i) $Y_1$-$Y_2$ is selected from the group consisting of:
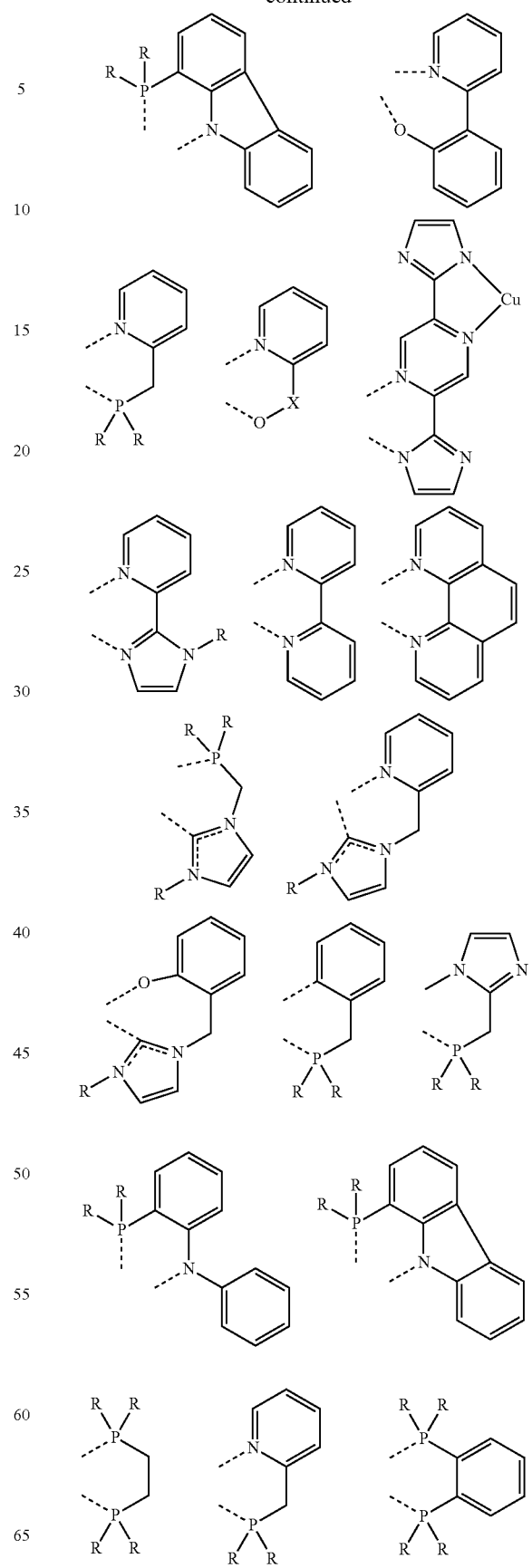

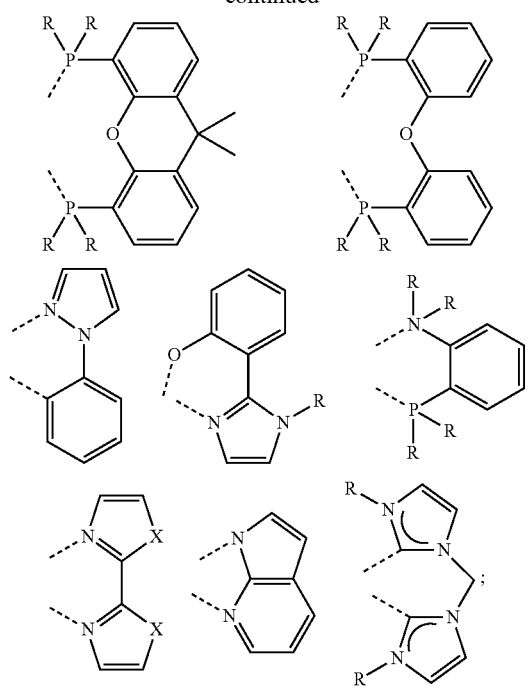
(ii) $Y_1$-$Y_2$ is selected from the group consisting of:
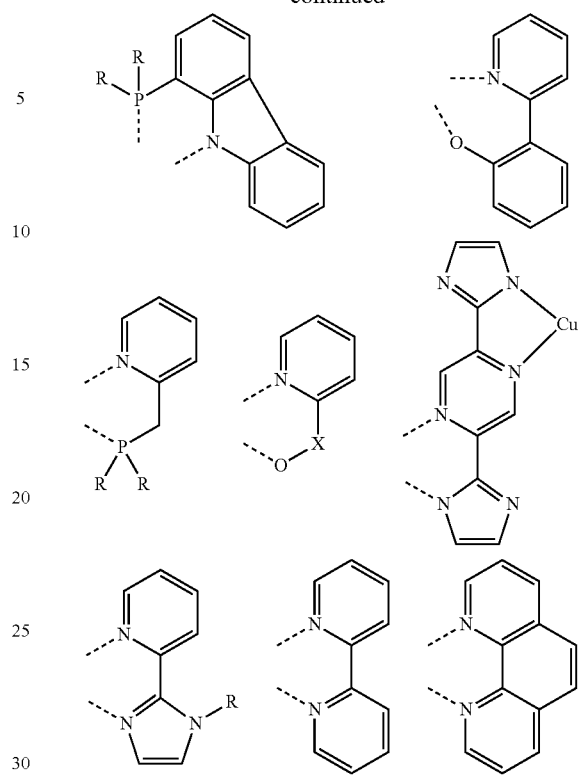
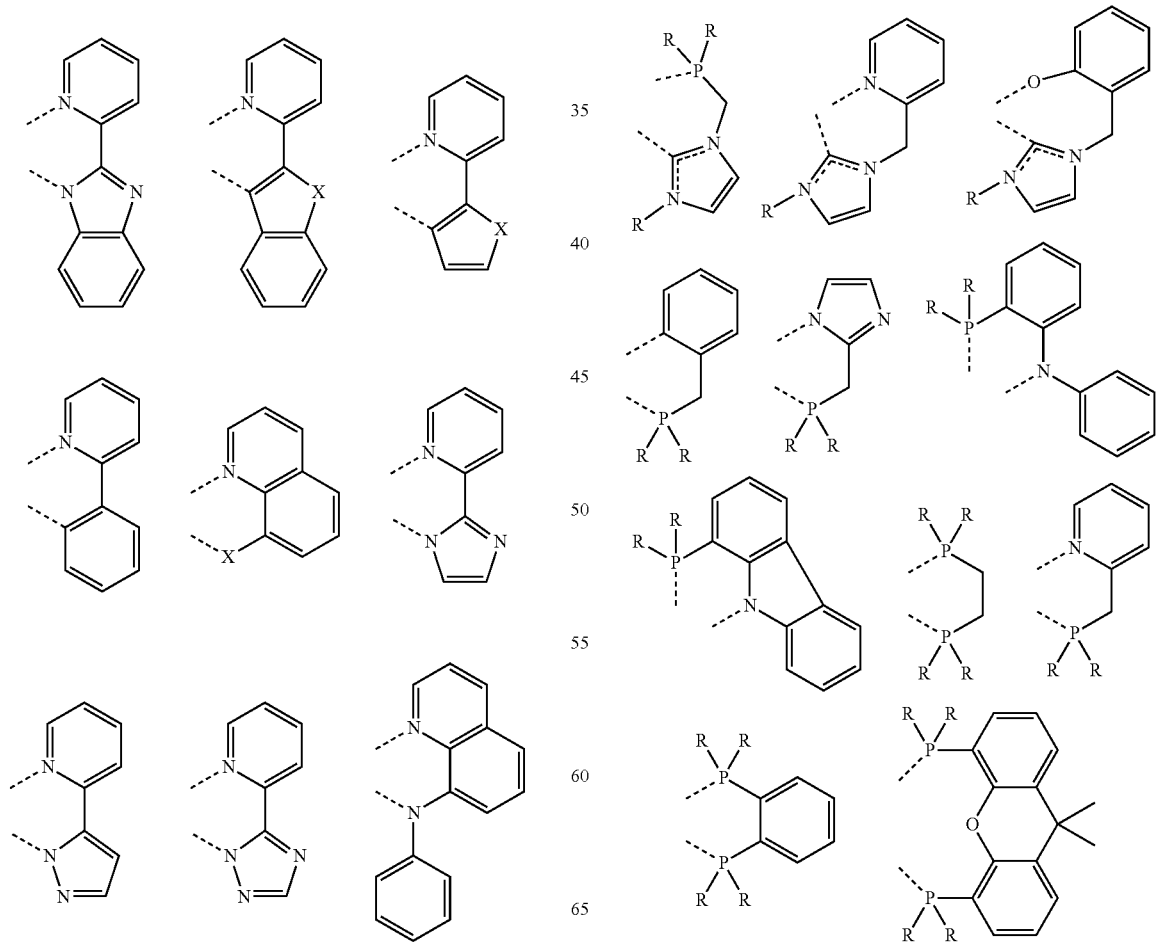

-continued
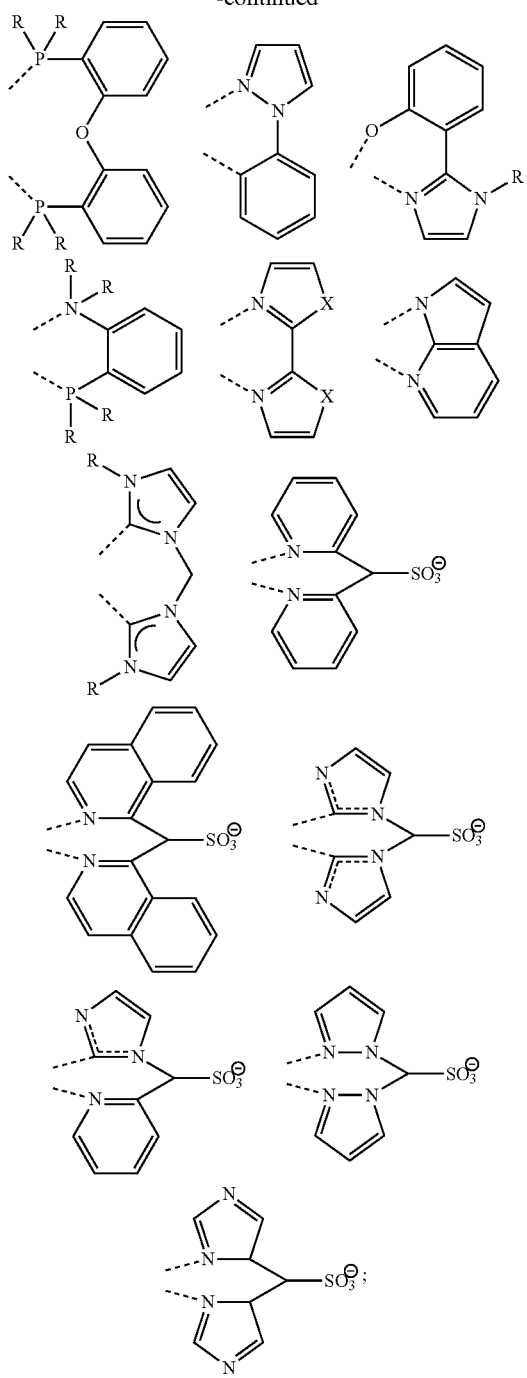
(iii) $Y_1$ is
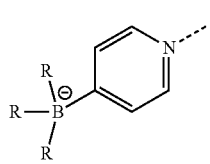
and
$Y_2$ is a monodentate ligand selected from the group consisting of
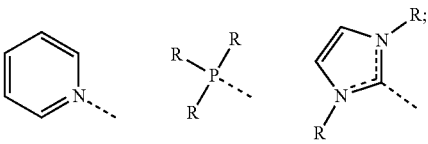
(iv) $Y_1$-$Y_2$ is selected from the group consisting of:
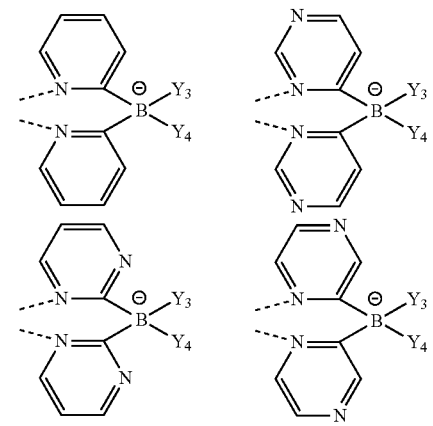
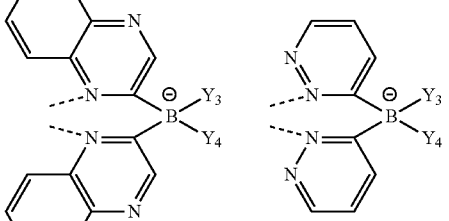
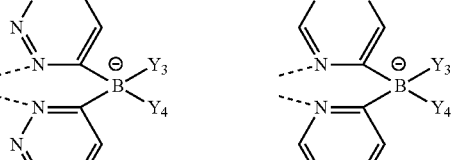
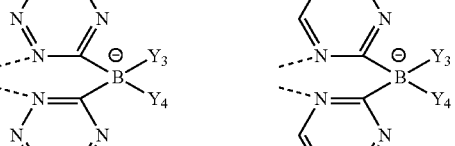
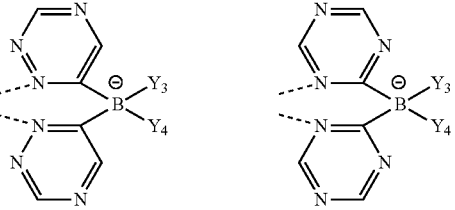

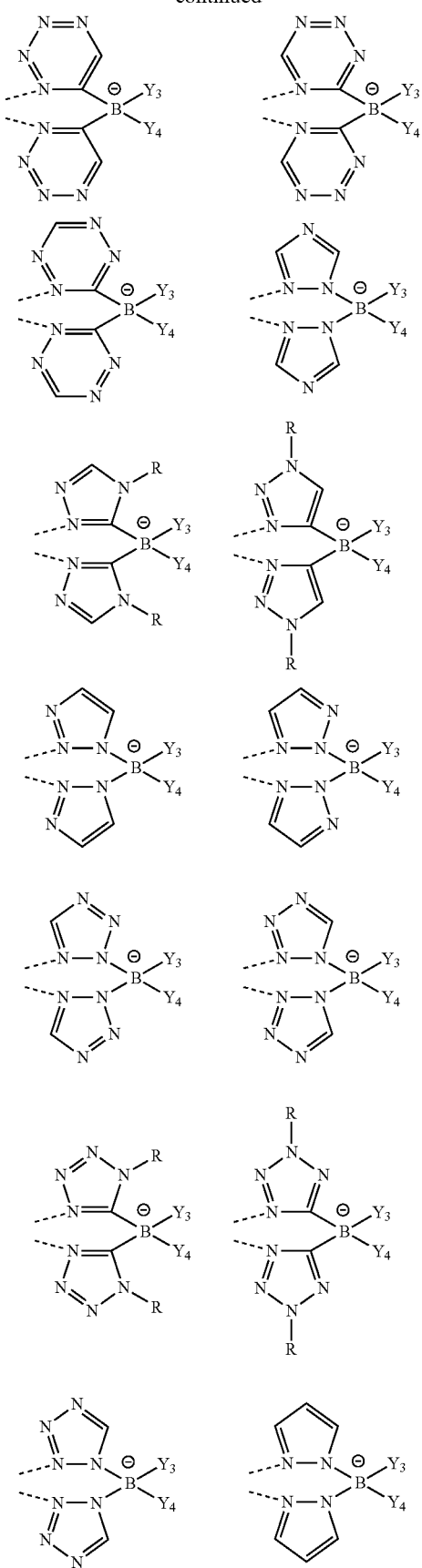
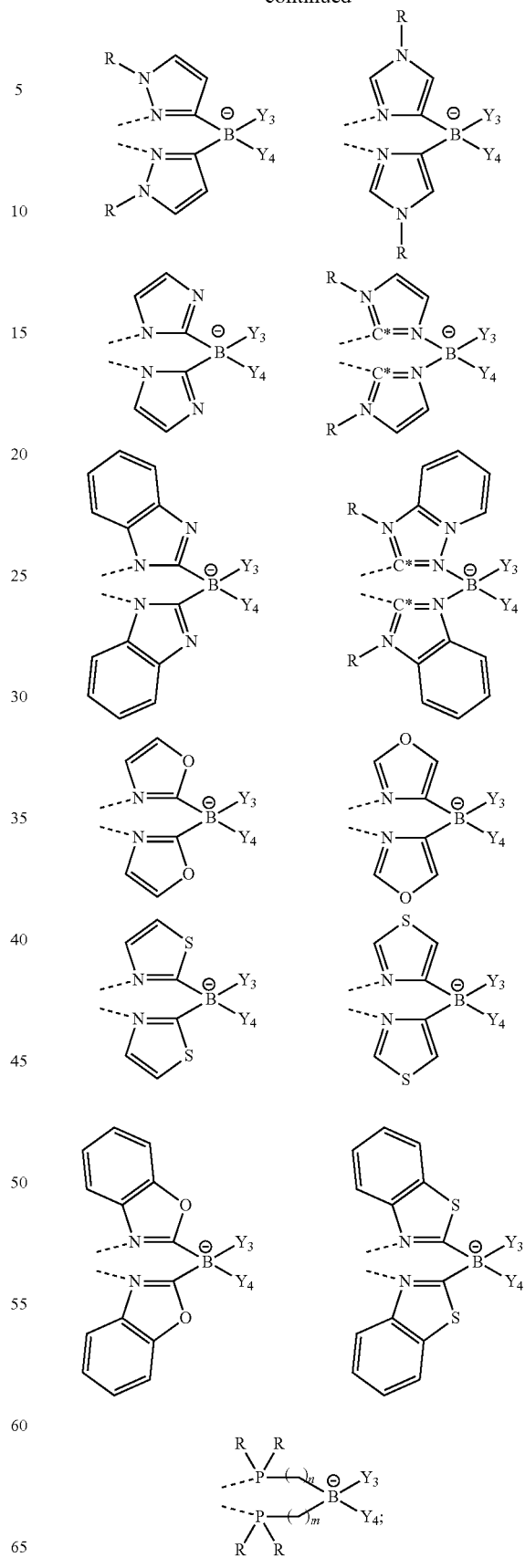

(v) Y$_1$-Y$_2$ is selected from the group consisting of:
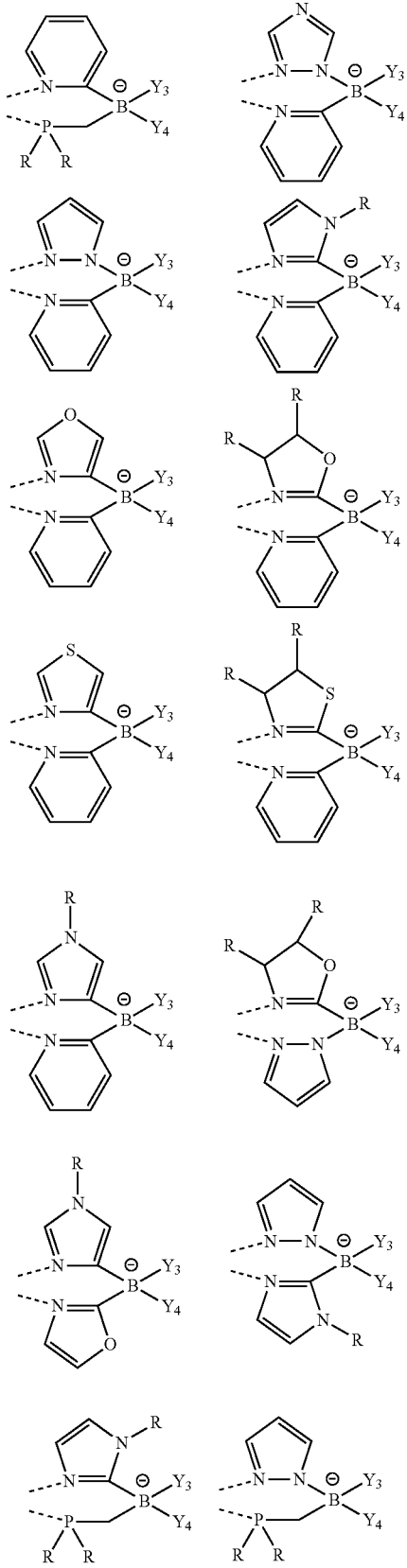
-continued
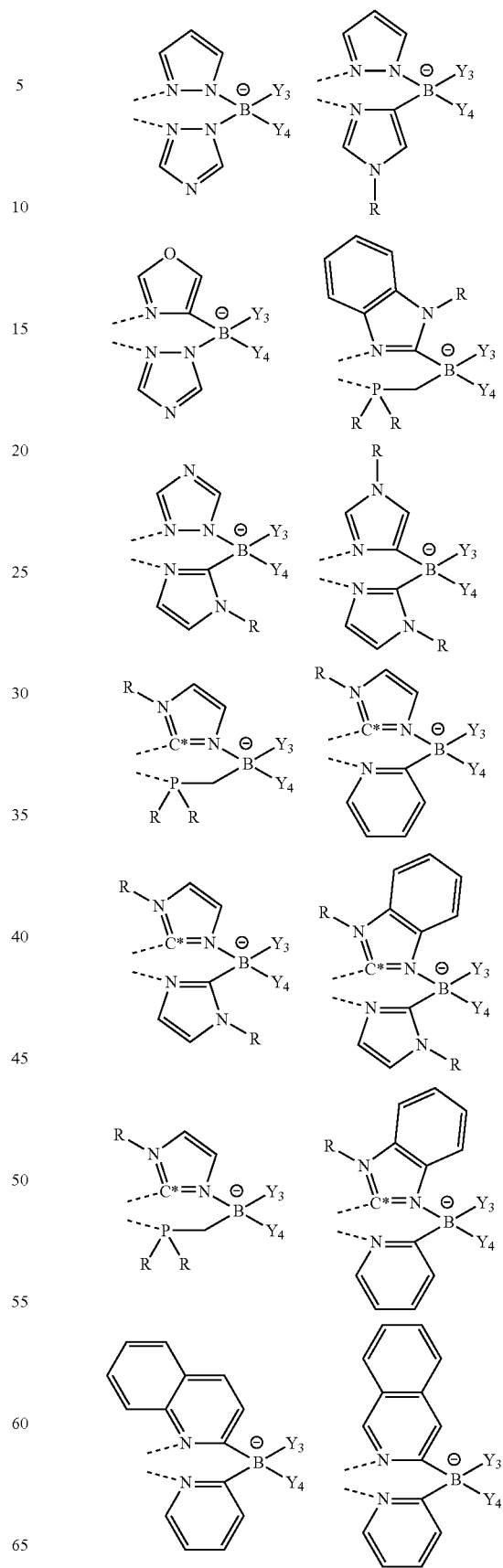

-continued
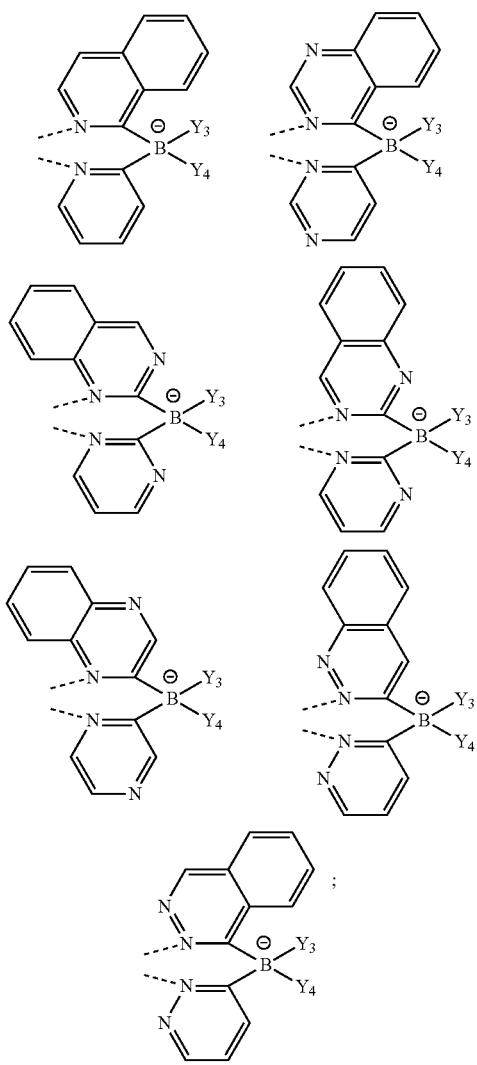
(vi) $Y_1$-$Y_2$ is selected from the group consisting of:
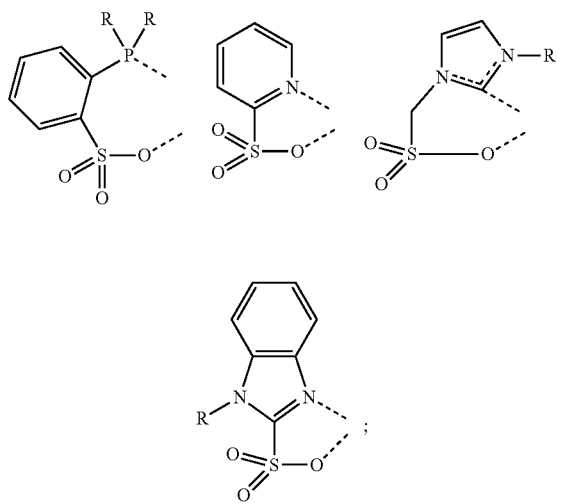
(vii) $Y_1$-$Y_2$ is selected from the group consisting of:
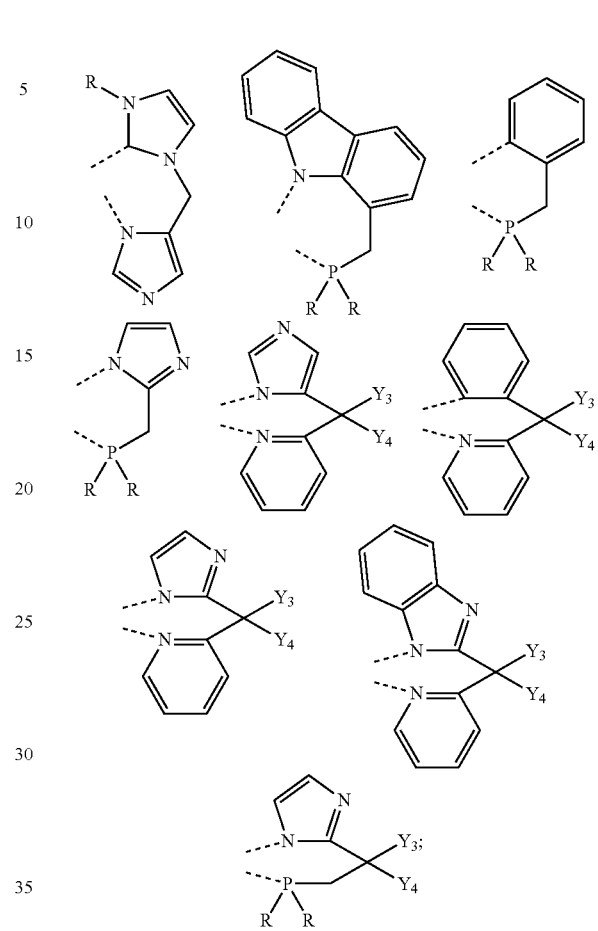
(viii) $Y_1$-$Y_2$ is selected from the group consisting of:
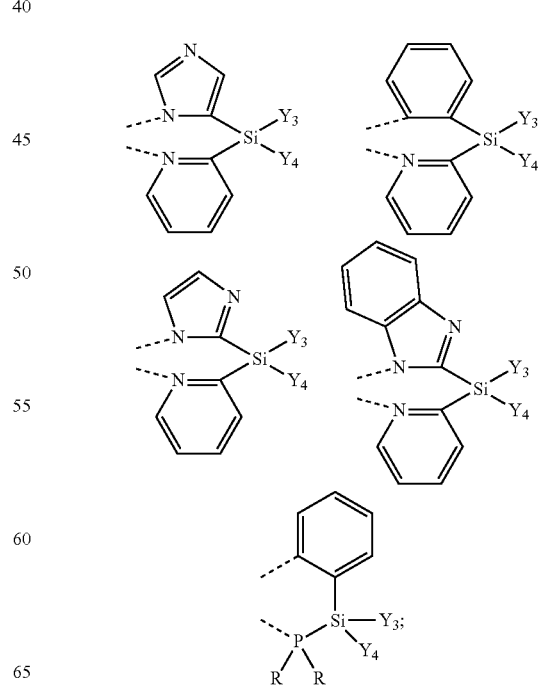

(ix) $Y_1$-$Y_2$ is selected from the group consisting of:

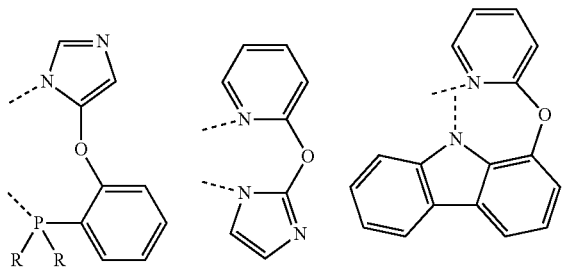

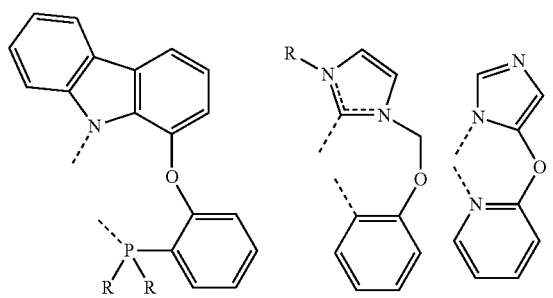

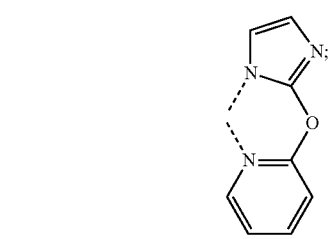

and (x) $Y_1$-$Y_2$ is selected from the group consisting of:

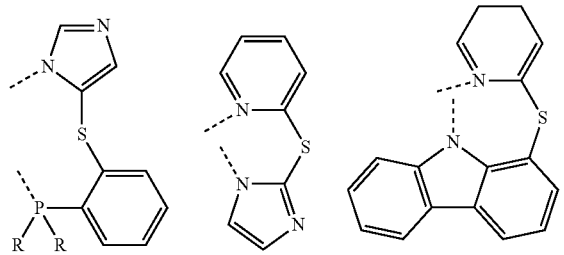

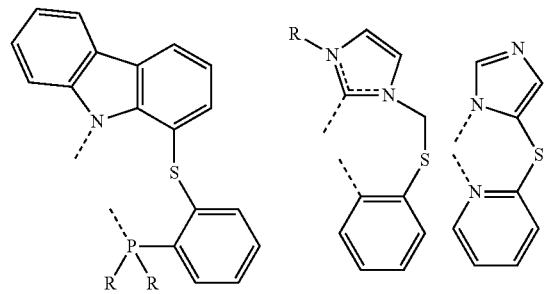

-continued

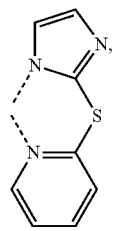

wherein, when present,

X is selected from the group consisting of NR, O, S, Se, $CR_2$, and CO;

each R is independently selected from the group consisting of hydrogen, alkyl, alkoxy, amino, alkenyl, alkynyl, arylalkyl, heteroalkyl, aryl, and heteroaryl;

$Y_3$ and $Y_4$ are independently selected from the group consisting of hydrogen, alkyl, aryl, alkoxy, amino, alkenyl, alkynyl, arylalkyl, heteroalkyl, and heteroaryl;

$Y_3$ and $Y_4$ are optionally joined to form a cycle, which may be extended by fusion n is 0, 1, or 2, and m is 0, 1, or 2.

2. The device of claim 1, wherein $Y_1$-$Y_2$ is selected from the group consisting of:

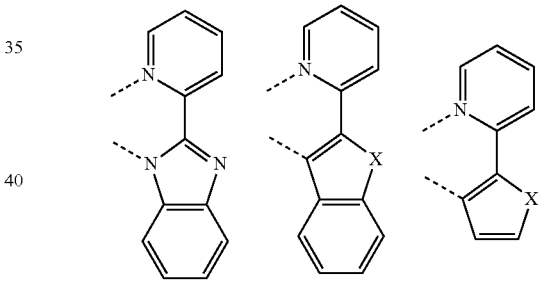

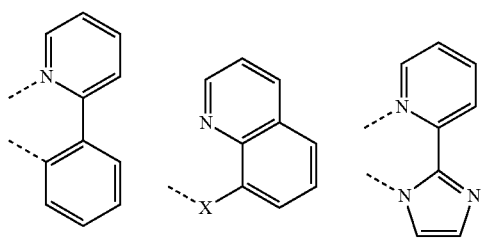

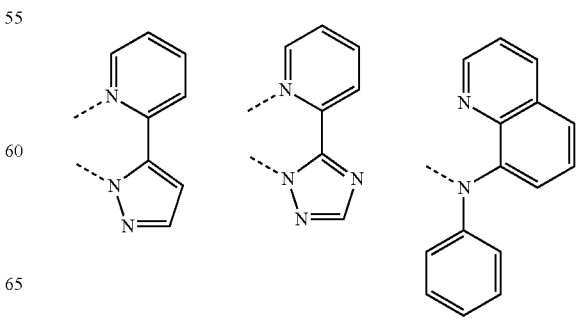

-continued
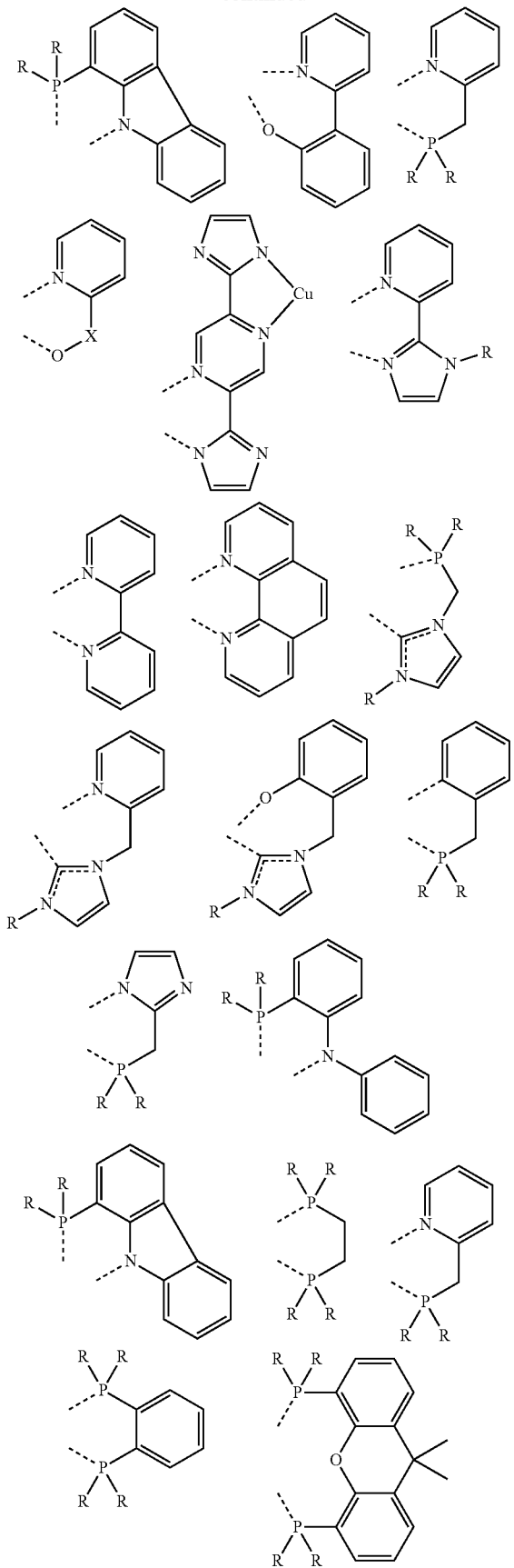
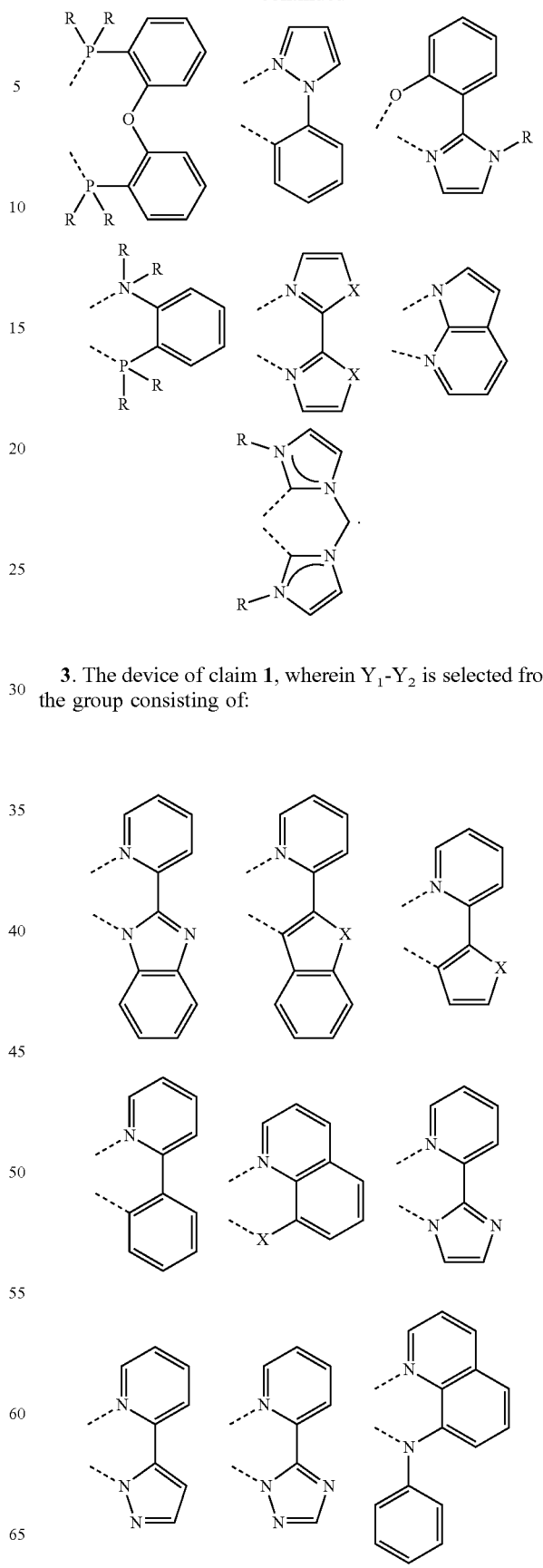
3. The device of claim 1, wherein $Y_1$-$Y_2$ is selected from the group consisting of:

-continued
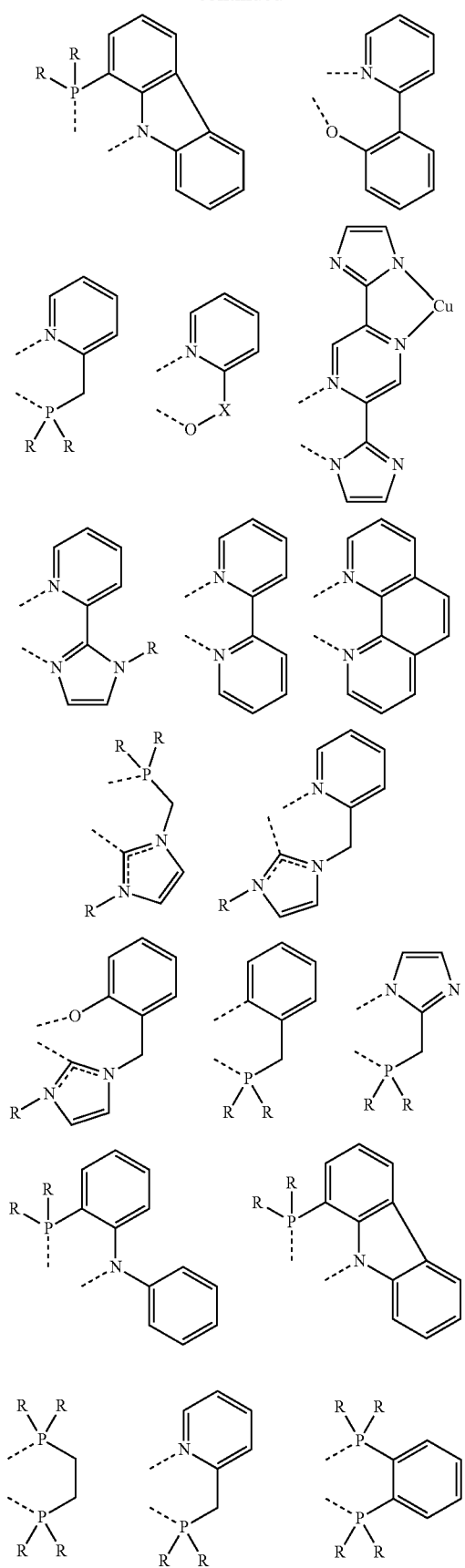
-continued
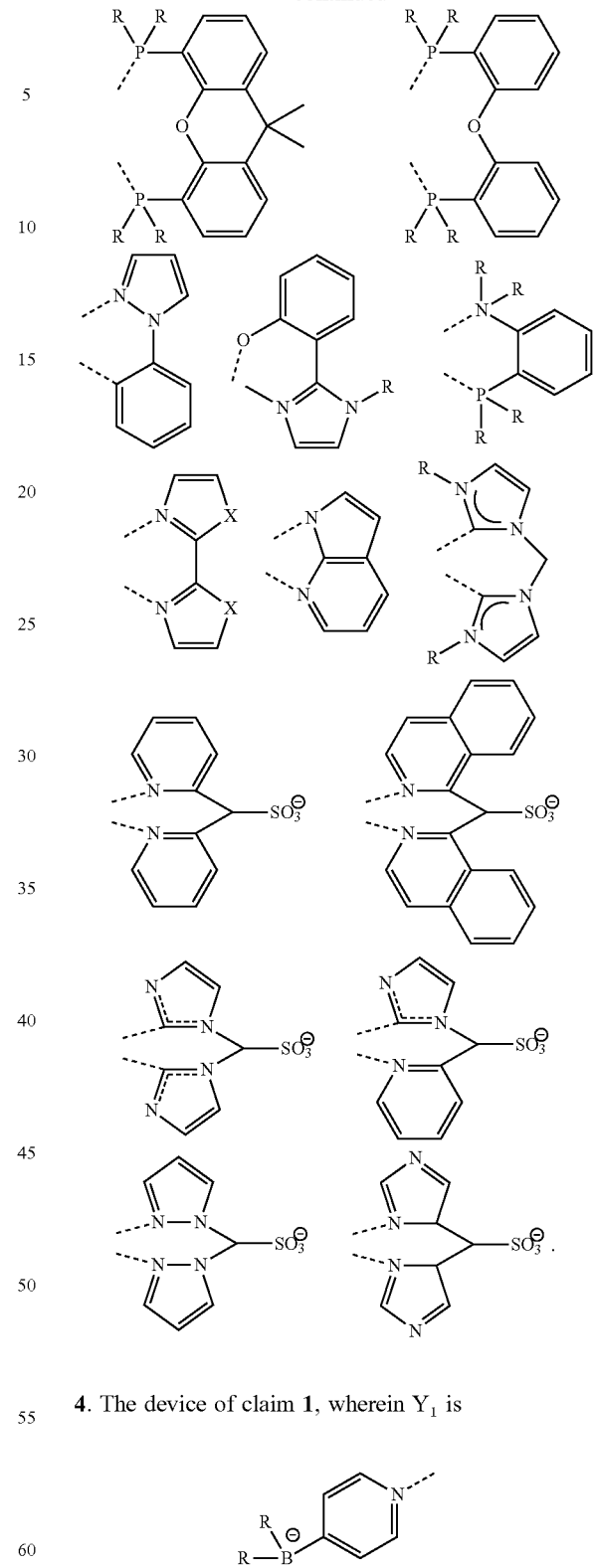
4. The device of claim 1, wherein $Y_1$ is
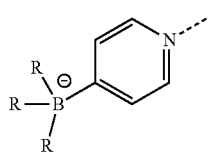
and
$Y_2$ is a monodentate ligand selected from the group consisting of

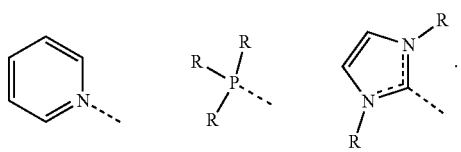
5. The device of claim 1, wherein $Y_1$-$Y_2$ is selected from the group consisting of:
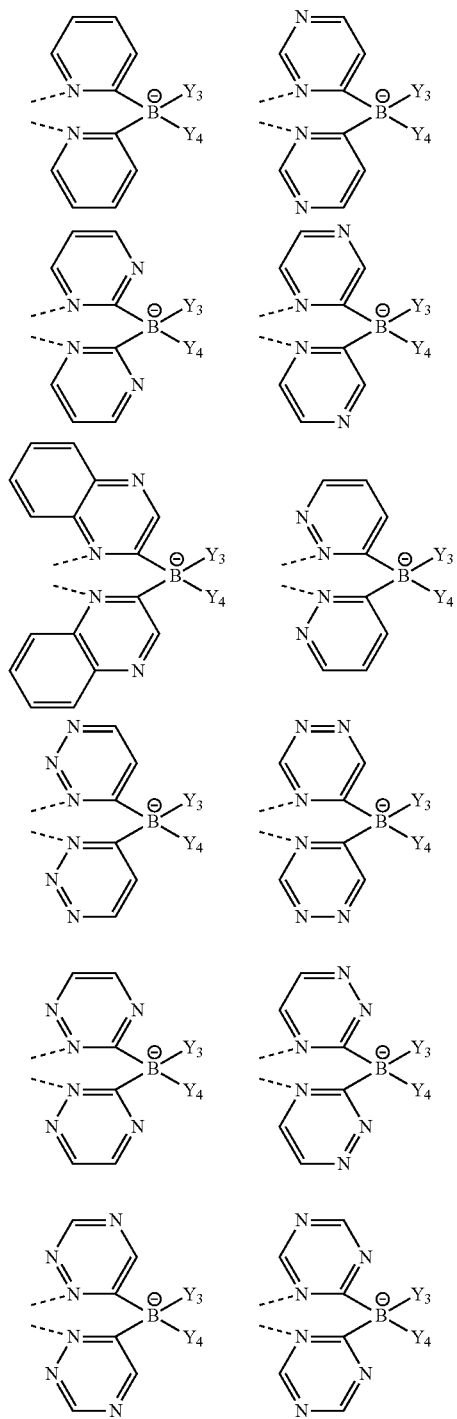
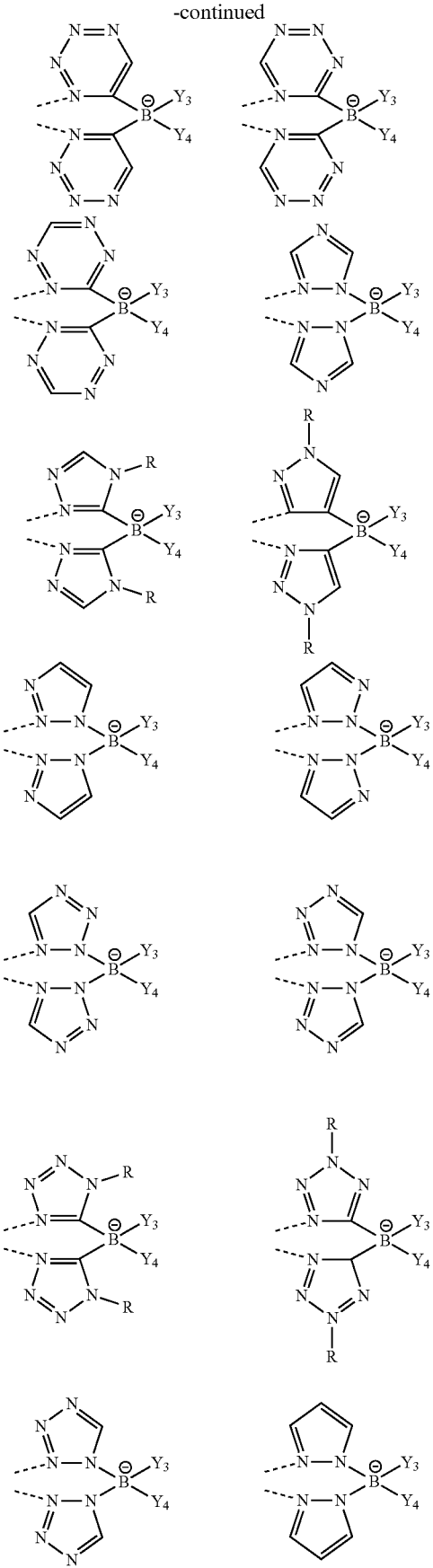

-continued
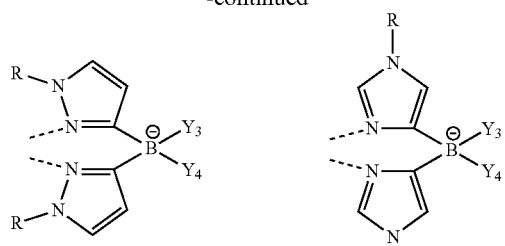
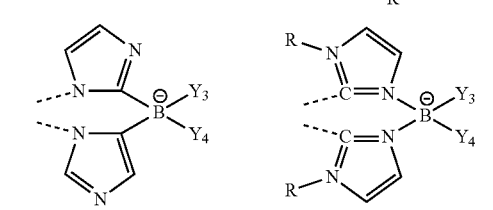
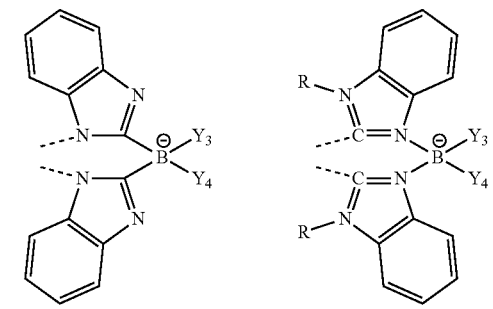
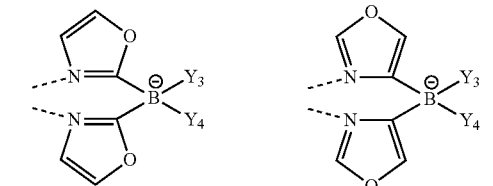
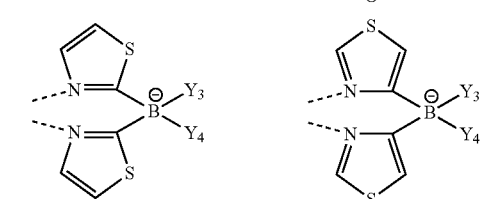
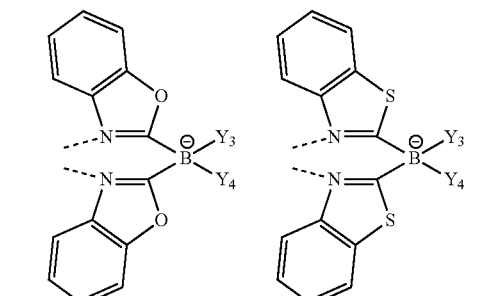
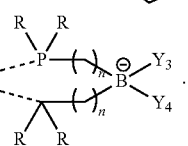
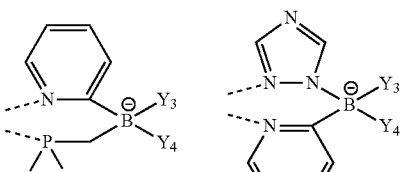
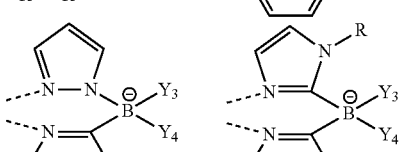
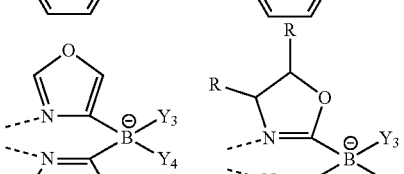
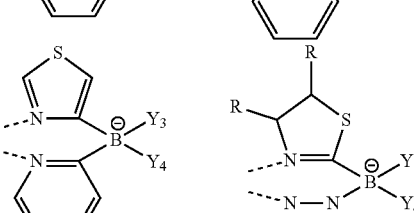
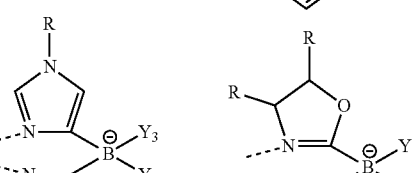
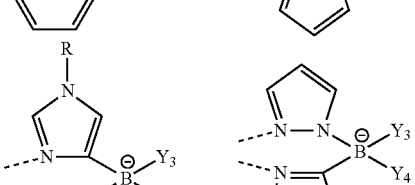
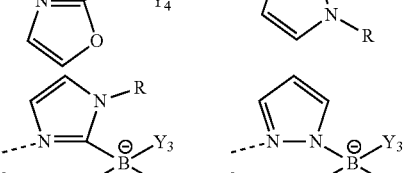
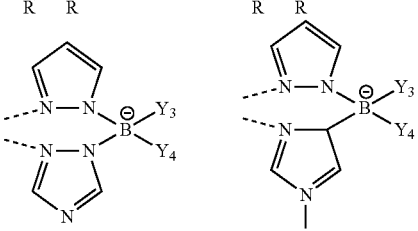
6. The device of claim 1, wherein $Y_1$-$Y_2$ is selected from the group consisting of:

-continued
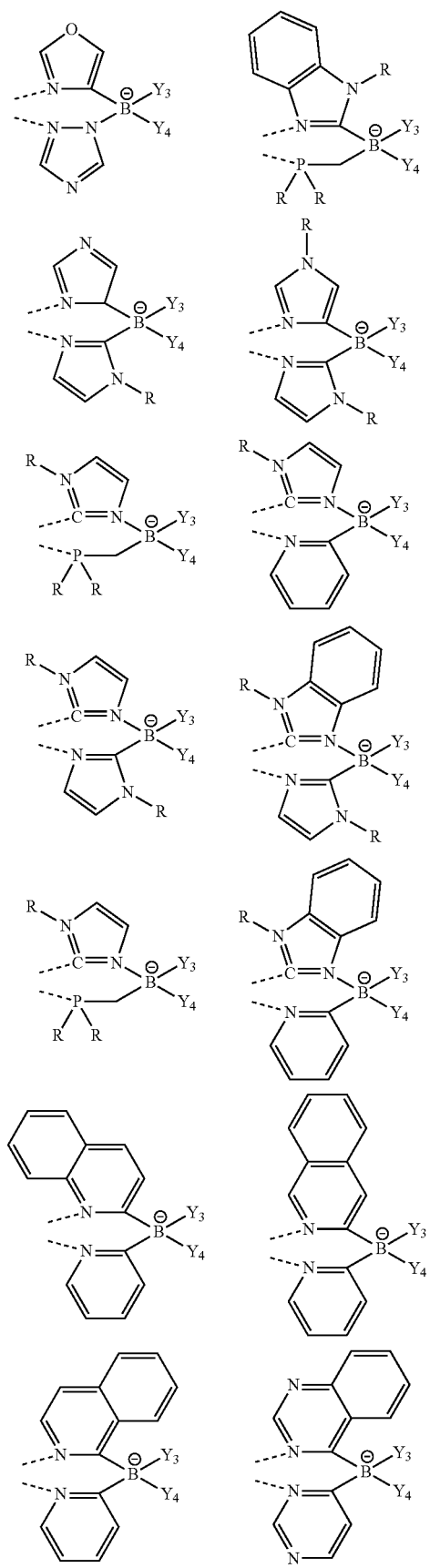
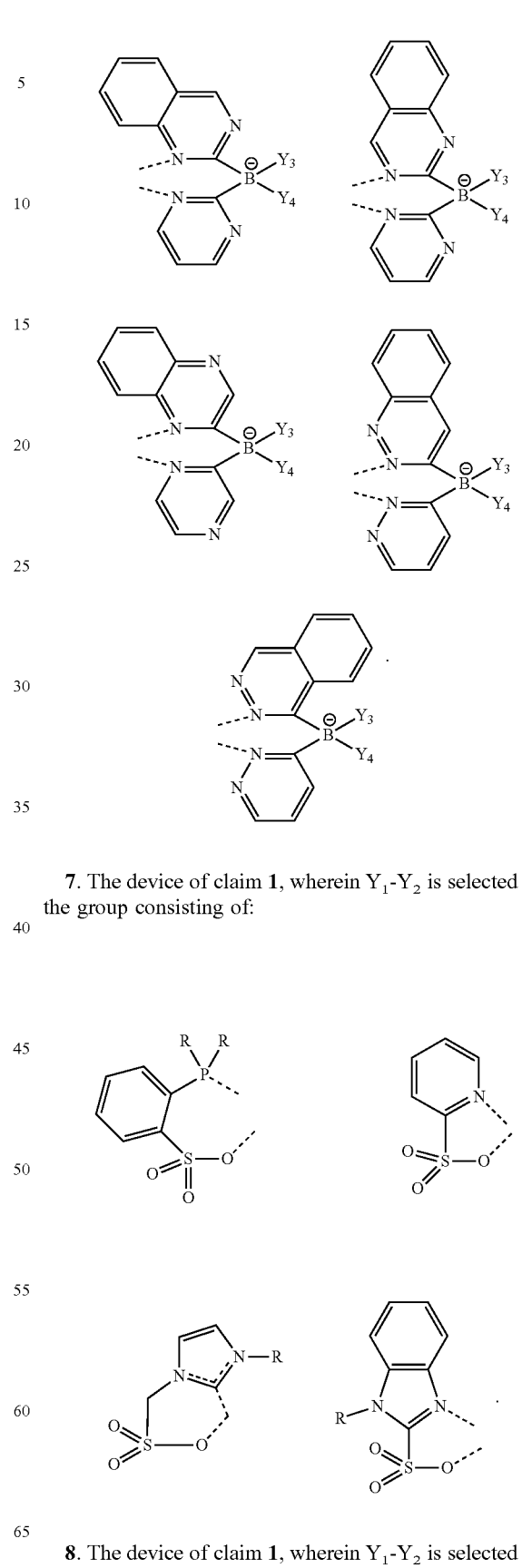
7. The device of claim 1, wherein $Y_1$-$Y_2$ is selected from the group consisting of:
8. The device of claim 1, wherein $Y_1$-$Y_2$ is selected from the group consisting of:

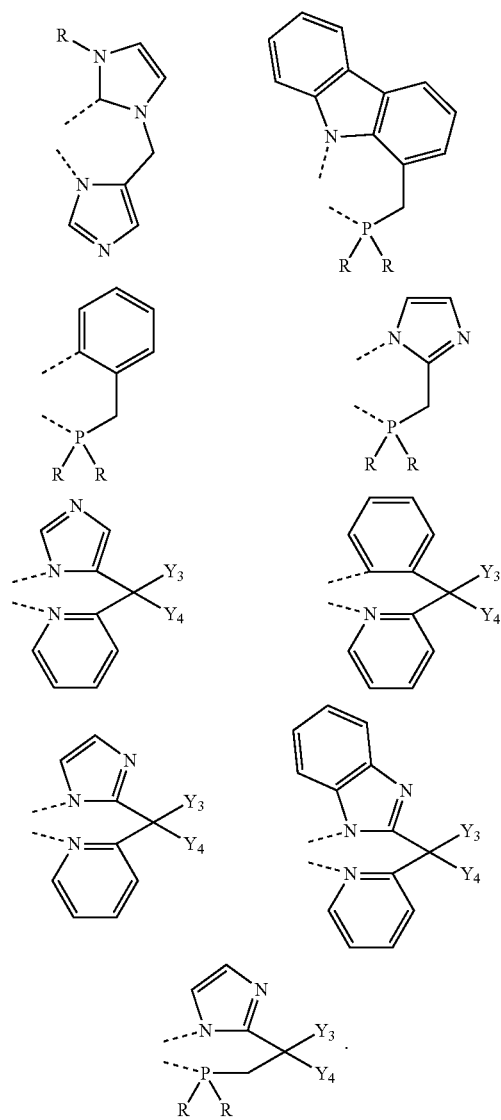
9. The device of claim 1, wherein $Y_1$-$Y_2$ is selected from the group consisting of:
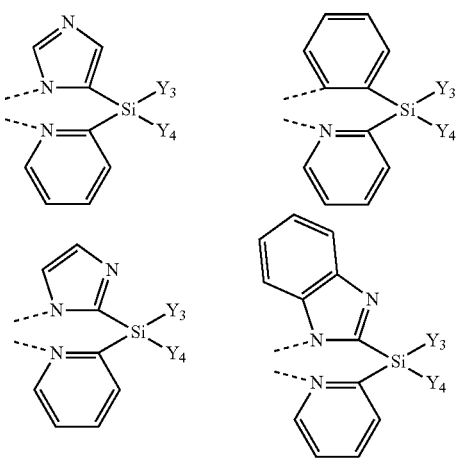
10. The device of claim 1, wherein $Y_1$-$Y_2$ is selected from the group consisting of:
11. The device of claim 1, wherein $Y_1$-$Y_2$ is selected from the group consisting of:
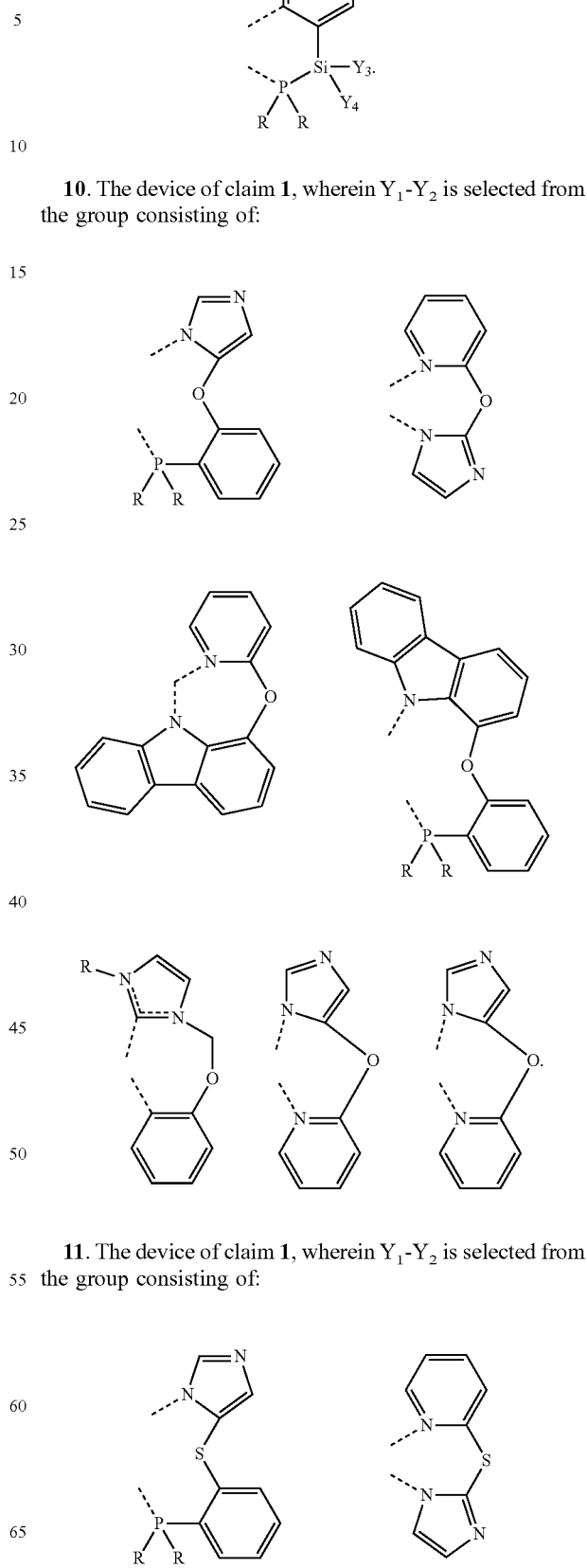

151
-continued

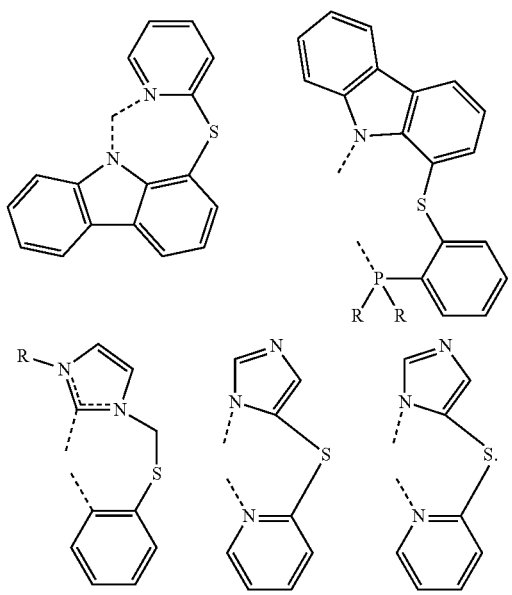

12. The device of claim 1, wherein the first host meets one of option (iv) and option (v), and $Y_3$ and $Y_4$ are selected from the group consisting of the following (a) to (e):

(a)
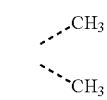

(b)
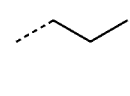

(c)
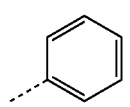
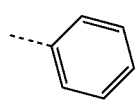

(d)

152
-continued (e)
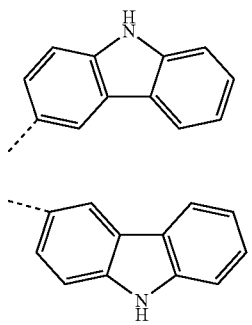

wherein, in each of (a) to (e), the dashed lines represent bonds to the boron (B).

13. A first device comprising an organic light emitting device, further comprising:
an anode;
a cathode; and
an organic layer, disposed between the anode and the cathode, the organic layer comprising an emissive dopant and a first host material selected from the group consisting of:

Complex 1
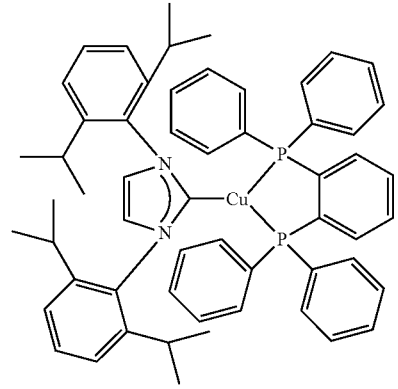

Complex 2
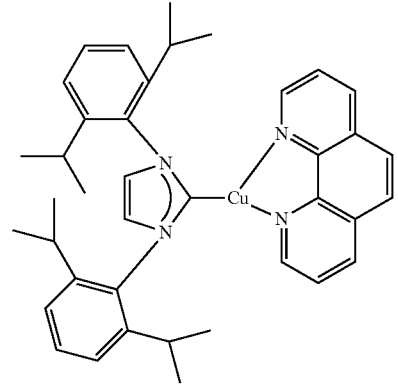

Complex 3
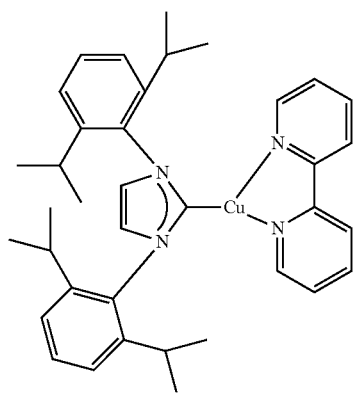
Complex 4
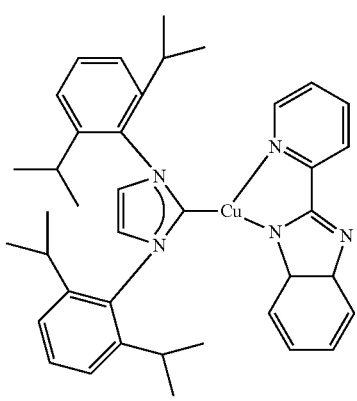
Complex 5
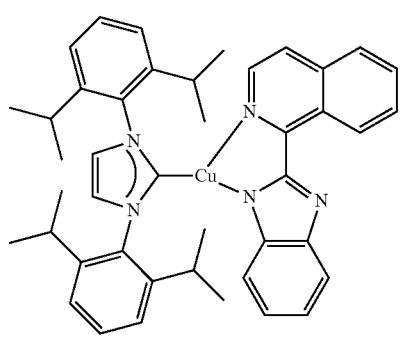
Complex 6
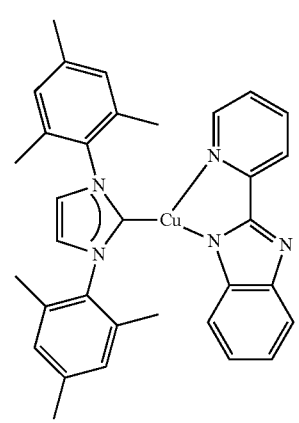
Complex 7
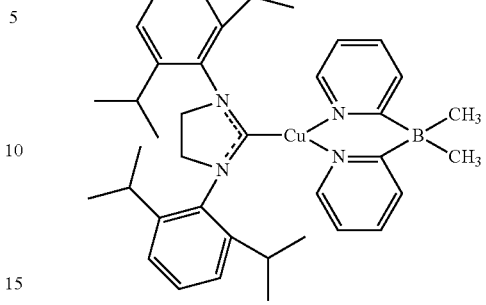
Complex 8
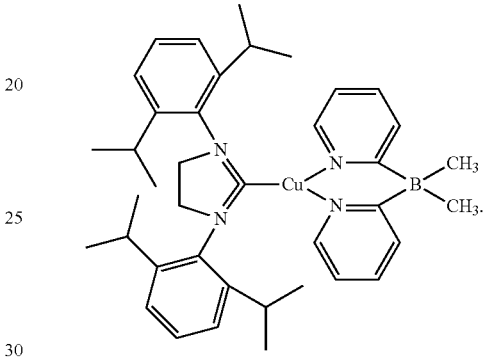
14. The device of claim 13, wherein the first host material is selected from the group consisting of:
Complex 1
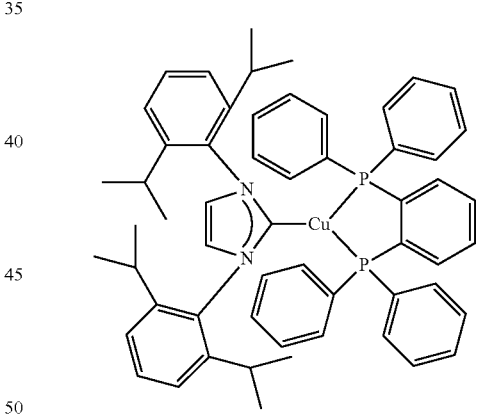
Complex 2
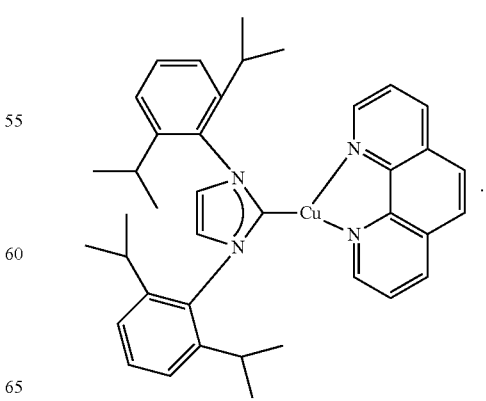

15. The device of claim 13, wherein the first host material is selected from the group consisting of:
Complex 3
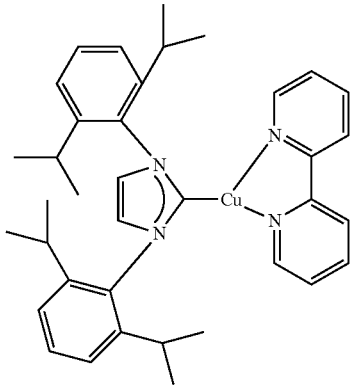
Complex 4
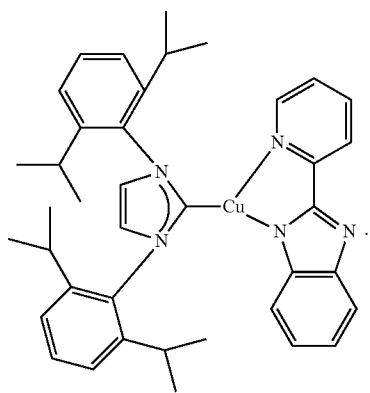
16. The device of claim 13, wherein the first host material is selected from the group consisting of:
Complex 5
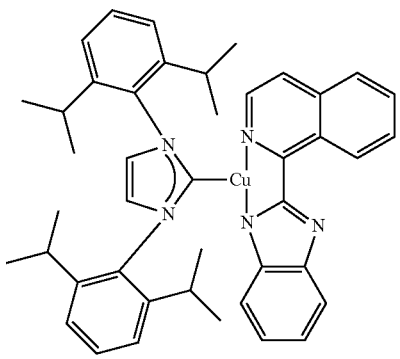
-continued
Complex 6
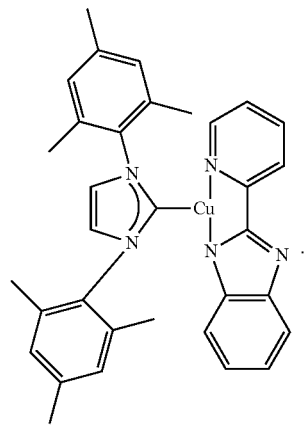
17. The device of claim 13, wherein the first host material is selected from the group consisting of:
Complex 7
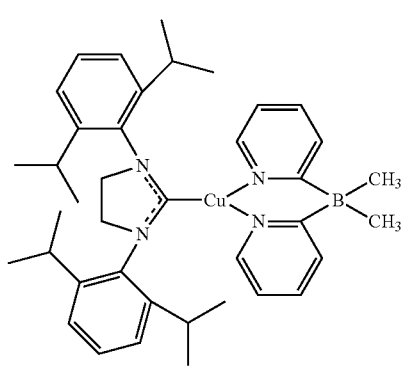
Complex 8
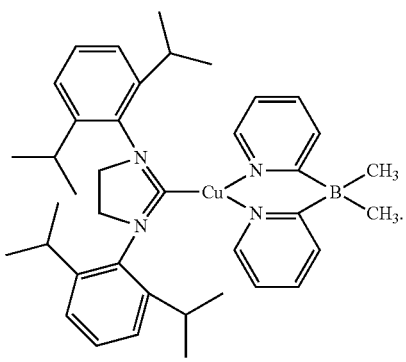
* * * * *